(12) United States Patent
Nifant'ev et al.

(10) Patent No.: US 7,112,638 B2
(45) Date of Patent: *Sep. 26, 2006

(54) HETERO CYCLIC METALLOCENE COMPOUNDS AND USE THEREOF IN CATALYST SYSTEM FOR PRODUCING OLEFIN POLYMERS

(75) Inventors: Ilya E. Nifant'ev, Moscow (RU); Simona Guidotti, Casalecchio di Reno (IT); Luigi Resconi, Ferrara (IT); Ilya P. Laishevtsev, Moscow (RU)

(73) Assignee: Basell Polyolefine GmbH, Wesseling (DE)

( * ) Notice: Subject to any disclaimer, the term of this patent is extended or adjusted under 35 U.S.C. 154(b) by 430 days.

This patent is subject to a terminal disclaimer.

(21) Appl. No.: 09/914,304

(22) PCT Filed: Dec. 22, 2000

(86) PCT No.: PCT/EP00/13191

§ 371 (c)(1),
(2), (4) Date: Aug. 27, 2001

(87) PCT Pub. No.: WO01/47939

PCT Pub. Date: Jul. 5, 2001

(65) Prior Publication Data

US 2003/0036612 A1 Feb. 20, 2003

(30) Foreign Application Priority Data

Dec. 28, 1999 (EP) .................................. 99204567

(51) Int. Cl.
C08F 4/44 (2006.01)
B01J 31/38 (2006.01)

(52) U.S. Cl. .................. 526/160; 526/161; 526/171; 526/943; 526/351; 502/117; 502/152; 556/43; 556/47; 556/53; 556/58; 556/112; 556/121; 556/143

(58) Field of Classification Search ............... 526/160, 526/161, 171, 943, 351; 556/43, 47, 53, 556/58, 112, 121, 143; 502/155
See application file for complete search history.

(56) References Cited

U.S. PATENT DOCUMENTS

| 4,335,225 | A |   | 6/1982 | Collette et al. ............ 525/240 |
| 6,017,615 | A | * | 1/2000 | Thakker et al. ............ 428/213 |
| 6,268,518 | B1 |  | 7/2001 | Resconi et al. ............ 556/43 |
| 6,444,833 | B1 | * | 9/2002 | Ewen et al. .............. 556/11 |

FOREIGN PATENT DOCUMENTS

| EP | 0633272 | 1/1995 |
| EP | 0693506 | 1/1996 |
| WO | 9200333 | 1/1992 |
| WO | 9525757 | 9/1995 |
| WO | 9526369 | 10/1995 |
| WO | 9532995 | 12/1995 |
| WO | 9822486 | 5/1998 |
| WO | WO 98/22486 | * 5/1998 |
| WO | 9921899 | 5/1999 |
| WO | 9940129 | 8/1999 |
| WO | 0121676 | 3/2001 |

OTHER PUBLICATIONS

Ewen et al., Polymerization Catalysts with Cyclopentadienyl Ligands Ring-Fused to Pyrrole and Thiophene Heterocycles, J. Am. Chem. Soc. 1998, 120 10786-10787.*
E. Hey-Hawkins, Chem. Rev., 94: 1661-1717 (1994).
G. Zotti et al., Synthetic Metals, 66: 149-155 (1994).
G. Zotti et al., Chem. Mater., 7: 2309-2315 (1995).
J. Ewen et al., J. Am. Chem. Soc., 120: 10786-10787 (1998).
U. Dietrich et al., J. Am. Chem. Soc., 121: 4348-4355 (1999).
L. Resconi et al., Chem. Rev., 100: 1253-1345 (2000).

* cited by examiner

Primary Examiner—Robert D. Harlan
(74) Attorney, Agent, or Firm—William R. Reid

(57) ABSTRACT

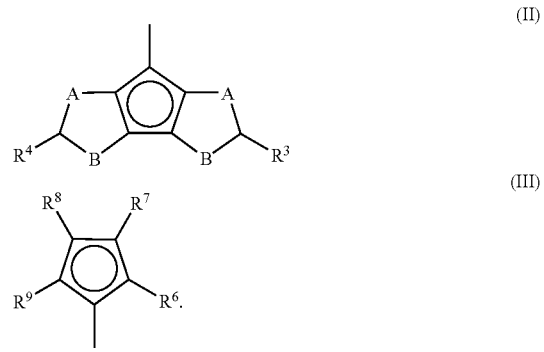

A metallocene compound of general formula (I): LGZMXp, wherein L is a divalent group, Z is a moiety of formula (II), wherein $R^3$ and $R^4$ are selected from hydrogen and hydrocarbon groups; A and B are selected from S, O or $CR^5$, wherein $R^5$ is selected from hydrogen and hydrocarbon groups, either A or B being different from $CR^5$; G is a moiety of formula (III), wherein $R^6$, $R^7$, $R^8$ and $R^9$ are selected from hydrogen and hydrocarbon groups, M is an atom of a transition metal, X is selected from a halogen atom, a $R^{10}$, $OR^{10}$, $OSO_2CF_3$, $OCOR_{10}$, $SR^{10}$, $NR^{10}_2$ or $PR^{10}_2$ group, wherein the substituents $R^{10}$ is hydrogen and a hydrocarbon group; p is an integer from 0 to 3.

35 Claims, No Drawings

HETERO CYCLIC METALLOCENE COMPOUNDS AND USE THEREOF IN CATALYST SYSTEM FOR PRODUCING OLEFIN POLYMERS

This application is the U.S. national phase of International Application PCT/EP00/13191, filed Dec. 22, 2000.

The present invention relates to a new class of metallocene compounds, to catalysts containing them and to a process carried out in the presence of said catalysts for the preparation of polymers of alpha-olefins, particularly propylene polymers, having a low degree of crystallinity. The present invention also relates to the ligands for those metallocenes and to a convenient process for their preparation.

Products of propylene homopolymerization can have varying degrees of crystallinity. The type and amount of crystallinity is largely dependent on the microstructure of the polypropylene. Polypropylene having predominantly isotactic or syndiotactic structure is partially crystalline, while polypropylene having predominantly atactic structure is amorphous. Propylene polymers are also known which have a reduced degree of crystallinity and show elastomeric properties. U.S. Pat. No. 4,335,225, for instance, discloses a fractionable, elastic polypropylene, having an isotactic content of 55% or less, which contain a diethyl ether-soluble fraction with an isotactic crystalline content of about 0.5–5% by weight. This polypropylene is prepared with a catalyst based on a tetraalkyl zirconium supported on a metal oxide. However, the elastomeric polypropylenes of this type, due to the fact that the catalyst systems which are used for their preparation have different catalytic sites, are endowed with a wide distribution of molecular weights which has a negative impact on their properties.

Metallocene catalysts have recently been used in the polymerization reaction of olefins. Operating in the presence of these catalysts, polymers characterized by a narrow molecular weight distribution and having structural characteristics of interest have been obtained. By polymerizing propylene in the presence of metallocene catalysts, amorphous or highly crystalline polypropylenes can be obtained depending on the metallocene used.

Certain metallocene catalysts are also known that can produce partially crystalline elastomeric polypropylene. International application WO 95/25757, for instance, describes unbridged metallocene catalysts that can produce isotactic-atactic stereoblock polypropylenes having elastomeric thermoplastic properties. Despite the homogeneity in molecular weight distribution, the tacticity distribution of these polymers is not homogeneous. Moreover, the activity is low. U. Dietrich et al. in "J. Am. Chem. Soc. 1999, 121, 4348–4355" describe metallocene catalysts that are able to produce thermoplastic elastic polypropylenes.

More recently, heterocyclic metallocene compounds have been used in the polymerization of alpha-olefins. International application WO 98/22486 discloses a class of metallocenes containing a cyclopentadienyl radical directly coordinating the central metal atom, to which are fused one or more rings containing at least one heteroatom. These metallocenes, in combination with a suitable cocatalyst, are used in the polymerization of olefins such as propylene. The working examples relate to the preparation of highly stereoregular polypropylene.

It would be desirable to provide a novel class of metallocenes which, when used in catalysts for the polymerization of olefins, in particular propylene, are capable of yielding polymers endowed with high molecular weights, narrow molecular weight distribution and a reduced degree of crystallinity. It would be most desirable to provide metallocene catalysts that can produce those polymers with high activity, such that the amount of catalyst remaining in the formed polymer is minimized.

A novel class of metallocene compounds has now been unexpectedly found, which achieves the above and other results.

According to a first aspect the present invention provides a metallocene compound of general formula (I):

wherein L is a divalent group bridging the moieties G and Z, selected from $CR^1R^2$, $SiR^1R^2$ and $(CR^1R^2)_2$, $R^1$ and $R^2$, which may be the same as or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-arylalkyl, $C_7$–$C_{20}$-arylalkyl radical, optionally containing heteroatoms belonging to groups 13–17 of the Periodic Table of the Elements, $R^1$ and $R^2$ can also form a ring having 3 to 8 atoms which can bear substituents;

Z is a moiety of formula (II):

wherein $R^3$ and $R^4$, which may be the same as or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-arylalkyl, $C_7$–$C_{20}$-arylalkyl radical, optionally containing heteroatoms belonging to groups 13–17 of the Periodic Table of the Elements, preferably at least one of $R^3$ and $R^4$ being different from hydrogen;

A and B are selected from sulfur (S), oxygen (O) or $CR^5$, wherein $R^5$ is selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, with the proviso that if A is S or O, then B is $CR^5$ or if B is S or O, then A is $CR^5$, i.e. either A or B being different from $CR^5$, and wherein the rings containing A and B have a double bond in the allowed position being two aromatic rings;

G is a moiety of formula (III):

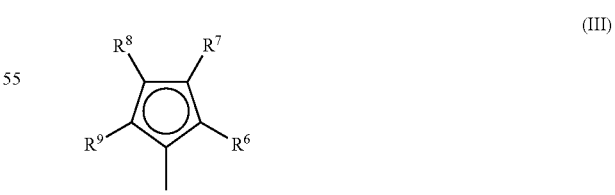

wherein $R^6$, $R^7$, $R^8$ and $R^9$, which may be the same as or different from each other, are selected from the group consisting of hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, $R^6$ and $R^7$ and/or $R^8$ and $R^9$ can form a ring comprising from 3 to 8 atoms, which can bear substituents;

with the proviso that $R^7$ is different from $R^8$ and when $R^7$ is a tert-butyl radical $R^8$ is not hydrogen;

M is an atom of a transition metal selected from those belonging to group 3, 4, 5, 6 or to the lanthanide or actinide groups in the Periodic Table of the Elements (new IUPAC version), X, same or different, is selected from a hydrogen atom, a halogen atom, a group $R^{10}$; $OR^{10}$, $OSO_2CF_3$, $OCOR^{10}$, $SR^{10}$, $NR^{10}{}_2$ or $PR^{10}{}_2$, wherein the substituents $R^{10}$ are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-arylalkyl, $C_7$–$C_{20}$-arylalkyl radical, optionally containing heteroatoms belonging to groups 13–17 of the Periodic Table of the Elements;

p is an integer from 0 to 3, preferably from 1 to 3, being equal to the formal oxidation state of the metal M minus 2;

isopropylidene(3-trimethylsilylcyclopentadienyl)(7-cyclopentadithiophene)zirconium dichloride, dimethylsilanediyl(3-trimethylsilylcyclopentadienyl)(7-cyclopentadithiophene)zirconium dichloride, isopropylidene(3-ethylcyclopentadienyl)(7-cyclopentadithiophene)zirconium dichloride, dimethylsilanediyl(3-ethylcyclopentadienyl)(7-cyclopentadithiophene)zirconium dichloride, isopropylidene(3-n-butylcyclopentadienyl)(7-cyclopentadithiophene)zirconium dichloride, dimethylsilanediyl(3-n-butylcyclopentadienyl)(7-cyclopentadithiophene)zirconium dichloride, isopropylidene(3-methylcyclopentadienyl)(7-cyclopentadithiophene)zirconium dichloride, dimethylsilanediyl(3-methylcyclopentadienyl)(7-cyclopentadithiophene)zirconium dichloride, isopropylidene(3-i-propylcyclopentadienyl)(7-cyclopentadithiophene) zirconium dichloride and dimethylsilanediyl(3-i-propylcyclopentadienyl)(7-cyclopentadithiophene) zirconium dichloride being excluded.

The transition metal M is preferably selected from titanium, zirconium and hafnium preferably having a formal oxidation state of +4. The X substituents are preferably chlorine atoms, benzyl or methyl groups. Preferably the bridging group L is a $CMe_2$ or $SiMe_2$ group. Preferably A or B is a sulfur atom and the other is a CH group, more preferably A is sulfur and B is a CH group. Preferably $R^3$ and $R^4$ are the same and are selected from a $C_1$–$C_{20}$-alkyl group, which can contain a silicon atom. Most preferably $R^3$ and $R^4$ are a methyl, an ethyl, a phenyl or a trimethylsilyl radical.

Non-limiting examples of metallocene compounds according to the present invention are:

methylene(3-methyl-cyclopentadienyl)-7-(2,5-dimethyl-cyclopentadienyl-[1,2-b:4,3-b']dithiophene)zirconium dichloride and dimethyl;

methylene(3-ethyl-cyclopentadienyl)-7-(2,5-dimethylcyclopentadienyl-[1,2-b:4,3-b']dithiophene)zirconium dichloride and dimethyl;

methylene(3-isopropyl-cyclopentadienyl)-7-(2,5-dimethylcyclopentadienyl-[1,2-b:4,3-b']dithiophene)zirconium dichloride and dimethyl;

methylene(3-phenyl-cyclopentadienyl)-7-(2,5-dimethyl-cyclopentadienyl-[1,2-b:4,3-b']dithiophene)zirconium dichloride and dimethyl;

methylene(2,4-dimethyl-cyclopentadienyl)-7-(2,5-dimethylcyclopentadienyl-[1,2-b:4,3-b']dithiophene)zirconium dichloride and dimethyl;

methylene(2,4-diethyl-cyclopentadienyl)-7-(2,5-dimethylcyclopentadienyl-[1,2-b:4,3-b']dithiophene)zirconium dichloride and dimethyl;

methylene(2,4-diisopropyl-cyclopentadienyl)-7-(2,5-dimethylcyclopentadienyl-[1,2-b:4,3-b']dithiophene)zirconium dichloride and dimethyl;

methylene(2,3,5-trimethyl-cyclopentadienyl)-7-(2,5-dimethylcyclopentadienyl-[1,2-b:4,3-b']dithiophene)zirconium dichloride and dimethyl;

methylene(2,3,5-triethyl-cyclopentadienyl)-7-(2,5-dimethylcyclopentadienyl-[1,2-b:4,3-b']dithiophene)zirconium dichloride and dimethyl;

methylene(2,3,5-triisopropyl-cyclopentadienyl)-7-(2,5-dimethylcyclopentadienyl-[1,2-b:4,3-b']dithiophene)zirconium dichloride and dimethyl;

methylene(3-cyclohexyl-cyclopentadienyl)-7-(2,5-dimethylcyclopentadienyl-[1,2-b:4,3-b']dithiophene)zirconium dichloride and dimethyl;

methylene-1-(indenyl)-7-(2,5-dimethylcyclopentadienyl-[1,2-b:4,3-b']dithiophene)zirconium dichloride and dimethyl;

methylene-1-(indenyl)-7-(2,5-ditrimethylsilylcyclopentadienyl-[1,2-b:4,3-b']dithiophene)zirconium dichloride and dimethyl;

methylene-1-(3-isopropyl-indenyl)-7-(2,5-dimethylcyclopentadienyl-[1,2-b:4,3-b']dithiophene)zirconium dichloride and dimethyl;

methylene-1-(3-ter-butyl-indenyl)-7-(2,5-dimethylcyclopentadienyl-[1,2-b:4,3-b']dithiophene)zirconium dichloride and dimethyl;

methylene-1-(2,3-dimethyl-indenyl)-7-(2,5-dimethylcyclopentadienyl-[1,2-b:4,3-b']dithiophene)zirconium dichloride and dimethyl;

methylene-1-(3-methyl-indenyl)-7-(2,5-dimethylcyclopentadienyl-[1,2-b:4,3-b']dithiophene)zirconium dichloride and dimethyl;

methylene-1-(tetrahydroindenyl)-7-(2,5-dimethylcyclopentadienyl-[1,2-b:4,3-b']dithiophene)zirconium dichloride and dimethyl;

methylene(3-methyl-cyclopentadienyl)-7-(2,5-dimethyl-cyclopentadienyl-[1,2-b:4,3-b']dioxazol)zirconium dichloride and dimethyl;

methylene(3-ethyl-cyclopentadienyl)-7-(2,5-dimethylcyclopentadienyl-[1,2-b:4,3-b']dioxazol)zirconium dichloride and dimethyl;

methylene(3-isopropyl-cyclopentadienyl)-7-(2,5-dimethylcyclopentadienyl-[1,2-b:4,3-b']dioxazol)zirconium dichloride and dimethyl;

methylene(3-phenyl-cyclopentadienyl)-7-(2,5-dimethyl-cyclopentadienyl-[1,2-b:4,3-b']dioxazol)zirconium dichloride and dimethyl;

methylene(2,4-dimethyl-cyclopentadienyl)-7-(2,5-dimethylcyclopentadienyl-[1,2-b:4,3-b']dioxazol)zirconium dichloride and dimethyl;

methylene(2,4-diethyl-cyclopentadienyl)-7-(2,5-dimethylcyclopentadienyl-[1,2-b:4,3-b']dioxazol)zirconium dichloride and dimethyl;

methylene(2-methyl-4-phenyl-cyclopentadienyl)-7-(2,5-dimethylcyclopentadienyl-[1,2-b:4,3-b']dioxazol)zirconium dichloride and dimethyl;

methylene(2,4-diisopropyl-cyclopentadienyl)-7-(2,5-dimethylcyclopentadienyl-[1,2-b:4,3-b']dioxazol)zirconium dichloride and dimethyl;

methylene(2,3,5-trimethyl-cyclopentadienyl)-7-(2,5-dimethylcyclopentadienyl-[1,2-b:4,3-b']dioxazol)zirconium dichloride and dimethyl;

methylene(2,3,5-triethyl-cyclopentadienyl)-7-(2,5-dimethylcyclopentadienyl-[1,2-b:4,3-b']dioxazol)zirconium dichloride and dimethyl;

methylene(2,3,5-triisopropyl-cyclopentadienyl)-7-(2,5-dimethylcyclopentadienyl-[1,2-b:4,3-b']dioxazol)zirconium dichloride and dimethyl;

methylene(3-cyclohexyl-cyclopentadienyl)-7-(2,5-dimethylcyclopentadienyl-[1,2-b:4,3-b']dioxazol)zirconium dichloride and dimethyl;

methylene-1-(indenyl)-7-(2,5-dimethylcyclopentadienyl-[1,2-b:4,3-b']dioxazol)zirconium dichloride and dimethyl;

methylene-1-(2-methyl-indenyl)-7-(2,5-dimethylcyclopentadienyl-[1,2-b:4,3-b']dioxazol)zirconium dichloride and dimethyl;

methylene-1-(2,3-dimethyl-indenyl)-7-(2,5-dimethylcyclopentadienyl-[1,2-b:4,3-b']dioxazol)zirconium dichloride and dimethyl;

methylene-1tetrahydroindenyl)-7-(2,5-dimethylcyclopentadienyl-[1,2-b:4,3-b']dioxazol)zirconium dichloride and dimethyl;

methylene(3-methyl-cyclopentadienyl)-4-(2,6-dimethylcyclopentadienyl-[2,1-b:4,3-b']dioxazol)zirconium dichloride and dimethyl;

methylene(3-isopropyl-cyclopentadienyl)-7-(2,5-ditrimethylsilylcyclopentadienyl-[1,2-b:4,3-b']dioxazol)zirconium dichloride and dimethyl;

methylene(3-methyl-cyclopentadienyl)-7-(2,5-ditrimethylsilylcyclopentadienyl-[1,2-b:4,3-b']dioxazol)hafnium dichloride and dimethyl;

isopropylidene(3-methyl-cyclopentadienyl)-7-(2,5-dimethylcyclopentadienyl-[1,2-b:4,3-b']dithiophene)zirconium dichloride and dimethyl;

isopropylidene(3-ethyl-cyclopentadienyl)-7-(2,5-dimethylcyclopentadienyl-[1,2-b:4,3-b']dithiophene)zirconium dichloride and dimethyl;

isopropylidene(3-isopropyl-cyclopentadienyl)-7-(2,5-dimethylcyclopentadienyl-[1,2-b:4,3-b']dithiophene)zirconium dichloride and dimethyl;

isopropylidene(3-phenyl-cyclopentadienyl)-7-(2,5-dimethylcyclopentadienyl-[1,2-b:4,3-b']dithiophene)zirconium dichloride and dimethyl;

isopropylidene2,4-dimethyl-cyclopentadienyl)-7-(2,5-dimethylcyclopentadienyl-[1,2-b:4,3-b']dithiophene)zirconium dichloride and dimethyl;

isopropylidene(2,4-dimethyl-cyclopentadienyl)-7-(2,5-ditrimethylsilylcyclopentadienyl-[1,2-b:4,3-b']dithiophene)zirconium dichloride and dimethyl;

isopropylidene(2,4-diethyl-cyclopentadienyl)-7-(2,5-dimethylcylopentadienyl-[1,2-b:4,3-b']dithiophene)zirconium dichloride and dimethyl;

isopropylidene(2,4-diisopropyl-cyclopentadienyl)-7-(2,5-dimethylcyclopentadienyl-[1,2-b:4,3-[b']dithiophene)zirconium dichloride and dimethyl;

isopropylidene(2-methyl-4-phenyl-cyclopentadienyl)-7-(2,5-dimethylcyclopentadienyl-[1,2-b:4,3-b']dithiophene)zirconium dichloride and dimethyl;

isopropylidene(2-methyl-4-phenyl-cyclopentadienyl)-7-(2,5-ditrimethylsilylcyclopentadienyl-[1,2-b:4,3-b']dithiophene)zirconium dichloride and dimethyl;

isopropylidene(2-methyl-4-isopropyl-cyclopentadienyl)-7-(2,5-dimethylcyclopentadienyl-[1,2-b:4,3-b']dithiophene)zirconium dichloride and dimethyl;

isopropylidene(2,3,5-trimethyl-cyclopentadienyl)-7-(2,5-dimethylcyclopentadienyl-[1,2-b:4,3-b']dithiophene)zirconium dichloride and dimethyl;

isopropylidene(2,3,5-triethyl-cyclopentadienyl)-7-(2,5-dimethylcyclopentadienyl-[1,2-b:4,3-b']dithiophene)zirconium dichloride and dimethyl;

isopropylidene(2,3,5-triisopropyl-cyclopentadienyl)-7-(2,5-dimethylcyclopentadienyl-[1,2-b:4,3-b']dithiophene)zirconium dichloride and dimethyl;

isopropylidene(3-cyclohexyl-cyclopentadienyl)-7-(2,5-dimethylcyclopentadienyl-[1,2-b:4,3-b']dithiophene)zirconium dichloride and dimethyl;

isopropylidene(3-isopropyl-cyclopentadienyl)-7-(2,5-ditrimethylsilylcyclopentadienyl-[1,2-b:4,3-b']dithiophene)zirconium dichloride and dimethyl;

isopropylidene(3-isopropyl-cyclopentadienyl)-4-(2,6-dimethylcyclopentadienyl-[2,1-b:3,4-b']dithiophene)zirconium dichloride and dimethyl;

isopropylidene-1-(indenyl)-7-(2,5-dimethylcyclopentadienyl-[1,2-b:4,3-b']dithiophene)zirconium dichloride and dimethyl;

isopropylidene-1-(3-methyl-indenyl)-7-(2,5-dimethylcyclopentadienyl-[1,2-b:4,3-b']dithiophene)zirconium dichloride and dimethyl;

isopropylidene-1-(2,3-dimethyl-indenyl)-7-(2,5-dimethylcyclopentadienyl-[1,2-b:4,3-b']dithiophene)zirconium dichloride and dimethyl;

isopropylidene-1-(3-isopropyl-indenyl)-7-(2,5-dimethylcyclopentadienyl-[1,2-b:4,3-b']dithiophene)zirconium dichloride and dimethyl;

isopropylidene-1-(3-tert-butyl-indenyl)-7-(2,5-dimethylcyclopentadienyl-[1,2-b:4,3-b']dithiophene)zirconium dichloride and dimethyl;

isopropylidene-1-(tetrahydroindenyl)-7-(2,5-dimethylcyclopentadienyl-[1,2-b :4,3-b']dithiophene)zirconium dichloride and dimethyl;

isopropylidene(3-methyl-cyclopentadienyl)-4-(2,6-dimethylcyclopentadienyl-[2,1-b:3,4-b']dithiophene)hafnium dichloride and dimethyl;

dimethylsilandiyl(3-methyl-cyclopentadienyl)-7-(2,5-dimethylcyclopentadienyl-[1,2-b:4,3-b']dithiophene)zirconium dichloride and dimethyl;

dimethylsilandiyl(3-ethyl-cyclopentadienyl)-7-(2,5-dimethylcyclopentadienyl-[1,2-b:4,3-b']dithiophene)zirconium dichloride and dimethyl;

dimethylsilandiyl(3-isopropyl-cyclopentadienyl)-7-(2,5-dimethylcyclopentadienyl-[1,2-b:4,3-b']dithiophene)zirconium dichloride and dimethyl;

dimethylsilandiyl(3-phenyl-cyclopentadienyl)-7-(2,5-dimethylcyclopentadienyl-[1,2-b:4,3-b']dithiophene)zirconium dichloride and dimethyl;

dimethylsilandiyl(2,4-dimethyl-cyclopentadienyl)-7-(2,5-dimethylcyclopentadienyl-[1,2-b:4,3-b']dithiophene)zirconium dichloride and dimethyl;

dimethylsilandiyl(2,4-diethyl-cyclopentadienyl)-7-(2,5-dimethylcyclopentadienyl-[1,2-b:4,3-b']dithiophene)zirconium dichloride and dimethyl;

dimethylsilandiyl(2,4-diisopropyl-cyclopentadienyl)-7-(2,5-dimethylcyclopentadienyl-[1,2-b:4,3-b']dithiophene)zirconium dichloride and dimethyl;

dimethylsilandiyl(2,3,5-trimethyl-cyclopentadienyl)-7-(2,5-dimethylcyclopentadienyl-[1,2-b:4,3-b']dithiophene)zirconium dichloride and dimethyl;

dimethylsilandiyl(2,3,5-triethyl-cyclopentadienyl)-7-(2,5-dimethylcyclopentadienyl-[1,2-b:4,3-b']dithiophene)zirconium dichloride and dimethyl;

dimethylsilandiyl(2,3,5-triisopropyl-cyclopentadienyl)-7-(2,5-dimethylcyclopentadienyl-[1,2-b:4,3-b']dithiophene)zirconium dichloride and dimethyl;

dimethylsilandiyl(3-cyclohexyl-cyclopentadienyl)-7-(2,5-dimethylcyclopentadienyl-[1,2-b:4,3-b']dithiophene)zirconium dichloride and dimethyl;

dimethylsilandiyl(3-trimethylsilyl-cyclopentadienyl)-7-(2,5-dimethylcyclopentadienyl-[1,2-b:4,3-b']dithiophene) zirconium dichloride and dimethyl;

dimethylsilandiyl-1-(indenyl)-7-(2,5-dimethylcyclopentadienyl-[1,2-b:4,3-b']dithiophene)zirconium dichloride and dimethyl;

dimethylsilandiyl-1-(3-methyl-indenyl)-7-(2,5-dimethyl-cyclopentadienyl-[1,2-b:4,3b']dithiophene)zirconium dichloride and dimethyl;

dimethylsilandiyl-1-(2,3-dimethyl-indenyl)-7-(2,5-dimethylcyclopentadienyl-[1,2-b:4,3-b']dithiophene)zirconium dichloride and dimethyl;

dimethylsilandiyl-1-(3-ethyl-indenyl)-7-(2,5-dimethylcyclopentadienyl-[1,2-b:4,3-b']dithiophene)zirconium dichloride and dimethyl;

dimethylsilandiyl-1-(3-isopropyl-indenyl)-7-(2,5-dimethylcyclopentadienyl-[1,2-b:4,3-b']dithiophene)zirconium dichloride and dimethyl;

dimethylsilandiyl-1-(3-isopropyl-indenyl)-4-(2,6-dimethylcyclopentadienyl-[2,1-b:3,4-b']dithiophene)zirconium dichloride and dimethyl;

dimethylsilandiyl-1-(3-isopropyl-indenyl)-7-(2,5-ditrimethylsilylcyclopentadienyl-[1,2-b:4,3-b']dithiophene)zirconium dichloride and dimethyl;

dimethylsilandiyl-1-(3-methyl-indenyl)-7-(2,5-dimethyl-cyclopentadienyl-[1,2-b:4,3-b']dithiophene)hafnium dichloride and dimethyl;

dimethylsilandiyl-1-(3-tertbutyl-indenyl)-7-(2,5-dimethylcyclopentadienyl-[1,2-b:4,3-b']dithiophene)zirconium dichloride and dimethyl;

dimethylsilandiyl-1-(tetrahydroindenyl)-7-(2,5-dimethyl-cyclopentadienyl-[1,2-b:4,3-b']dithiophene)zirconium dichloride and dimethyl;

isopropylidene(3-methyl-cyclopentadienyl)-7-(2,5-dimethylcyclopentadienyl-[1,2-b:4,3-b']dioxazol)zirconium dichloride and dimethyl;

isopropylidene(3-ethyl-cyclopentadienyl)-7-(2,5-dimethylcyclopentadienyl-[1,2-b:4,3-b']dioxazol)zirconium dichloride and dimethyl;

isopropylidene(3-isopropyl-cyclopentadienyl)-7-(2,5-dimethylcyclopentadienyl-[1,2-b:4,3-b']dioxazol)zirconium dichloride and dimethyl;

isopropylidene(3-phenyl-cyclopentadienyl)-7-(2,5-dimethylcyclopentadienyl-[1,2-b:4,3-b']dioxazol)zirconium dichloride and dimethyl;

isopropylidene(2,4-dimethyl-cyclopentadienyl)-7-(2,5-dimethylcyclopentadienyl-[1,2-b:4,3-b']dioxazol)zirconium dichloride and dimethyl;

isopropylidene(2,4-diethyl-cyclopentadienyl)-7-(2,5-dimethylcyclopentadienyl-[1,2-b:4,3-b']dioxazol)zirconium dichloride and dimethyl;

isopropylidene(2,4-diisopropyl-cyclopentadienyl)-7-(2,5ethylcyclopentadienyl-[1,2-b:4,3-b']dioxazol)zirconium dichloride and dimethyl;

isopropylidene(2,3,5-trimethyl-cyclopentadienyl)-7-(2,5-dimethylcyclopentadienyl-[1,2-b:4,3-b']dioxazol)zirconium dichloride and dimethyl;

isopropylidene(2,3,5-triethyl-cyclopentadienyl)-7-(2,5-dimethylcyclopentadienyl-[1,2-b:4,3-b']dioxazol)zirconium dichloride and dimethyl;

isopropylidene(2,3,5-triisopropyl-cyclopentadienyl)-7-(2,5-dimethylcyclopentadienyl-[1,2-b:4,3-b']dioxazol)zirconium dichloride and dimethyl;

isopropylidene(3-cyclohexyl-cyclopentadienyl)-7-(2,5-dimethylcyclopentadienyl-[1,2-b:4,3-b']dioxazol)zirconium dichloride and dimethyl;

isopropylidene(3-isopropyl-cyclopentadienyl)-7-(2,5-dimethylcyclopentadienyl-[1,2-b:4,3-b']dioxazol)zirconium dichloride and dimethyl;

isopropylidene-1-(indenyl)-7-(2,5-dimethylcyclopentadienyl-[1,2-b:4,3-b']dioxazol)zirconium dichloride and dimethyl;

isopropylidene-1-(3-methyl-indenyl)-7-(2,5-dimethylcyclopentadienyl-[1,2-b:4,3-b']dioxazol)zirconium dichloride and dimethyl;

isopropylidene-1-(3-ethyl-indenyl)-7-(2,5-dimethylcyclopentadienyl-[1,2-b:4,3-b']dioxazol)zirconium dichloride and dimethyl;

isopropylidene-1-(3-isopropyl-indenyl)-7-(2,5-dimethyl-cyclopentadienyl-[1,2-b:4,3-b']dioxazol)zirconium dichloride and dimethyl;

isopropylidene-2-(3-tert-butyl-indenyl)-7-(2,5-dimethyl-cyclopentadienyl-[1,2-b:4,3-b']dioxazol)zirconium dichloride and dimethyl;

isopropylidene-1-(tetrahydroindenyl)-7-(2,5-dimethylcy-clopentadienyl-[1,2-b:4,3-b']dioxazol)zirconium dichloride and dimethyl;

isopropylidene-1-(tetrahydroindenyl)-7-(2,5-dimethylcy-clopentadienyl-[1,2-b:4,3-b']dioxazol)hafnium dichloride and dimethyl;

dimethylsilandiyl(3-methyl-cyclopentadienyl)-7-(2,5-dimethylcyclopentadienyl-[1,2-b:4,3-b']dioxazol)zirconium dichloride and dimethyl;

dimethylsilandiyl(3-ethyl-cyclopentadienyl)-7-(2,5-dim-ethylcyclopentadienyl-[1,2-b:4,3-b']dioxazol)zirconium dichloride and dimethyl;

dimethylsilandiyl(3-isopropyl-cyclopentadienyl)-7-(2,5-dimethylcyclopentadienyl-[1,2-b:4,3-b']dioxazol)zirconium dichloride and dimethyl;

dimethylsilandiyl(3-phenyl-cyclopentadienyl)-7-(2,5-dimethylcyclopentadienyl-[1,2-b:4,3-b']dioxazol)zirconium dichloride and dimethyl;

dimethylsilandiyl(2,4-dimethyl-cyclopentadienyl)-7-(2,5-dimethylcyclopentadienyl-[1,2-b:4,3b']dioxazol)zirconium dichloride and dimethyl;

dimethylsilandiyl(2,4-diethyl-cyclopentadienyl)-7-(2,5-dimethylcyclopentadienyl-[1,2-b:4,3-b']dioxazol)zirconium dichloride and dimethyl;

dimethylsilandiyl(2,4-diisopropyl-cyclopentadienyl)-7-(2,5-dimethylcyclopentadienyl-[1,2; -b:4,3-b']dioxazol)zirconium dichloride and dimethyl;

dimethylsilandiyl(2,3,5trimethyl-cyclopentadienyl)-7-(2,5-dimethylcyclopentadienyl-[1,2-b:4,3-b']dioxazol)zirconium dichloride and dimethyl;

dimethylsilandiyl(2,3,5-triethyl-cyclopentadienyl)-7-(2,5-dimethylcyclopentadienyl-[1,2-b:4,3-b']dioxazol)zirconium dichloride and dimethyl;

dimethylsilandiyl(2,3,5-triisopropyl-cyclopentadienyl)-7-(2,5-dimethylcyclopentadienyl-[1,2-b:4,3-b']dioxazol)zirconium dichloride and dimethyl;

dimethylsilandiyl(3-cyclohexyl-cyclopentadienyl)-7-(2,5-dimethylcyclopentadienyl-[1,2-b:4,3-b']dioxazol)zirconium dichloride and dimethyl;

dimethylsilandiyl(3-isopropyl-cyclopentadienyl)-7-(2,5-dimethylcyclopentadienyl-[1,2-b:4,3-b']dioxazol)zirconium dichloride and dimethyl;

dimethylsilandiyl-1-(indenyl)-7-(2,5-methylcyclopentadienyl-[1,2-b:4,3-b']dioxazol) zirconium dichloride and dimethyl;

dimethylsilandiyl-1-(3-methyl-indenyl)-7-(2,5-b]ethylcyclopentadienyl-[1,2-b:4,3-b']dioxazol)zirconium dichloride and dimethyl;

dimethylsilandiyl-1-(2,3-dimethyl-indenyl)-7-(2,5-dimethylcyclopentadienyl-[1,2-b:4,3-b']dioxazol)zirconium dichloride and dimethyl;

dimethylsilandiyl-1-(3-isopropyl-indenyl)-7-(2,5-dimethylcyclopentadienyl-[1,2-b:4,3-b']dioxazol)zirconium dichloride and dimethyl;

dimethylsilandiyl-1-(tetrahydroindenyl)-7-(2,5-dimethyl-cyclopentadienyl-[1,2-b:4,3-b']dioxazol)zirconium dichloride and dimethyl;

isopropylidene(3-isopropyl-cyclopentadienyl)-7-(2,5-dimethyl-cyclopentadienyl-[1,2-b:4,3-b']-dithiophene)zirconium dichloride;

isopropylidene(3-methyl-cyclopentadienyl)-7-(2,5-dimethyl-cyclopentadienyl-[1,2-b:4,3-b']-dithiophene)zirconium dichloride;

isopropylidene(3-methyl-cyclopentadienyl)-7-(2,5-dimethyl-cyclopentadienyl-[1,2-b:4,3-b']-dithiophene)hafnium dichloride; and dimethyl A particularly interesting class of bridged metallocenes of formula (I) according to the present invention is that wherein G is a moiety of formula (IIIa):

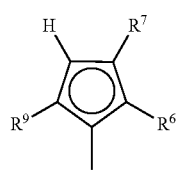

wherein $R^6$ and $R^9$ equal to or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-arylalkyl radical, optionally containing heteroatoms belonging to groups 13–17 of the Periodic Table of the Elements, preferably $R^6$ is hydrogen and $R^9$ is different from hydrogen;

$R^7$ is selected from a $C_6$–$C_{20}$-aryl, $C_7$–$C_{20}$-alkylaryl or a $QR^{11}R^{12}R^{13}$ group, wherein Q is selected from C, Si, Ge;

$R^{11}$, $R^{12}$ and $R^{13}$, which may be the same as or different from each other, are hydrogen, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-arylalkyl radicals, optionally containing a heteroatoms belonging to groups 13–17 of the Periodic Table of the Elements, with the proviso that when Q is a carbon atom, at least one of $R^{11}$, $R^{12}$ and $R^{13}$ is a hydrogen atom.

Particularly preferred metallocenes of the above mentioned class are those wherein $R^7$ is selected from a phenyl group, a $CHR^{11}R^{12}$ group and a $SiR^{11}R^{12}R^{13}$ group, $R^{11}$, $R^{12}$ and $R^{13}$ being hydrogen or $C_1$–$C_{20}$-alkyl groups.

Most preferred are those metallocene wherein $QR^{11}R^{12}R^{13}$ is an isopropyl or a trimethylsilyl group.

Non-limiting examples of this class of metallocenes are:

isopropylidene(3-isopropyl-cyclopentadienyl)-7-(2,5-dimethyl-cyclopentadienyl-[1,2-b:4,3-b']-dithiophene)zirconium dichloride;

isopropylidene(3-methyl-cyclopentadienyl)-7-(2,5-dimethyl-cyclopentadienyl-[1,2-b:4,3-b']-dithiophene)zirconium dichloride;

dimethylsilandiyl(3-trimethylsilyl-cyclopentadienyl)-7-(2,5-dimethyl-cyclopentadienyl-[1,2-b:4,3-b']-dithiophene) zirconium dichloride;

isopropylidene(2-methyl-4-isopropyl-cyclopentadienyl)-7-(2,5-dimethyl-cyclopentadienyl-[1,2-b:4,3-b']-dithiophene)zirconium dichloride;

isopropylidene(3-isopropyl-cyclopentadienyl)-7-(2,5-ditrimethylsilyl-cyclopentadienyl-[1,2-b:4,3-b']-dithiophene) zirconium dichloride;

isopropylidene(3-isopropyl-cyclopentadienyl)-4-(2,6-dimethyl-cyclopentadienyl-[2,1-b:3,4-b']-dithiophene)zirconium dichloride;

isopropylidene(2-methyl-4-phenyl-cyclopentadienyl)-7-(2,5-dimethyl-cyclopentadienyl-[1,2-b:4,3-b']-dithiophene) zirconium dichloride;

isopropylidene(3-phenyl-cyclopentadienyl)-7-(2,5-dimethyl-cyclopentadienyl-[1,2-b:4,3-b']-dithiophene)zirconium dichloride;

isopropylidene(2-methyl-4-phenyl-cyclopentadienyl)-7-(2,5-ditrimethylsilyl-cyclopentadienyl-[1,2-b:4,3-b']-dithiophene)zirconium dichloride;

isopropylidene(2,4-dimethyl-cyclopentadienyl)-7-(2,5-dimethyl-cyclopentadienyl-[1,2-b:4,3-b']-dithiophene)zirconium dichloride;

isopropylidene(2,4-dimethyl-cyclopentadienyl)-7-(2,5-ditrimethylsilyl-cyclopentadienyl-[1,2-b:4,3-b']-dithiophene)zirconium dichloride;

dimethylsilandiyl(2,4-dimethyl-cyclopentadienyl)-7-(2,5-dimethyl-cyclopentadienyl-[1,2-b:4,3-b']-dithiophene)zirconium dichloride; and isopropylidene(3-methyl-cyclopentadienyl)-7-(2,5-dimethyl-cyclopentadienyl-[1,2-b:4,3-b']-dithiophene)hafnium dichloride.

Another advantageous class of bridged metallocenes of formula (I) is that wherein G is a moiety of formula (IV):

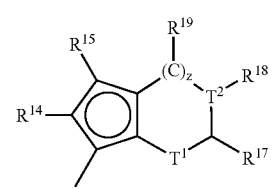

wherein $T^1$ is a sulfur atom or a $CR^{16}$ group;

$T^2$ is a carbon atom or a nitrogen atom;

z is 1 or 0;

the ring containing $T^1$ and $T^2$ has double bonds in the allowed position;

with the proviso that if z is 1, $T^1$ is a $CR^{16}$ group and $T^2$ is a carbon atom and the ring formed is a benzene ring; and if z is 0, $T^2$ bonds directly the cyclopentadienyl ring, the 5 membered ring formed has double bonds in any of the allowed position having an aromatic character and $T^1$ and $T^2$ are not at the same time, a sulfur atom and a nitrogen atom.

$R^{14}$, $R^{15}$, $R^{16}$, $R^{17}$, $R^{18}$ and $R^{19}$, the which may be the same as or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, and any of two adjacent $R^{14}$, $R^{15}$, $R^{16}$, $R^{17}$, $R^{18}$ and $R^{19}$ can form a ring comprising 4 to 8 atoms which can bear substituents.

An advantageous subclass of compounds belonging to the above class is that wherein G is a moiety of formula (IVa):

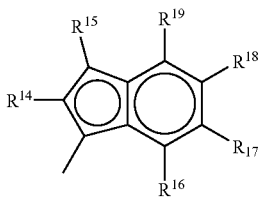

(IVa)

wherein $R^{14}$, $R^{15}$, $R^{16}$, $R^{17}$, $R^{18}$ and $R^{19}$, which may be the same as or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms, and any of two adjacent $R^{14}$, $R^{15}$, $R^{16}$, $R^{17}$, $R^{18}$ and $R^{19}$ can form a ring comprising 4 to 8 atoms which can bear substituents and the benzene ring can be perhydrated.

Non-limiting examples of metallocenes belonging to this class are:

dimethylsilandiyl-1-(indenyl)-7-(2,5-dimethyl-cyclopentadienyl-[1,2-b:4,3-b']-dithiophene)zirconium dichloride;

dimethylsilandiyl-1-(2-methyl-indenyl)-7-(2,5-dimethyl-cyclopentadienyl-[1,2-b:4,3-b']-dithiophene)zirconium dichloride.

A preferred structure of compounds of formula (IVa) has the formula (IVb):

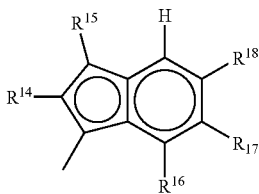

(IVb)

wherein $R^{15}$, $R^{16}$, $R^{17}$, and $R^{18}$ are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, and any of two adjacent $R^{14}$, $R^{16}$, $R^{17}$ and $R^{18}$ can form a ring comprising 4 to 8 atoms which can bear substituents; $R^{14}$ is selected from the group consisting of $C_1$–$C_{20}$-alkyl or $C_6$–$C_{20}$-aryl group such as a methyl ethyl, or phenyl group;

Preferably when G is a moiety of formula (IVb) L is a group $SiR^1R^2$, wherein $R^1$ and $R^2$ have the meaning described above, more preferably L is $SiMe_2$.

A further preferred structure of compounds of formula (IVa) has the formula (IVc)

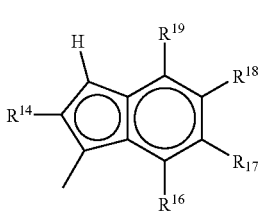

(IVc)

wherein $R^{14}$, $R^{16}$, $R^{17}$, and $R^{18}$ are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, optionally any of two adjacent $R^{14}$, $R^{16}$, $R^{17}$, $R^{18}$ and $R^{19}$ can form a ring comprising 4 to 8 atoms which can bear substituents;

$R^{19}$ is selected from the group consisting of $C_1$–$C_{20}$alkyl or $C_6$–$C_{20}$aryl group such as a methyl, ethyl, or phenyl group or forms with $R^{18}$ a benzene ring that can bears substituents.

Preferably $R^{14}$ is selected from the group consisting of $C_1$–$C_{20}$alkyl or $C_6$–$C_{20}$-aryl group such as a methyl, ethyl, or phenyl group; preferably $R^{16}$ is selected from the group consisting of $C_1$–$C_{20}$-alkyl or $C_6$–$C_{20}$-aryl group such as a methyl, ethyl, or phenyl group Preferably when G is a moiety of formula (IVc) L is a group $SiR^1R^2$, wherein $R^1$ and $R^2$ have the meaning described above, more preferably L is $SiMe_2$.

Another advantageous subclass of compounds wherein G is a moiety of formula (IV) is that wherein G is a moiety of formula (IVd)

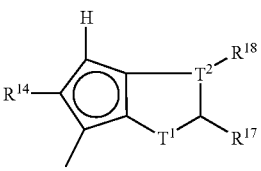

(IVd)

wherein:

$T^1$ is a sulfur atom or a $CR^{16}$ group;

$T^2$ is a carbon atom or a nitrogen atom; the 5 membered ring formed by $T^1$ and $T^2$ has double bonds in any of the allowed position, having an aromatic character;

with the proviso that if $T^1$ is a sulphur atom $T^2$ is not a nitrogen atom;

$R^{14}$, $R^{17}$ and $R^{18}$ which may be the same as or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, and $R^{17}$ and $R^{18}$ can form a ring comprising 4 to 8 atoms which can bear substituents.

Particularly preferred are those compounds wherein $T^2$ is a carbon atom; $T^1$ is sulphur and $R^{14}$, $R^{17}$ and $R^{18}$ equal to or different from each other are $C_1$–$C_{20}$alkyl, $C_6$–$C_{20}$-aryl; preferably $R^{14}$, $R^{17}$ and $R^{18}$ are methyl or phenyl groups.

Preferably when G is a moiety of formula (IVd) L is a group $SiR^1R^2$, wherein $R^1$ and $R^2$ have the meaning described above, more preferably L is $SiMe_2$ According to another aspect of the present invention there is provided a class of ligands of formula (V):

$$LG'Z' \qquad (V)$$

wherein L is defined as described above;

Z' is a moiety of formula (VI):

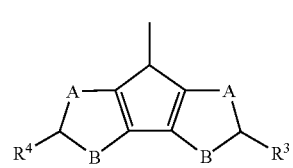

(VI)

and its double bond isomers;

wherein A, B, $R^3$ and $R^4$ are defined as described above and the double bonds are in any of the allowed position;

G' is a moiety of formula (VII):

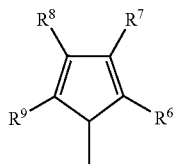

(VII)

and its double bond isomers;

wherein $R^6$, $R^7$, $R^8$ and $R^9$ have the meaning as defined above.

The ligand of formula (V) can be prepared according to the procedure known in the art, in particular when $R^4$ and $R^3$ are both hydrogen the ligand of formula (V) can be prepared as described in WO 98/22486.

According to a further aspect of the present invention a process is provided for the preparation of a ligand of formula (V) comprising the following steps:
a) contacting a compound of the formula (VIII) with a base selected from the group consisting of metallic sodium and potassium, sodium and potassium hydroxide and an organolithium compound, wherein the molar ratio between the compound of the formula (VIII) and said base is at least 1:1

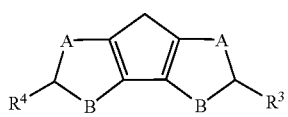

(VIII)

wherein A, B, $R^3$ and $R^4$ are described above;
b) contacting the obtained anionic compounds of formula (VIII) with a compound of formula (IX):

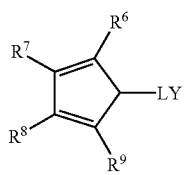

(IX)

wherein L, $R^6$, $R^7$, $R^8$ and $R^9$ are defined as above and Y is a halogen radical selected from the group consisting of chloride, bromide and iodide, preferably chlorine and bromine.

When L is $CR^1R^2$ the ligand of formula (V) can be obtained by an alternative process comprising the following steps:
a) contacting a compound of the formula (VIII) with a base selected from the group consisting of metallic sodium and potassium, sodium and potassium hydroxide and an organolithium compound, wherein the molar ratio between the compound of the formula (VIII) and said base is at least 1:1;

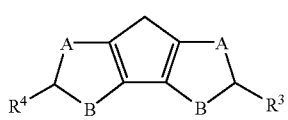

(VIII)

b) contacting the obtained anionic moiety of the formula (VI) with a compound of formula (X):

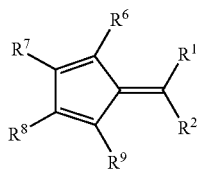

(X)

wherein $R^1$, $R^2$, $R^6$, $R^7$, $R^8$ and $R^8$ have the meaning as defined above; and then treating the obtained product with a protonating agent.

The base used in step a) of both processes is preferably methyllithium or n-butyllithium. Preferably the protonating agent used in the above process is a quaternary ammonium salt and most preferably the protonating agent is ammonium chloride.

Non limiting examples of the compound of formula (X) is selected from 6,6-dimethylfulvene and 3-isopropyl-6,6-dimethylfulvene.

Non-limiting examples of compounds of formula (IX) are (3-methyl-cyclopentadienyl)dimethylchlorosilane, (3-isopropyl-cyclopentadienyl)dimethyl chlorosilane, 1-(3-methyl-cyclopentadienyl)-1,1-dimethyl-2,2-dimethyl-2-chloro-ethane and 1-(3-isopropyl-cyclopentadienyl)-1,1-dimethyl-2,2-dimethyl-2-chloro-ethane.

The compound of formula (VIII) in the case where B is a $CR^5$ can be obtained by a process comprising the following steps:
i) treating a compound of formula (XI):

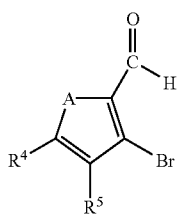

(XI)

wherein A is sulfur or oxygen, with a compound of formula (XII):

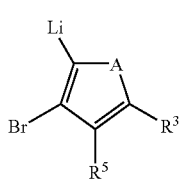

(XII)

wherein A is sulfur or oxygen,
ii) contacting the thus obtained product with a reducing agent in a molar ratio between said reducing agent and the product obtained under i) of at least 1;
iii) contacting the product obtained under ii) with a compound selected from an organolithium compound, sodium and potassium in a molar ratio between said compound and the product obtained in step ii) of equal to or greater than 2;

iv) treating the thus obtained product with an agent selected from the group consisting of copper chloride, copper iodide and Mg/Pd., in order to obtain a compound of general formula (XIII):

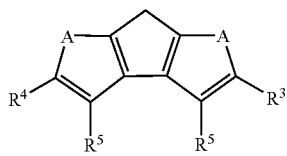

(XIII)

When B is sulfur or oxygen and A is a $CR^5$ group the compound of formula (VIII) can be obtained according to the process comprising the following steps:

i) contacting a compound of formula (XIV):

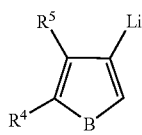

(XIV)

wherein B is sulfur or oxygen,
with a compound of formula (XV):

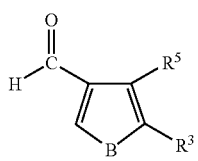

(XV)

wherein B is sulfur or oxygen,
and subsequently treating with a neutralization agent;

ii) treating the thus obtained product with a reducing agent in a molar ratio between said reducing agent and the compound obtained under i) of at least 1;

iii) contacting the thus obtained product with a mixture of an organolithium compound and tetramethylethylenediamine (TMEDA) in a molar ratio between said mixture and the product obtained under ii) of at least 2, iv) contacting the thus obtained product with an agent selected from the group consisting of copper chloride, copper iodide and Mg/Pd., in order to obtain a compound of formula (XVI):

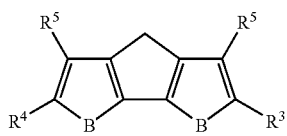

(XVI)

An alternative process for preparing the compound of formula (VIII) when A is S or O comprises the following steps:

i) contacting an equimolar mixture of compounds of formulae (XVII) and (XVIII):

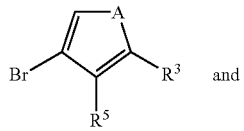

XVII and

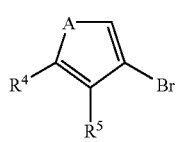

XVIII wherein A are sulfur or oxygen,
with a Lewis acid or a mixture of a Lewis acid and a protonic acid;

ii) treating the thus obtained product with $CH_2O$ in a molar ratio between said mixture and $CH_2O$ within a range between 10:1 and 1:10;

iii) contacting the thus obtained product with a compound selected from an organolithium compound, sodium and potassium;

iv) contacting the thus obtained product with an agent selected from the group consisting of copper chloride, iodine and Mg/Pd., in order to obtain a compound of general formula (XIII).

The Lewis acid used in the above process is preferably selected from zinc dichloride, cadmium dichloride, mercury dichloride, tin tetrachloride, trifluoroborane, zirconium tetrachloride and titanium tetrachloride. Most preferably, the Lewis acid is zinc dichloride.

The agent used in the above processes of the invention is preferably copper chloride.

Preferably the reducing agent is a mixture of $AlCl_3$/$LiAlH_4$.

The organic lithium compound used above is preferably butyllithium.

Another alternative process for preparing the compound of formula (VIII) when A is S or O comprises the following steps:

i) contacting a compound of formula (XIX):

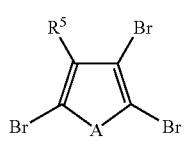

(XIX)

with a base selected from an organolithium compound, sodium or potassium; treating the obtained product with a formic ester, wherein the molar ratio between said ester and the compound of formula (XIX) is at least 1:2, and subsequently treating the obtained product with a reducing agent in order to obtain a compound of formula (XX):

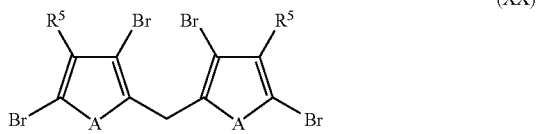

(XX)

ii) contacting the compound of formula (XX) with a base selected from an organolithium compound, sodium or potassium and subsequently treating the dimetallated compound with an alkylating agent to obtain the compound of formula (XXI);

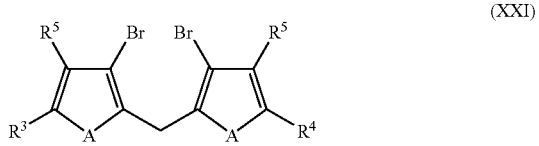

(XXI)

or alternatively treating the dimetallated compound with an ester of boric acid and a protonating agent in order to obtain the compound of formula (XXII):

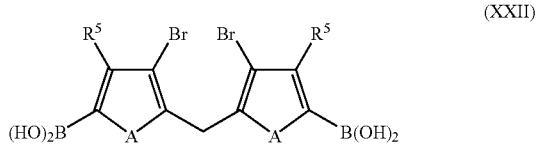

(XXII)

and subsequently contacting with a mixture of an alkylating agent in the presence of an transition metal complex compound for obtaining the compound of formula (XXI);
iii) contacting the alkylated compound obtained by step b) with a coupling agent; in order to obtain the compound of formula (XIII).

Preferably the alkylating agent is selected from dimethylsulphate Me$_2$SO$_4$), trimethylchlorosilane (Me$_3$SiCl) and a mixture of compounds of formulae R$^3$Y' and R$^4$Y', wherein R$^3$ and R$^4$ are defined as above and Y' is selected from chloride, bromide and iodide, preferably Y' is a chlorine. Preferably the transition metal complex compound is PdCl$_2$ (dppf).

In the above-described processes the reducing agent is preferably a mixture of AlCl$_3$/LiAlH$_4$ or a mixture of triethylsilane (Et$_3$SiH) and CF$_3$COOH. The preferred the base is butyllithium.

Preferably the organic acid ester is an ester of formic acid. Preferably the coupling agent is selected from the group consisting of copper chloride, copper iodide and Mg/Pd.

All the reactions are carried out in aprotic solvents. Non limiting examples of aprotic solvents suitable for the above reported processes are tetrahydrofurane, dimethoxyethane, diethylether, toluene, dichloromethane, pentane, hexane and benzene.

During the whole process, the temperature is generally kept between −100° C. and 80° C., preferably between −20° C. and 40° C.

Compounds of formula (V) can be suitable used as intermediates for the preparation of metallocenes of formula (I).

Therefore, a still further aspect of the present invention is a process for the preparation of a metallocene compound of formula (I), obtainable by contacting the ligand of general formula (V), with a compound capable of forming the corresponding dianionic compound and thereafter with a compound of general formula MX$_{p+2}$, wherein M, X and p are defined as above.

The compound able to form said corresponding dianionic compound is selected from the group consisting of hydroxides of alkali- and alkaline-earth metals, metallic sodium and potassium, and organometallic lithium salts.

Preferably, the compound able to form said corresponding dianionic compound is butyllithium.

Non-limiting examples of compounds of formula MX$_{p+2}$ are titanium-, zirconium- and hafnium tetrachloride.

More specifically, the ligand of formula (V) is dissolved in a polar aprotic solvent and to the obtained solution is added a solution of an organolithium compound in an apolar solvent. The thus obtained anionic compound is optionally separated, dissolved or suspended in a polar aprotic solvent and thereafter added to a suspension of the compound MX$_{p+2}$ in a polar aprotic solvent. At the end of the reaction, the solid product obtained is separated from the reaction mixture by techniques commonly used in the state of the art such as filtration or recrystallization.

Non limiting examples of polar aprotic solvents suitable for the above reported processes are tetrahydrofurane, dimethoxyethane, diethylether and dichloromethane. Non limiting examples of apolar solvents suitable for the above process are pentane, hexane, benzene and toluene. Throughout the process, the temperature is generally kept between −100° C. and 80° C., preferably between −20° C. and 40° C.

In the case in which at least one substituent X in the metallocene compound of the formula (I) is different from halogen an alternative process for preparing it consists in preparing the dihalogen derivative, i.e. the complex wherein both X substituents are halogen, and then substituting the halogen atoms with the appropriate X groups by the methods generally applied. For example, if the desired substituents X are alkyl groups, the metallocenes can be made by reaction with alkylmagnesium halides (Grignard reagents) or with alkyllithium compounds. General methods for substituting X with substituents other than halogen such as sulfur, phosphorus, oxygen, etc. are described in Chem. Rev. 1994, 94, 1661–1717, and the cited references therein.

According to a still further aspect of the present invention a catalyst for the polymerization of alpha-olefins is provided, obtainable by contacting:
(A) a metallocene compound of formula (I)

LGZMX$_p$ (I)

wherein L, Z, M, X, and p has been defined above and G is a moiety of formula (III):

(III)

wherein $R^6$, $R^7$, $R^8$ and $R^9$, which may be the same as or different from each other, are selected from the group consisting of hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$arylalkyl radical, optionally containing heteroatoms belonging to groups 13–17 of the Periodic Table of the Elements, $R^6$ and $R^7$ and/or $R^8$ and $R^9$ can form a ring comprising from 3 to 8 atoms, which can bear substituents; with the proviso that $R^7$ is different from $R^8$ and when $R^7$ is a tertbutyl radical $R^8$ is not hydrogen; and (B) an alumoxane and/or a compound capable of forming an alkyl metallocene cation. Preferably in the metallocene compound of formula (I) G is a moiety of formula (IIIa) or (IV), more preferably G is a moiety selected from the compound of formula (IIIa), (IVb), (IVc) or (IVd).

The alumoxane used as component (B) can be obtained by reacting water with an organo-aluminium compound of formula $H_jAlR^{23}_{3-j}$ or $H_jAl_2R^{23}_{6-j}$, where $R^{23}$ substituents, same or different, are hydrogen atoms, $C_1$–$C_{20}$-allyl, $C_3$–$C_{20}$-cyclalkyl, $C_6$–$C_{20}$-aryl, $C_7$–$C_{20}$-alkylaryl or $C_7$–$C_{20}$-arylalkyl, optionally containing silicon or germanium atoms with the proviso that at least one $R^{23}$ is different from halogen, and J ranges from 0 to 1, being also a non-integer number. In this reaction the molar ratio of Al/water is preferably comprised between 1:1 and 100:1.

The molar ratio between aluminium and the metal of the metallocene is comprised between about 10:1 and about 20000:1, and more preferably between about 100:1 and about 5000:1.

The alumoxanes used in the catalyst according to the invention are considered to be linear, branched or cyclic compounds containing at least one group of the type:

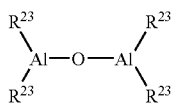

wherein the substituents $R^{23}$, same or different, are described above.

In particular, alumoxanes of the formula:

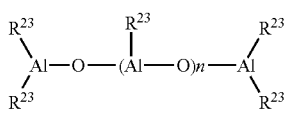

can be used in the case of linear compounds, wherein n is 0 or an integer from 1 to 40 and the substituents R are defined as above, or alumoxanes of the formula:

can be used in the case of cyclic compounds, wherein u is an integer from 2 to 40 and the $R^{23}$ substituents are defined as above.

Examples of alumoxanes suitable for use according to the present invention are methylalumoxane (MAO), tetra-(isobutyl)alumoxane (TIBAO), tetra-(2,4,4trimethyl-pentyl) alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 and in PCT/EP00/09111 in which the alkyl and aryl groups have specific branched patterns.

Non-limiting examples of aluminium compounds according to said PCT applications are:

tris(2,3,3-trimethyl-butyl)aluminum, tris(2,3-dimethylhexyl)aluminium, tris(2,34dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminum, tris[2-(4-fluorophenyl)-propyl]aluminium, tris[2-(4-chloro-phenyl)-propyl] aluminium, tris[2-(3-isopropyl-phenyl)-propyl]aluminium, tris(2-phenyl-butyl)aluminium, tris(3-methyl-2-phenyl-butyl)aluminium, tis(2-phenyl-pentyl)aluminium, tris[2-(pentafluorophenyl)-propyl]aluminium, tris[2,2-diphenyl-ethyl] aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminum (TMA), triisobutylaluminum (TBAL), tris(2,4,trimethyl-pentyl)aluminium (TIOA), tris(2,3-dimethylbutyl)aluminium (TDMBA) and tris(2,3,3-trimethylbutyl)aluminium (TTMBA) are preferred.

Non-limiting examples of compounds able to form an alkylmetallocene cation are compounds of formula $D^+E^-$, wherein $D^+$ is a Brønsted acid, able to donate a proton and to react irreversibly with a substituent X of the metallocene of formula (I) and $E^-$ is a compatible anion, which is able to stabilize the active catalytic species originating from the reaction of the two compounds, and which is sufficiently labile to be able to be removed by an olefinic monomer. Preferably, the anion $E^-$ consists of one or more boron atoms. More preferably, the anion $E^-$ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred. Moreover, compounds of the formula $BAr_3$ can conveniently be used. Compounds of this type are described, for example, in the published International patent application WO 92100333. Further, compounds of the formula RM'-O-M'R, R being an alkyl or aryl group, and M' is selected from an element of the Group 13 of the Periodic Table of the Elements (new IUPAC version). Compounds of this type are described, for example, in the International patent application WO 99/40129.

The catalysts of the present invention can also be supported on an inert carrier. This is achieved by depositing the metallocene compound (A) or the product of the reaction thereof with the component (B), or the component (B) and then the metallocene compound (A) on supports such as, for example, silica, alumina, magnesium halides, styrene/divinylbenzene copolymers, polyethylene or polypropylene. The supportation process is carried out in an inert solvent such as hydrocarbon for example toluene, hexane, pentane or propane and at a temperature ranging from 0° C. to 100° C., preferably the process is carried out at room temperature.

A suitable class of supports which can be used is that constituted by porous organic supports functionalized with groups having active hydrogen atoms. Particularly suitable are those in which the organic support is a partially crosslinked styrene polymer. Supports of this type are described in European application EP-633272.

Another class of inert supports particularly suitable for use according to the invention is that of the olefin, particularly propylene, porous prepolymers described in International application WO 95/26369.

A further suitable class of inert supports for use according to the invention is that of porous magnesium halides such as those described in International application WO 95/32995.

The solid compound thus obtained, in combination with the further addition of the alkylaluminium compound either as such or prereacted with water if necessary, can be usefully employed in the gas-phase polymerization.

According to a still further aspect of the present invention a process is provided for the preparation of polymers of alpha-olefins comprising contacting one or more alpha-olefins under polymerization conditions with a catalyst comprising the product obtainable by contacting:
(A) a metallocene compound of formula (I)

$$LGZMX_p \qquad (I)$$

wherein L, Z, M, X, and p has been defined above and G is a moiety of formula (III):

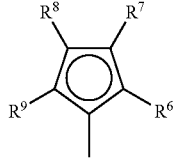

(III)

wherein $R^6$, $R^7$, $R^8$ and $R^9$, which may be the same as or different from each other, are selected from the group consisting of hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13–17 of the Periodic Table of the Elements, $R^6$ and $R^7$ and/or $R^8$ and $R^9$ can form a ring comprising from 3 to 8 atoms, which can bear substituents; with the proviso that $R^7$ is different from $R^8$ and when $R^7$ is a tert-butyl radical $R^8$ is not hydrogen; and
(B) an alumoxane and/or a compound capable of forming an alkyl metallocene cation.

Preferably in the metallocene compound of formula (I) G is a moiety of formula (IIIa) or (IV), more preferably G is a moiety selected from the compound of formula (IIIa), (IVB), (IVc) or (IVd).

The process for the polymerization of olefins according to the invention can be carried out in the liquid phase in the presence or absence of an inert hydrocarbon solvent, or in the gas phase. The hydrocarbon solvent can either be aromatic such as toluene, or aliphatic such as propane, hexane, heptane, isobutane or cyclohexane.

The polymerization temperature is generally comprised between –100° C. and +100° C. and, particularly between 10° C. and +90° C. The polymerization pressure is generally comprised between 0,5 and 100 bar.

The lower the polymerization temperature, the higher are the resulting molecular weights of the polymers obtained.

The polymerization yields depend on the purity of the metallocene compound of the catalyst. The metallocene compounds obtained by the process of the invention can therefore be used as such or can be subjected to purification treatments.

The components of the catalyst can be brought into contact with each other before the polymerization. The pre-contact concentrations are generally between 0.1 and $10^{-8}$ mol/l for the metallocene component (A), while they are generally between 2 and $10^{-8}$ mol/l for the component (B). The pre-contact is generally effected in the presence of a hydrocarbon solvent and, if appropriate, of small quantities of monomer. It the pre-contact it is also possible to use a non-polymerizable olefin such as isobutene, 2-butene and the like.

Further, the molecular weights of the polymer obtained, in particular of propylene homo or polymers, 1-butene polymers or ethylene homo or copolymers, are distributed over relatively limited ranges. The molecular weight distribution can be represented by the ratio Mw/Mn which, for the present polymers, is generally lower than 4, preferably lower than 3.5 and, more preferably, lower than 3.

The molecular weight distribution can be varied by using mixtures of different metallocene compounds or by carrying out the polymerization in several stages which differ as to the polymerization temperature and/or the concentrations of the molecular weight regulators.

One of the preferred alpha-olefins to be used in the polymerization process of the present invention is propylene. When propylene is polymerized and G is a moiety selected from the compound of formula (IIIa) and (IVb) a propylene polymer having a melting enthalpy <70 J/g; and triads (mm) satisfying the relation: 30<mm<85 can generally be obtained. When G is a moiety selected from the compound of formula (IVc), (IVd) the polymer obtained generally have a catalyst activity and/or intrinsic viscosity higher than those obtained with similar catalyst used in the prior art. For example in J. Am. Chem. Soc. 1998, 120, 10786–10787 isopropylidene{(3-tertbutyl-cyclopentadienyl)-7-(2,5-ditrimethylsilyl-cyclopenta[1,2-b:4,3-b']-dithiophene)}zirconium dichloride was used for polymerizing propylene, with a catalyst activity of only 13 Kg/mmol cath. The polymers obtained generally have the triads (mm) satisfying the relation: 70<mm<95 preferably 85<mm<95 and an intrinsic viscosity (I.V. measured in tetrahydronaphtalene (THN) solution) higher than 0.7 preferably 0.8, more preferably higher than 1, even more preferably higher than 2.

More interesting propylene polymers obtainable with the process described above are propylene polymer having the following characteristics:
  triads (mm) satisfying the relation 30<mm<85 preferably 55<mm<85 and more preferably 65<mm<85
  melting enthalpy (ΔH)<70 J/g, preferably comprised between 5 J/g and 70 J/g more preferably comprised between 20 J/g and 70 J/g.

The molecular weights of the above said propylene polymers can be quite high. Thus, the intrinsic viscosity can reach values of greater than 0.7 dl/g, preferably greater than 1 dl/g, more preferably greater than 2.

The propylene polymers described above are endowed with good balance between optical properties, being quite transparent and elastomeric properties. Thus the polypropylene of the present invention has the following properties:

Haze (ASTM 2457) from 15% to 30%, preferably from 20% to 30%;
Gloss (60° C.) (ASTM 2457) from 60% to 95%, preferably from 70% to 85%;
Tensile modulus (ASTM D4065) from 1000 Mpa to 200 Mpa, preferably from 700 Mpa to 400 Mpa;
Elongation at break (ASTM D4065) from 300% to 900%, preferably from 500% to 700%;
Strength at break (ASTM D638) from 10% to 40%, preferably from 10% to 30%.

The microstructures of polypropylene obtained by the process of the present invention, cover a range of commercial copolymers such as elastomeric, flexible, and random-like polypropylene, but with the difference that the melting point of the polypropylene of the present invention is always higher than the cited copolymer. Thus polypropylene of the present invention can easily replace these more expensive copolymers.

The polymerization reaction of propylene according to the invention can be carried out in the presence of ethylene or of a $C_4$–$C_{10}$ alpha-olefin comonomer. Thus a further aspect of the present invention is a propylene copolymer containing from 0.1 to 30% by moles, preferably from 0.1 to 20% by moles, more preferably from 0.1 to 10% by moles, even more preferably from 0.1 to 5% by moles of units deriving from an olefin of formula $CH_2$=$CHR'$, R' being hydrogen, a $C_2$–$C_{20}$-alkyl or a $C_6$–$C_{12}$-aryl group, said propylene copolymer having the following characteristics:

melting enthalpy<70 J/g, preferably<50 J/g;
triads (mm) of the polypropylene homosequences satisfy the relation: 30<mm<85, preferably 55 <mm<85.

Non-limiting examples of alpha-olefins which can be used as comonomers in the copolymers according to the present invention are ethylene, 1-butene, 1-pentene, 1-hexene, 4-methyl-1-pentene, 1-octene, 1-decene, 1-dodecene, styrene, 1,5-hexadiene and 1,7-octadiene. A preferred comonomer is ethylene.

The process according to the present invention is also suitable for obtaining ethylene homo and copolymers wherein the olefin comonomers can be alpha-olefins, cyclolefins or polyenes. Ethylene homopolymers having a remarkably high molecular weight are obtainable. In fact, with the process of the present invention it is possible to obtain ethylene polymers having intrinsic viscosity (I.V.) values as high as 5.0 dl/g and even higher.

In the copolymers obtainable with the process of the invention, the molar content of ethylene derived units is generally higher than 40%, and preferably it is comprised between 50% and 99%, and most preferably it is comprised between 80% and 98%.

The molar content of alpha-olefin derived units is preferably comprised between 0% and 60% and, more preferably, between 1% and 50%, and most preferably between 2% and 20%.

Non-limiting examples of alpha-olefins which can be used as alpha-olefins in the process of the invention are propylene, 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene, 1-eicosene and allylcyclohexane.

Non-limiting examples of cycloolefins that can be used as comonomers in the process of the present invention are cyclopentene, cyclohexene and norbornene.

The copolymers according to the invention can also contain units derived from polyenes. The content of polyene derived units, if any, is preferably comprised between 0% and 30 mol % and, more preferably between 0% and 20 mol %.

The polyenes that can be used as comonomers in the copolymers according to the present invention are included in the following classes:

non-conjugated diolefins able to cyclopolymerize such as, for example, 1,5-hexadiene, 1-6-heptadiene, 2-methyl-1,5-hexadiene;
dienes capable of giving unsaturated monomeric units, in particular conjugated dienes such as, for example, butadiene and isoprene, and linear non-conjugated dienes, such as, for example, trans 1,4-hexadiene, cis 1,4-hexadiene, 6-methyl-1,5-heptadiene, 3,7-dimethyl-1,6-octadiene, 11-methyl-1,10-dodecadiene, and cyclic non-conjugated dienes such as 5-ethylidene-2-norbornene The metallocenes of the present invention can also be used for the polymerization in gas phase of ethylene with alpha-olefins such as propylene, 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene, 1-eicosene and allylcyclohexane.

In the case of ethylene/propylene copolymers, the product of the reactivity ratios $r_1.r_2$, wherein $r_1$ is the reactivity ratio of propylene and $r_2$ that of ethylene, is calculated according to the following formula:

$$r_1 r_2 = 1 + f(\chi+1) - (f+1) \cdot (\chi+1)^{1/2}$$

wherein
f=ratio between moles of ethylene units and moles of propylene units in the copolymer, and $\chi$=(PPP+PPE)/EPE.

The molecular weight of the polymers can be varied by varying the type or the concentration of the catalyst components or using molecular weight regulators such as, for example, hydrogen.

The tacticity of the polymer chain, i.e. the distribution of the relative configuration of the tertiary carbons, is determined by NMR analysis as described by Resconi et al Chem. Rev. 2000, 100, 1253–1345 and reference cited therein.

The polymers of the invention are transformable into shaped articles by conventional material processing, such as molding, extrusion, injection etc. The polymers of the present invention can be used for the preparation of synthetic leather, roofing blends, geomembranes, transparent objects, foam beds, as additive for bitumen or as polymer support for pigments and/or colors in masterbatches.

EXAMPLES

General Procedures

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. n-BuLi (Aldrich) was used as received.

The proton and carbon spectra of ligands and metallocenes were obtained using a Bruker DPX 200 spectrometer operating in the Fourier transform mode at room temperature at 200.13 MHz and 50.32 MHz respectively. The samples were dissolved in $CDCl_3$, $CD_2Cl_2$ or $C_6D_6$. As reference the residual peak of $CHCl_3$ or $CHDCl_2$ or $C_6HD_5$ in the $^1H$ spectra (7.25 ppm, 5.35 ppm and 7.15 ppm, respectively) and the peak of the solvent in the $^{13}C$ spectra (77.00 ppm for $CDCl_3$) were used. Proton spectra were acquired with a 15° pulse and 2 seconds of delay between pulses; 32 transients were stored for each spectrum. The carbon spectra were acquired with a 45° pulse and 6 seconds of delay between pulses; about 512 transients were stored for each spectrum. $CDCl_3$ (Aldrich, 99.8 atom % D) and $C_6D_6$ (Aldrich, 99.6 atom % D) were stored under molecular sieves (4–5 Å), while $CD_2Cl_2$ (Aldrich, 99.8 atom % D) was used as received.

Preparation of the samples was carried out under nitrogen using standard inert atmosphere techniques.

The proton and carbon spectra of polymers were obtained using a Bruker DPX 400 spectrometer operating in the Fourier transform mode at 120° C. at 400.13 MHz and 100.61 MHz respectively. The samples were dissolved in $C_2D_2Cl_4$. As reference the residual peak of $C_2DHCl_4$ in the $^1H$ spectra (5.95 ppm) and the peak of the mmmm pentad in the $^{13}C$ spectra (21.8 ppm) were used. Proton spectra were acquired with a 450 pulse and 5 seconds of delay between pulses; 256 transients were stored for each spectrum. The carbon spectra were acquired with a 90° pulse and 12 seconds (15 seconds for ethylene based polymers) of delay between pulses and CPD (waltz 16) to remove $^1H$-$^{13}C$ couplings. About 3000 transients were stored for each spectrum.

GC-MS analyses were carried out on a HP 5890—serie 2 gas-chromatograph and a BP 5989B quadrupole mass spectrometer.

The intrinsic viscosity (I.V.) was measured in tetrahydronaphtalene (THN) at 135° C.

The melting points of the polymers ($T_m$) were measured by Differential Scanning Calorimetry (D.S.C.) on an Perkin Elmer DSC-7 instrument, according to the standard method. A weighted sample (5–10 mg) obtained from the polymerization was sealed into aluminum pans and heated at 200° C. with a scanning speed corresponding to 20° C./minute. The sample was kept at 200° C. for 5 minutes to allow a complete melting of all the crystallites. Successively, after cooling to 0° C. with a scanning speed corresponding to 20° C./minute, the peak temperature was taken as crystallization temperature ($T_c$). After standing 5 minutes at 0° C., the sample was heated for the second time at 200° C. with a scanning speed corresponding to 20° C./min. In this second heating run, the peak temperature was taken as the melting temperature ($T_m$) and the area as global melting enthalpy ($\Delta H_f$).

The molecular weight distribution was determined by SEC on a WATERS 200 machine in trichlorobenzene at 135° C.

The following abbreviations are used:
aq.=aqueous
THF=tetrahydrofuran
$Et_2O$=diethyl ether
$CH_2Cl_2$=dichloromethane
DMF=N,N-dimethylformamide
$Me_2SiCl_2$=dichlorodimethylsilane
$Me_3SiCl$=chlorotrimethylsilane
$CuCl_2$=copper (II) chloride
$POCl_3$=phosphorus oxychloride
$B(OMe)_3$=trimethyl borate
$AlCl_3$=aluminium trichloride
n-BuLi=normal butyllithium
Dppf=diphenylphosphinoferrocene
TMEDA=N,N,N',N'-tetramethylethylenediamine
$ZrCl_4$=zirconium tetrachloride
$HfCl_4$=hafnium chloride
$Th_2Cp$=7H-cyclopenta[1,2-b:4,3-b']-dithiophene or 7H-thieno[3',2':3,4]-cyclopenta[b]thiophene
$MeTh_2Cp$=2,5-dimethyl-7H-cyclopenta[1,2-b:4,3-b']-dithiophene
$EtTh_2Cp$=2,5-diethyl-7H-cyclopenta[1,2-b:4,3-b']-dithiophene
$PhTh_2Cp$=2,5-diphenyl-7H-cyclopenta[1,2-b:4,3-b']-dithiophene
AcOH=acetic acid
$(MeO)^2CH_2$=dimethoxymethane Preparation of the Ligand Precursors Synthesis of 3,3'-dibromo-2,2'-dithienylmethanol

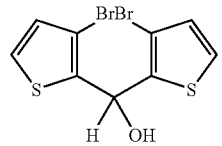

A 2.5 M solution of n-BuLi in hexane (24.30 mL, 60.76 mmol) was added dropwise at −20° C. to a solution of 15.00 g of 2,3-dibromothiophene (Aldrich, 98%, Mw=241.94, d=2.137, 60.76 mmol, n-BuLi:2,3-$Br_2$thiophene=1:1) in 90 mL of ether. The solution turned from pale yellow to yellow. After 1 h stirring at −20° C., 2.53 mL of ethylformate (Aldrich, 97%, Mw=74.08, d=0.917, 30.38 mmol, HCOOEt: 2,3-$Br_2$thiophene=0.5:1) in 30 mL of ether was added dropwise. During the addition the solution turned from yellow to dark yellow. The reaction mixture was kept at −20° C. for 15 min, then allowed to warm to room temperature and stirred for 20 h. The final pale orange suspension was poured at 0° C. into acidic water (1.65 g of $NH_4Cl$ in 75 mL of water), the organic layer was separated out and the water layer extracted with ether (3×25 mL). The organic layers were collected, dried over $Na_2SO_4$ and the solvents were removed under vacuum at 30–35° C. to give an orange oil (9.52 g), which was characterized by GC-MS analysis and $^1H$-NMR spectroscopy.

Purity (by GC-MS)=96.0%. Yield of the pure product=85.0%. $^1H$ NMR (δ, ppm, $CDCl_3$): 7.28 (d, 2H, J=5.29 Hz, CH); 6.95 (d, 2H, J=5.29 Hz, CH); 6.41 (s, 1H, CH); 2.86 (bs, 1H, CH). m/z (%): 356 (23) [M$^+$+4], 354 (42) [M$^+$+2], 352 (22) [M$^+$], 339 (10), 337 (18), 275 (10), 273 (10), 194 (11), 193 (23), 192 (11), 191 (100), 177 (32), 166 (10), 164 (10), 121 (17), 111 (14), 84 (33), 83 (15), 82 (26), 81 (14), 69 (11), 45 (33), 39 (15).

Synthesis of 3,3'-dibromo-2,2'-dithienylmethane

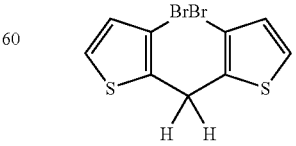

9.45 g of 3,3'-dibromo-2,2'-dithienylmethanol obtained as described above (Nw=354.09, 26.69 mmol considering starting material as 100% pure) were dissolved in 85 mL of dichloromethane in a 250 mL three-necked bottom flask under nitrogen atmosphere and 4.26 mL of triethylsilane (Aldrich, Mw=116.28, d=0.728, 26.69 mmol) were added at 0° C. Then 2.06 mL of CF₃COOH (Aldrich, Mw=114.02, d=1.48, 26.69 mmol) were added dropwise at 0° C. to the stirred mixture. During the addition, the reaction mixture turned from dark orange to dark red. It was kept at 0° C. for 15–20 min, then allowed to warm to room temperature and stirred for 3 h and 30 min at the same temperature. After cooling to 0° C., potassium carbonate (Fluka, 3.69 g, Mw=138.21, 26.69 mmol) was added to the dark red solution, and the resulting mixture was stirred for 30 min at room temperature and finally filtered on G4 fit. The residue on the frit was washed twice with CH₂Cl₂ (2×20 mL) until colourless, while the filtrate was dried under vacuum at 45° C. for 3 h to give a dark red oil (9.07 g), which was analysed by GC-MS analysis and ¹H-NMR spectroscopy. Purity (by GC-MS)=79.9%. Yield of the pure product=80.3%. 3-bromo-2,2'-dithienylmethane (9.9 wt %.) and hexaethyl-disiloxane (6.2 wt %.) were present as by-products. The product was used as such in the next step without further purification.

¹H NMR (Δ, ppm, CDCl₃): 7.16 (d, 2H, J=5.38 Hz, CH); 6.94 (d, 2H, J=5.38 Hz, CH); 427 (s, 2H, CH₂). m/z (%): 340 (28) [M⁺+4], 338 (51) [M⁺+2], 336 (26) [M⁺], 259 (55), 257 (51), 179 (15), 178 (100), 177 (43), 89 (16), 45 (10).

Synthesis of 7H-cyclopenta[1,2-b:4,3-b']dithiophene

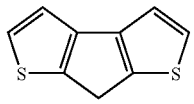

A 2.5 M solution of n-BuLi in hexane (21.30 mL, 53.25 mmol) was added dropwise at −50° C. to a solution of 8.99 g of 3,3'-dibromo-2,2'-dithienylmethane obtained as described above (Mw=338.09, 26.59 mmol) in 75 mL of ether under nitrogen atmosphere in a 250 mL flask. After 1 h stirring at −50° C., the dark brown dilithium suspension was added slowly to a suspension of 7.26 g of CuCl₂ (Aldrich, 98%, Mw=134.45, 52.92 mmol) in 50 mL of Et₂O. The reaction mixture was kept at −50° C. for 30 min, allowed to warm to −20° C. in 2 h 30 min and then allowed to reach 0° C. in few minutes. Aliquots were taken after 30 min at −50° C., at −20° C. and after 1 h at −0° C. to follow the reaction state by GC-MS analysis. It appeared that the CuCl₂ induced coupling reaction starts at −50° C. but proceeds slowly until 0° C. Only 10 wt % of 7H-cyclopenta[2,1-b:4,3-b']dithiophene was formed after 1 h at 0° C. After keeping at 0° C. for 1 h 30 min, the reaction mixture was stirred overnight at room temperature and subsequently poured at 0° C. into 100 mL of an aqueous 2 M HCl solution. The resulting mixture was stirred for 15 min at room temperature, filtered in order to remove the greyish precipitate of Cu₂Cl₂, the ether layer was separated and the aqueous phase extracted with ether. The combined ethereal extracts were washed with HCl 2 M (100 mL), twice with NaHCO₃ aq. and finally with ether. The resulting organic phase (final volume=300 mL) was dried with Na₂SO₄ and the solvents removed in vacuo giving 3.16 g of a dark red oil, which was analysed by GC-MS analysis and ¹H-NMR spectroscopy. The analysis showed the presence of the desired product together with dimers, trimers and tars. The crude product was added of 40 mL of ethanol and stirred for 1 h at room temperature. The yellow-orange extract was concentrated in vacuo at 55° C. for 4 h to give a dark orange oil (1.92 g), which crystallized by standing at 0° C. overnight.

Purity (by GC-MS)=ca. 50%. Yield of the pure product=20.2%. ¹H NMR (δ, ppm, CDCl₃): 7.30 (d, 2H, J=4.93 Hz, CH); 7.13 (d, 2H, J=4.93 Hz, CH); 3.80 (s, 2H, CH₂). m/z (%): 180 (9) [M⁺+2], 179 (16) [M⁺+1], 178 (100) [M⁺], 177 (92), 134 (13), 89 (7), 69 (6), 45 (6).

Synthesis of bis(3,5-dibromo2-thienyl)methanol (or 3,3',5,5'-tetrabromo-2,2'-dithienyl carbinol)

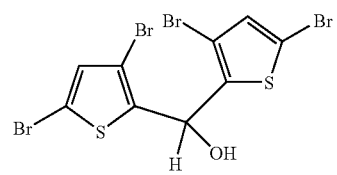

A solution of 31.35 g of 2,3,5-tribromothiophene (Lancaster, 98%, MW=320.84, 95.75 mmol) in 70 mL of ether was cooled to −78° C. and 38.3 mL of a 2.5 M n-BuLi solution in hexane (95.75 mmol) were added dropwise. The resulting mixture was allowed to warm to room temperature, stirred in additional 1 h and then added at 0° C.÷−10° C. to a solution of 3.86 mL of ethylformate (Aldrich, 97%, MW=74.08, d 0.917, 46.35 mmol) in 20 mL of hexane, previously cooled to 0° C.÷−10°0 C. At the end of the addition (~20 min) the reaction mixture was allowed to warm to room temperature and then refluxed for 1 h. The resulting mixture was quenched with 7.5 mL of water, the organic layer was separated out, dried over magnesium sulphate and the solvents evaporated off giving 23.2 g of a pale brown solid, which was analyzed by ¹H NMR, ¹³C NMR, GC-MS. Purity=93.0%. Isolated yield with respect to ethylformate=90.9%.

¹H NMR (δ in ppm, CDCl₃): 6.92 (s, 2H, CH); 6.26 (d, 1H, CH bridge, J=3.2 Hz); 2.73 (d, 1H, OH, J=3.2 Hz) ¹³C NMR (δ in ppm, CDCl₃): 67.38 (CHOH), 108.60, 113.58, 132.18 (CH), 141.10. m/z (%): 512 (67) [M⁺], 494 (50), 433 (54), 352 (53), 335 (35), 285 (43), 269 (100), 242 (19), 162 (33), 81 (27), 39 (13).

Synthesis of 3,3',5,5'-tetrabromo-2,2'-dithienyl-methane

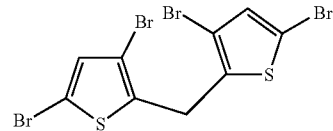

Trifluoroacetic acid (0.25 mL, Aldrich, 99%, MW=114.02, d=1.48, 3.24 mmol) was added at room temperature to a solution of 1.75 g of bis(3,5-dibromo-2-thienyl) methanol (93.0%, MW=511.90, 3.18 mmol) in 15 mL of methylene chloride containing 0.50 mL of triethylsilane (Aldrich, 99%, MW=116.28, d=0.728, 3.13 mmol). The resulting red solution was stirred for 1 h at room temperature, neutralized with solid potassium carbonate (0.4 g, MW=138.21, 2.89 mmol), filtered and evaporated off to give a pale red solid. Yield of crude product=100%.

$^1$H NMR (δ in ppm, CDCl$_3$): 6.94 (s, 2H, CH); 4.17 (s, 2H, CH$_2$). $^{13}$C NMR (δ in ppm, CDCl$_3$): 29.30 (CH$_2$), 109.07, 111.38, 131.98 (CH), 137.22. m/z (%): 496 (71) [M$^+$+4], 417 (76)[M$^+$], 336 (91), 255 (100), 176 (41), 125 (46), 95 (30), 69 (40), 45 (22).

Synthesis of 3,3'-dibromo-5,5'-dimethyl-2,2'-dithienylmethane

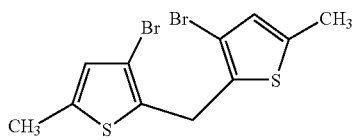

A precooled (−20° C.) 2.5 M solution of n-BuLi in hexane (41.1 mL, 102.75 mmol) was added at −20° C. to a solution of 25.48 g of 3,3',5,5'-tetrabromo-2,2'-dithienylmethane (MW=495.90, 51.38 mmol) in 100 mL of Et$_2$O. After 30 min stirring at −20° C., a precooled (−20° C.) ethereal (10 mL) solution of dimethyl sulphate (Aldrich, 9.72 mL, MW=126.13, d=1.333, 102.75 mmol) was added. The resulting black suspension was stirred for 45 min at −20° C.; the cooling bath was then removed and the flow of nitrogen stopped. A 4 N solution of sodium hydroxide (2.5 mL, 10 mmol) was added and the mixture vigorously stirred for 2 h at room temperature. The resulting reaction mixture was dried by magnesium sulphate, filtered, the residue on the frit washed twice with ether (to recover all the product) and the filtrate was concentrated under reduced pressure at 40° C. for 2 h giving 17.8 g of a brown solid. Purity=87.8% (by GC-MS). Yield of pure product=83.1% (crude yield=94.6%).

$^1$H NMR (δ in ppm, CDCl$_3$): 6.58 (q, 2H, CH, J=1.0 Hz); 4.11 (s, 2H, CH$_2$); 2.39 (d, 6H, CH$_3$, J=1.0 Hz). $^{13}$C NMR (δ in ppm, CDCl$_3$): 15.41 (CH$_3$), 28.88 (CH$_2$), 108.20, 127.57 (CH), 134.10, 138.70. m/z (%): 366 (43) [M$^+$], 287 (47), 206 (100), 191 (21), 173 (14), 103 (10), 59 (20).

Synthesis of 2,5-dimethyl-7H-cyclopenta[1,2-b:4,3-b']dithiophene (or 2,5-dimethyl-7H-thieno[3',2':3,4]cyclopenta[b]thiophene)

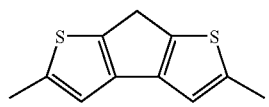

A precooled (−70° C.) 2.5 M n-BuLi solution in hexane (27.1 mL, 67.75 mmol) was added dropwise at −70° C. to a solution of 10.77 g of 3,3'-dibromo-5,5'-dimethyl-2,2'-dithienylmethane NW=366.15, 29.41 mmol) in 60 mL of ether. At the end of the addition, the brown suspension was stirred for additional 30 min at the same temperature. Then a precooled (−70° C.) suspension of 10.28 g of CuCl$_2$ anhydrous (dried at 130° C. for 1 h, MW=134.45, 76.46 mmol) in 35 mL of ether was added quickly. The resulting black suspension was kept at −70° C. for 10 min, at −50° C. for 1 h, at −20° C. for 1 h and at 0° C. for 1 h. Then it was allowed to warm to room temperature and stirred overnight. The colour of the reaction mixture was changed from black to pale brown by increasing the temperature. Aliquots were taken during the reaction for the GC-MS analysis: at −50° C. titre of the desired compound=8.6%, at −20° C. title in the desired compound=20.9%, at 0° C. title in the desired compound=68.8%. The final suspension was poured into 160 mL of an ammonium chloride saturated aqueous solution, the organic layer was separated, the water layer washed with ether, the organic layers collected and dried. 4.79 g of a black solid was obtained. Purity (by GC-MS)=75.9%. Yield of pure product=60.0% (crude yield=79.0%).

$^1$H NMR (δ in ppm, CDCl$_3$): 6.78 (s, 2H, CH); 3.69 (s, 2H, CH$_2$); 2.54 (s, 6H, CH$_3$) $^{13}$C NMR (δ in ppm, CDCl$_3$): 15.96 (CH$_3$), 33.13 (CH$_2$), 116.43 (CH), 140.16, 142.16, 143.67. m/z (%): 206 (100) [M$^+$], 191 (54), 173 (29), 158 (6), 147 (8).

Synthesis of 3,3'-dibromo-5,5'-ditrimethylsilyl-2,2'-dithienylmethane

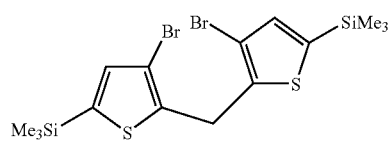

A 2.18 M solution of n-BuLi (65 mL, 141.7 mmol) was added at −70° C. to a solution of 34.8 g of 3,3',5,5'-tetrabromo-2,2'-dithienylmethane (70.2 mmol) in 150 mL of ether. The mixture was stirred for 30 min at the same temperature and 35.5 mL of Me$_3$SiCl (280 mmol) in 65 mL of ether were then added. The resulting mixture was allowed to warm to room temperature, the LiCl was filtered off, and the mother solution was evaporated off to give an oil which represented the target compound in at least 95% purity. To this oil 50 mL of hexane was added and the resulting solution kept at −30° C. for 10 h. Large crystals were isolated, washed with cooled hexane and dried. Yield of recrystallized product 60%. The title compound was characterized by $^1$H-NMR and $^{13}$C-NMR spectroscopy.

Synthesis of 2,5-ditrimethylsilyl-7H-cyclopenta[1,2b:4,3-b']dithiophene (or 2,5-dimethyltrimethylsilyl-7H-thieno[3',2':3,4]cyclopenta[b]thiophene)

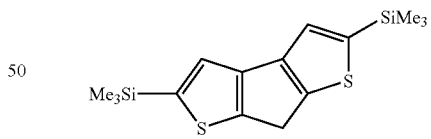

A solution of 0.1 mol of 3,3'-dibromo-5,5'-ditrimethylsilyl-2,2'-dithienylmethane in 200 mL ether was treated with 0.23 mol of n-BuLi at −70° C. At the end of the addition, the reaction mixture was stirred for additional 30 min at the same temperature. Then 0.265 mol of CuCl$_2$ was added quickly. The resulting mixture was allowed to warm to room temperature and stirred overnight. The resulting suspension was poured into water, the organic phase was separated and concentrated. The residue was passed through a column packed with SiO$_2$ using hexane or a hexane/ether mixture as eluent. The resulting solution was evaporated off giving a crystalline or oily-crystalline solid which represented the desired product. Yield 50–60%. The crude product can be further purified in ether by filtration at 0° C. or by recrys-

Synthesis of 3,3'-dibromo-5,5'-dihydroxyboryl-2,2'-dithienylmethane

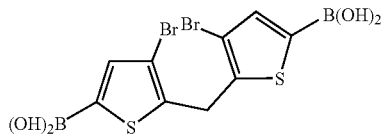

A 1.6 N solution of n-BuLi (100 ml, 160 mmol) was added to a solution of 39.6 g of 3,3',5,5'-tetrabromo-2,2'-dithienylmethane (79.8 mmol) in 150 mL ether at −70° C. The mixture was stirred for 30 min at the same temperature and 23.3 g of B(OMe)$_3$ (220 mmol) in 100 mL of ether were then added. The reaction mixture was allowed to warm to room temperature. The resulting suspension was treated with 100 mL of a 10% aqueous HCl solution, the organic layer was separated, washed twice with 50 mL of a aqueous Na$_2$CO$_3$ 10% solution, evaporated off and dried. The resulting solid which represented the crude di-boronic acid was used in the next step without further purification. The title compound was characterized by $^1$H-NMR and $^{13}$C-NMR spectroscopy.

Synthesis of 3,3'-dibromo-5,5'-diphenyl-2,2'-dithienylmethane

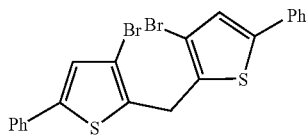

1.81 g of 3,3'-dibromo-5,5'-dihydroxyboryl-2,2'-dithienylmethane (3.76 mmol) 1.40 g of PhI (6.84 mmol), 0.15 g of PdCl$_2$(dppf)$_2$ (0.21 mmol), 120 mL of DMF and 8 mL of Et$_3$N were placed into a reaction flask and this mixture was stirred at 80° C. for 2 h. The resulting mixture was poured into a CH$_2$Cl$_2$/water two-phase system. The organic layer was collected, washed twice with 30 mL of 10% phosphoric acid, then with water and finally evaporated off. The residue was passed through a column packed with SiO$_2$ using hexane/CH$_2$Cl$_2$=1/1 as eluent. The resulting solution was evaporated off, the residue washed with hexane and dried to give 0.6 g of diphenyl derivative. Yield 32%. The title compound was characterized by $^1$H-NMR and $^{13}$C-NMR spectroscopy.

Synthesis of 2,5-diphenyl-7H-cyclopenta[1,2b:4,3b'] dithiophene (or 2,5-diphenyl -7H-thieno[3',2':3,4] cyclopenta[b]thiophene)

Example 30

Synthesis of 1-bromo-2-(3-indenyl)ethane

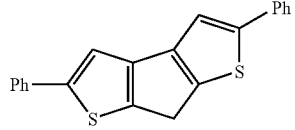

A 1.6 M n-BuLi solution in hexane (100 mL, 0.16 mol) was added at 0° C. to a solution of indene (18.6 g, MW=116.16, 0.16 mol) in 300 mL of ether. The resulting suspension was allowed to warm to room temperature and stirred for 4 h at the same temperature. Then the indenyl lithium suspension was cooled again to −50° C. and added of a solution of 1,2-dibromoethane (0.24 mol, 21 mL) in 50 mL of ether. The reaction mixture was allowed to warm up slowly to room temperature and stirred overnight. Then it was treated with a saturated aqueous solution of NH$_4$Cl. The organic phase was isolated, evaporated off to dryness and distilled in vacuo, b.p. 110° C./0.5 torr. Yield 21.6 g (60%). The title compound was characterized by NMR spectroscopy.

Synthesis of 1,2-(3-indenyl)-7-(2,5-dimethylcyclopenta[1,2-b:4,3-b']-dithiophene)ethane

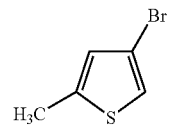

A solution of 2,5-dimethylcyclopenta[1,2-b:4,3-b']-dithiophene (1.03 g, 5 mmol) in 50 mL of THF was treated at −70°C. with a 1.6 M n-BuLi solution in hexane (3.1 mL, 5 mmol). The resulting mixture was stirred for additional 45 min at 0° C., then cooled again to −70° C. and treated with 1-bromo-2-(3-indenyl)ethane (1.12 g, 5 mmol) in 25 mL of THF. The reaction mixture was allowed to warm to room temperature and subsequently treated with a saturated aqueous solution of NH$_4$Cl. The organic phase was isolated and the solvents were removed. The residue was passed through a column packed with silica gel by using hexane as eluent. Yield 1.26 g (72%). The title compound was characterized by NMR spectroscopy.

Synthesis of ethylidene{(1-indenyl)-7-(2,5-dimethylcyclopenta[1,2-b:4,3-b']-dithiophene)}zirconium dichloride C-37

$^1$H NMR (δ in ppm, CDCl$_3$): 6.99 (d, 1H, H$_\alpha$); 6.69 (q, 1H, H$_\beta$); 2.48 (d, 3H, CH$_3$).

Synthesis of 2-methyl-4-formyl-thiophene

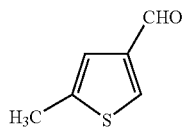

A 1.6 M solution of n-BuLi (164 mL, 0.26 mol) was added at −70° C. to a stirred solution of 44.26 g of 2-methyl-4-bromo-thiophene (0.25 mol) in 300 mL of ether. The resulting solution was kept under stirring at −60° C. to −70° C. for 30 min and then was treated with 27.4 g of dimethylformamide (0.37 mol) in 100 mL of ether. The mixture was allowed to warm to room temperature, then neutralized with 10% aqueous solution of NH$_4$Cl, washed with 10% aqueous solution of H$_3$PO$_4$ and finally with water up to neutral pH. The organic phase was collected, evaporated off and distilled Synthesis of 2,2'-dimethyl-4,4'-dithienylmethane

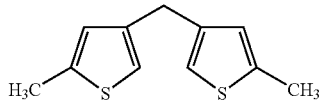

113 mL of 1.6 M n-BuLi solution (0.18 mol) was added to a solution of 31.3 g of 2-methyl-4-bromo-thiophene (0.177 mol) in 150 mL of ether at −70° C. under stirring. The resulting solution was kept under stirring at −60 to −70° C. for 30 min and then was added of 22.3 g of 2-methyl-4-formyl-thiophene (0.177 mol) in 100 mL of ether. The mixture was allowed to warm to room temperature, then neutralized with 10% aqueous solution of $NH_4Cl$ and washed with water. The organic phase was separated and evaporated. The crude bis(2-methyl-4-thienyl)methanol (or 2,2'-dimethyl-4,4'-dithienyl carbinol) was obtained.

A suspension of 35.5 g of $AlCl_3$ (0.266 mol) in 100 mL of ether was added slowly to a suspension of 10 g of $LiAlH_4$ (0.266 mol) in 100 mL of ether. The resulting mixture was treated with the solution of the carbinol (obtained as described above) in 100 mL ether. The reaction mixture was refluxed for additional 1 h, cooled to room temperature and subsequently added of 100 mL of ethyl acetate. Then it was treated with 300 mL of water and 300 mL of ether. The organic phase was collected, washed with water, dried by $MgSO_4$ and evaporated off. The residue was distilled at 90 to 110° C./0.5 mmHg. Yield 23.2 g (63%). The title compound was characterized by $^1$H-NMR spectroscopy.

Synthesis of 2,6-dimethyl-4H-cyclopenta[2,1-b:3,4-b']dithiophene (or 2,6-dimethyl-4H-thieno[3',2':2,3]cyclopenta[b]thiophene)

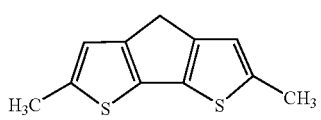

1.04 g of 2,2'-dimethyl-4,4'-dithienylmethane (5 mmol) was dissolved in 30 mL of ether and added of 9 mL of a 1.6 M solution of n-BuLi (14.4 mmol) and of 1.74 g of TMEDA (15 mmol) at −70° C. under stirring. The resulting mixture was allowed to warm to room temperature, stirred for 1 h, then cooled again to −70° C. and treated with 2.7 g of $CuCl_2$ (20 mmol). The resulting reaction mixture was allowed to warm to room temperature and added of 30 mL of water. The organic phase was collected and passed through a column packed with silica gel. The resulting solution was evaporated off to give 0.34 g of the product. Yield 34%. The title compound was characterized by $^1$H-NMR spectroscopy.

Synthesis of 2-ethyl-4-bromo-thiophene

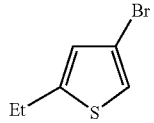

1 mol of acethylthiophene dissolved in 250 mL of $CHCl_3$ was added slowly to a suspension of 2.5 mol of $AlCl_3$ in 1000 mL of $CHCl_3$ under stirring keeping the temperature below 40° C. At the end of the addition, 1.2 mol of $Br_2$ was carefully added dropwise under stirring. The resulting mixture was stirred overnight and then was poured into a mixture of ice (0.5 Kg) and hydrochloric acid (100 mL, 32%). The organic phase was isolated and the solvent was removed. The resulting substance was dissolved in 700 mL of diethyleneglicole and the so-obtained solution was treated with 5.5 mol of 100% hydrazine hydrate. The resulting mixture was refluxed for 30 min. After cooling to room temperature, 2.75 mol of KOH were added. When the gas evolution was ended, the product was distilled. The fraction under the temperature of 150° C. was collected. This fraction represented a mixture of water and product. The organic layer was collected and distilled at 80° C./10 torr. Yield 45%.

$^1$H-NMR (δ, ppm, $CDCl_3$): 7.05 (d, 1H, H5); 6.76 (q, 1H, H3); 2.86 (q, 2H, $CH_2$); 1.33 (t, 3H, $CH_3$).

Synthesis of 3,3'-dibromo-5,5'-diethyl-2,2'-dithienylmethane

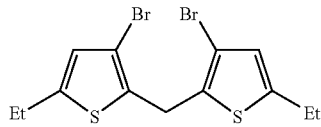

The 2-ethyl-4-bromo-thiophene obtained in the previous step was dissolved into 120 mL of AcOH and was treated with a mixture of 6.1 mL of $H_2SO_4$ and 9.1 mL $(MeO)_2CH_2$. The reaction mixture was stirred overnight, then was washed with 300 mL of water and finally extracted with $CH_2Cl_2$. The organic phase was separated and dried under reduced pressure. The residue was passed through a column packed with $Al_2O_3$ using hexane as eluent. The solvent was removed and the desired product was obtained as yellow oil. Yield 90%.

$^1$H-NMR (δ, ppm, $CDCl_3$): 6.68 (m, 2H, CH); 4.20 (s, 2H, $CH_2$ bridge); 2.80 (q, 4H, $CH_2$); 1.30 (t, 6H, $CH_3$).

Synthesis of 2,5-diethyl-7H-cyclopenta[1,2-b:4,3-b']-dithiophene

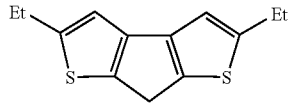

A solution of 0.1 mol of 3,3'-dibromo-5,5'-diethyl-2,2'-dithienylmethane in 200 mL of ether was treated at −70° C.

with 0.23 mol of n-BuLi. At the end of the addition, the mixture was stirred for additional 30 min at the same temperature. The white precipitate of the dilithium salt was formed. Then 0.265 mol of $CuCl_2$ was added quickly at −70° C. The reaction mixture was allowed to warm to room temperature and stirred for 12 h. The resulting suspension was poured into water, the organic phase was separated and concentrated. The residue was recrystallized from ether. Yield 25%.

$^1$H-NMR (δ, ppm, $CDCl_3$): 6.86 (m, 2H, CH); 3.74 (s, 2H, $CH_2$); 2.98 (q, 4H, $CH_2$); 138 (t, 6H, $CH_3$).

Example 1

Synthesis of 2,2-(3-methyl-cyclopentadienyl)-7-(2, 5-dimethyl-cyclopenta [1,2-b:4,3-b']-dithiophene) propane

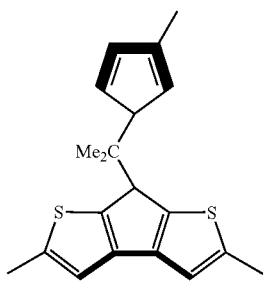

3.13 mL of a 1.6 M solution of n-BuLi (5 mmol) was added at −70° C. to a solution of 1.03 g (5 mmol) of 2,5-dimethyl-7H-cyclopenta[1,2-b:4,3-b']-dithiophene in 20 mL of ether. The resulting mixture was stirred for additional 30 min at 0° C., then cooled again to −70° C. and treated with 0.6 g (5 mmol) of 3,6,6-trimethylfulvene in 10 mL of ether. The reaction mixture was allowed to warm to room temperature and then treated with a saturated aqueous solution of $NH_4Cl$. The organic phase was isolated, dried by $MgSO_4$ and concentrated. The residue was recrystallized from hexane. Yield 1.0 g (62%). The title compound was characterized by $^1$H-NMR spectroscopy.

Synthesis of isopropylidene{(3-methyl-cyclopentadienyl)-7-(2,5-dimethyl-cyclopenta[1,2-b:4,3-b']-dithiophene)}zirconium dichloride C-1

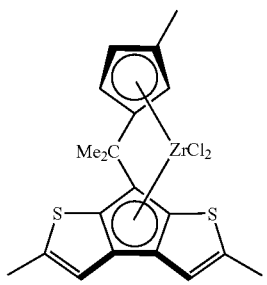

2.3 mL of 1.6 M n-BuLi solution (3.7 mmol) was added at −70° C. to a suspension of 0.6 g (1.85 mmol) of 2,2-(3-methyl-cyclopentadienyl)-7-(2,5-dimethyl-cyclopenta[1,2-b:4,3-b']-dithiophene)propane in 20 mL of ether. The mixture was allowed to warm to 0° C. and then was treated with 0.43 g (1.85 mmol) of $ZrCl_4$. The reaction mixture was refluxed under stirring for 3 h, then the yellow precipitate was filtered, washed twice with ether, dried and finally recrystallized from $CH_2Cl_2$. Yield 0.72 g (80%). The title compound was characterized by $^1$H-NMR spectroscopy.

Example 2

Synthesis of isopropylidene{(3-methyl-cyclopentadienyl)-7-(2,5-dimethyl-cyclopenta[1,2-b:4,3-b']-dithiophene)}hafnium dichloride CH-1

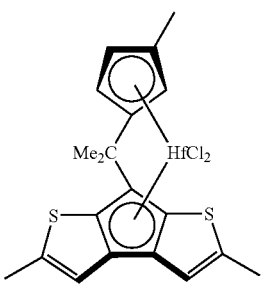

2.5 mL of 1.6 M n-BuLi solution (4.0 mmol) was added at −70° C. to a suspension of 0.65 g (2.0 mmol) of 2,2-(3-methyl-cyclopentadienyl)-7-(2,5-dimethyl-cyclopenta[1,2-b:4,3-b']-dithiophene)propane in 20 mL of ether. The mixture was allowed to warm to 0° C. and then was treated with 0.64 g (2.0 mmol) of $HfCl_4$. The reaction mixture was refluxed under stirring for 3 h, then the yellow precipitate was filtered, washed twice with ether, dried and finally recrystallized from $CH_2Cl_2$. Yield 0.48 g (42%). The title compound was characterized by $^1$H-NMR spectroscopy.

Example 3

Synthesis of 2,2-(2,4-dimethyl-cyclopentadienyl)-7-(2,5-dimethyl-cyclopenta [1,2-b:43b']-dithiophene) propane The same procedure described for the synthesis of 2,2-(3-methyl-cyclopentadienyl)-7-(2,5-dimethyl-cyclopenta [1,2-b:4,3-b']-dithiophene)propane was followed (see below).

Synthesis of isopropylidene{(2,4-dimethyl-cyclopentadienyl)7-(2,5-dimethyl-cyclopenta[1,2-b:4,3-b']-dithiophene)}zirconium dichloride C-12

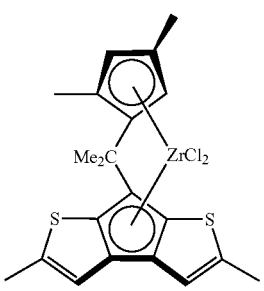

3.13 ml of 1.6 M n-BuLi solution (5.0 mmol) was added at −70° C. to a solution of 1.03 g (5.0 mmol) of 2,5-dimethyl-7H-cyclopenta[1,2-b:4,3-b']dithiophene in 20 mL of ether. The resulting mixture was stirred for additional 30 min at 0° C., then cooled again to −70° C. and treated with 0.67 g (5.0 mmol) of 1,3,6,6-tetramethylfulvene in 10 mL of ether. The reaction mixture was allowed to warm to room temperature and stirred for 8 h. Successively, it was cooled to −30° C. to add 3.13 mL of 1.6 M n-BuLi solution (5.0 mmol). The mixture was then allowed to warm to 0° C. and treated with 1.16 g (5.0 mmol) of ZrCl$_4$. The reaction mixture was refluxed under stirring for 3 h and 10 mL of CH$_2$Cl$_2$ was added at room temperature. The solution was isolated, concentrated and the residue was recrystallized from CH$_2$Cl$_2$/hexane. Yield 0.58 g (23% based on 2,5-dimethyl-7H-cyclopenta[1,2-b:4,3-b']dithiophene).

Example 4

Synthesis of 2,2-(3-isopropyl-cyclopentadienyl-7-(2, 5-dimethyl-cyclopenta [1,2-b:4,3-b']-dithiophene) propane

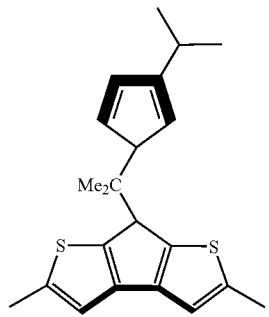

3.13 mL of a 1.6 M solution of n-BuLi (5 mmol) was added at −70° C. to a solution of 1.03 g (5 mmol) of 2,5-dimethyl-7H-cyclopenta[1,2-b:4,3-b']-dithiophene in 20 mL of ether. The resulting mixture was stirred for additional 30 min at 0° C., then cooled again to −70° C. and treated with 0.74 g (5 mmol) of 3-isopropyl-6,6-dimethylfulvene in 10 mL of ether. The reaction mixture was allowed to warm to room temperature and then treated with a saturated aqueous solution of NH$_4$Cl. The organic phase was isolated, dried by MgSO$_4$ and concentrated. The residue was recrystallized from hexane. Yield 0.85 g (48%). The title compound was characterized by $^1$H-NMR spectroscopy.

Synthesis of isopropylidene{(3-isopropyl-cyclopentadienyl)-7-(2,5-dimethyl-cyclopenta[1,2-b:4,3-b']-dithiophene)}zirconium dichloride C-2

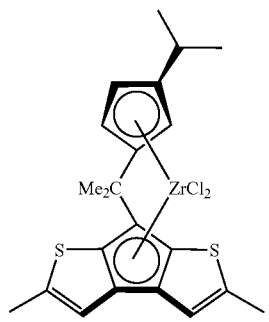

3.75 mL of 1.6 M n-BuLi solution (6.0 mmol) was added at −70° C. to a suspension of 1.06 g (3.0 mmol) of 2,2-(3-isopropyl-cyclopentadienyl)-7-(2,5-dimethyl-cyclopenta[1, 2-b:4,3-b']-dithiophene)propane in 20 mL of ether. The mixture was allowed to warm to 0° C. and then was treated with 0.7 g (3.0 mmol) of ZrCl$_4$. The reaction mixture was refluxed under stirring for 3 h, then the yellow precipitate was filtered, washed twice with ether, dried and finally recrystallized from CH$_2$Cl$_2$. Yield 1.24 g (80%). The title compound was characterized. by $^1$H-NMR spectroscopy.

Example 5

Synthesis of 2,2-(3-isopropyl-cyclopentadienyl)-7-(2,5-ditrimethylsilyl-cyclopenta [1,2-b:4,3-b']-dithiophene)propane The same procedure as described in Example 4 for 2,2-(3-isopropyl-cyclopentadienyl)-7-(2,5-dimethyl-cyclopenta[1,2-b:4,3-b']-dithiophene)propane was followed excepting that 2,5-ditrimethylsilyl-7H-cyclopenta[1,2-b:4, 3-b']dithiophene (or 2,5-dimethyltrimethylsilyl-7H-thieno [3',2':3,4]cyclopenta[b]thiophene) was used (see below).

Synthesis of isopropylidene{(3-isopropyl-cyclopentadienyl)-7-(2,5-ditrimethylsilyl-cyclopenta[1,2-b:4, 3-b']-dithiophene)}zirconium dichloride C-7

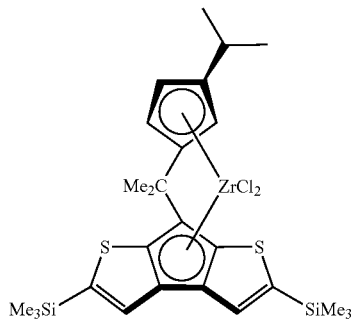

3.05 mL of 1.6 M n-BuLi solution (4.9 mmol) was added at −70° C. to a solution of 1.57 g (4.86 mmol) of 2,5-ditrimethylsilyl-7H-cyclopenta[1,2-b:4,3-b']dithiophene in 20 mL ether. The resulting mixture was stirred for additional 30 min at 0° C., then cooled again to −70° C. and treated with 0.72 g (4.9 mmol) of 3-isopropyl-6,6-dimethylfulvene in 10 mL of ether. The reaction mixture was allowed to warm to room temperature and stirred for 4 h. Successively, it was cooled to −30° C. to add 3.05 mL of 1.6 M n-BuLi solution (4.9 mmol). The mixture was allowed to warm to 0° C. and treated with 1.14 g (4.9 mmol) of ZrCl$_4$. The resulting reaction mixture was refluxed under stirring for 3 h, then the solution was isolated and concentrated. The residue was recrystallized from pentane. Yield 0.23 g (7.4% based on 2,5-ditrimethylsilyl-7H-cyclopenta[1,2-b:4,3-b'] dithiophene). The title compound was characterized by $^1$H-NMR spectroscopy.

Example 6

Synthesis of 2,2-(3-isopropyl-cyclopentadienyl)-4-(2,6-dimethyl-cyclopenta[2,1-b:394-b']dithiophene) propane The same procedure as described in Example 4 was followed, excepting that 2,6-dimethyl-4H-cyclopenta[2,1-b: 3,4-b']dithiophene was used (see below).

Synthesis of isopropylidene{(3-isopropyl-cyclopentadienyl)-4-(2,6-dimethyl-cyclopenta[2,1-b:3,4-b']-dithiophene)}zirconium dichloride C-8

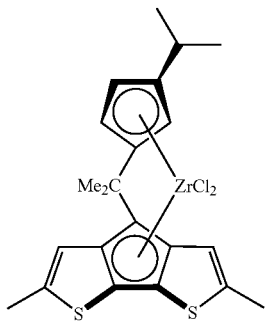

3.13 mL of 1.6 M n-BuLi solution (5.0 mmol) was added at −70° C. to a solution of 1.03 g (5.0 mmol) of 2,6-dimethyl-4H-cyclopenta[2,1-b:3,4-b']dithiophene in 20 mL of ether. The resulting mixture was stirred for additional 30 min at 0° C., then cooled again to −70° C. and treated with 0.74 g (5.0 mmol) of 3-isopropyl-6,6-dimethylfulvene in 10 mL of ether. The mixture was allowed to warm to room temperature and stirred for 4 h. Successively, it was cooled to −30° C. to add 3.13 mL of 1.6 M n-BuLi solution (5.0 mmol). The reaction mixture was allowed to warm to 0° C. and treated with 1.16 g (5.0 mmol) of $ZrCl_4$. The resulting reaction mixture was refluxed under stirring for 3 h and subsequently 30 mL of $CH_2Cl_2$ was added at room temperature. The solution was isolated and concentrated. The residue was recrystallized from $CH_2Cl_2$/hexane. Yield 0.87 g (34% based on 2,6-dimethyl-4H-cyclopenta[2,1-b:3,4-b'] dithiophene). The title compound was characterized by $^1$H-NMR spectroscopy.

Example 7

Synthesis of 2,2-(3-tert-butyl-cyclopentadienyl)-7-(2,5-dimethyl-cyclopenta [1,2-b:4,3-b']-dithiophene)propane

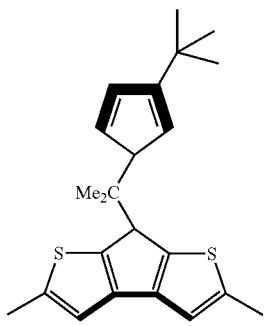

3.13 mL of a 1.6 M solution of n-BuLi (5 mmol) was added at −70° C. to a solution of 1.03 g (5 mmol) of 2,5-dimethyl-7H-cyclopenta[1,2-b:4,3-b']-dithiophene in 20 mL of ether. The resulting mixture was stirred for additional 30 min at 0° C., then cooled again to −70° C. and treated with 0.81 g (5 mmol) of 3-tert-butyl-6,6-dimethylfulvene in 10 mL of ether. The reaction mixture was allowed to warm to room temperature and then treated with a saturated aqueous solution of $NH_4Cl$. The organic phase was isolated, dried by $MgSO_4$ and concentrated. The residue was recrystallized from hexane. Yield 0.94 g (51%). The title compound was characterized by $^1$H-NMR spectroscopy.

Synthesis of isopropylidene{(3-tert-butyl-cyclopentadienyl)-7-(2,5-dimethyl-cyclopenta[1,2-b:4,3-b']-dithiophene)}zirconium dichloride C-3

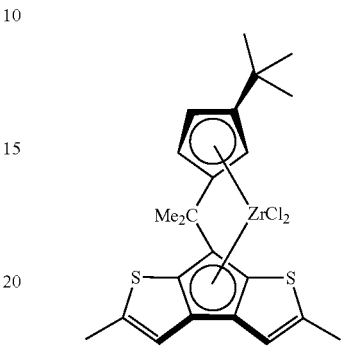

3.75 mL of 1.6 M n-BuLi solution (6.0 mmol) was added at −70° C. to a suspension of 1.11 g (3.0 mmol) of 2,2-(3-tert-butyl-cyclopentadienyl)-7-(2,5-dimethyl-cyclopenta[1,2-b:4,3-b']-dithiophene)propane in 20 mL of ether. The mixture was allowed to warm to 0° C. and treated with 0.7 g (3.0 mmol) of $ZrCl_4$. The reaction mixture was refluxed under stirring for 3 h, then the yellow precipitate was filtered, washed twice with ether, dried and finally recrystallized from $CH_2Cl_2$. Yield 1.27 g (80%). The title compound was characterized by $^1$H-NMR spectroscopy.

Example 8

Synthesis of 2,2(3-isopropyl-cyclopentadienyl)-7-(cyclopenta [1,2-b:4,3-b']-dithiophene)propane

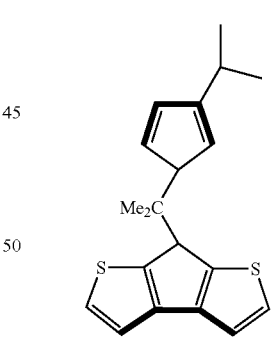

3.13 mL of 1.6 M solution of n-BuLi (5 mmol) was added to a solution of 0.89 g (5 mmol) of 7H-cyclopenta[1,2-b:4,3-b']dithiophene in 20 mL of THF at −70° C. The resulting mixture was stirred for additional 30 min at 0° C., then cooled again to −70° C. and treated with 0.74 g (5 mmol) of 3-isopropyl-6,6-dimethylfulvene in 10 mL of ether. The reaction mixture was allowed to warm to room temperature and then treated with a saturated aqueous solution of $NH_4Cl$. The organic phase was isolated, dried by $MgSO_4$ and concentrated. The residue was passed through a column packed with silica gel using hexane as eluent ($R_f$=0.8). Yield 1.05 g(64%). The title compound was characterized by $^1$H-NMR spectroscopy.

Synthesis of isopropylidene(3-isopropyl-cyclopentadienyl)-7-(cyclopenta[1,2-b:4,3-b']-dithiophene) zirconium dichloride C-16

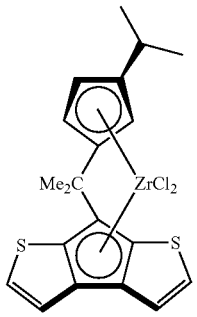

A solution of 1.05 g (3.22 mmol) of 2,2-(3-isopropyl-cyclopentadienyl)-7-(cyclopenta [1,2-b:4,3-b']-dithiophene) propane in a mixture of 10 mL of ether and 60 mL of hexane was treated at −70° C. with 4.1 mL (6.6 mmol) of a 1.6 M n-BuLi solution. The mixture was allowed to warm to 0° C. and treated with 0.75 g (3.2 mmol) of ZrCl$_4$. The resulting reaction mixture was refluxed under stirring for 3 h, then the yellow precipitate was filtered, washed twice with hexane, dried and finally recrystallized from CH$_2$Cl$_2$/hexane. Yield 0.32 g (21%). The title compound was characterized by $^1$H-NMR spectroscopy.

Example 9

Synthesis of isopropylidene{(cyclopentadienyl)-7-(cyclopenta[1,2-b:4,3-b']-dithiophene)}zirconium dichloride C-0

It was carried out as described in the Example 6 of WO 98/22486.

Example 10

Synthesis of chloro(1-indenyl)dimethylsilane

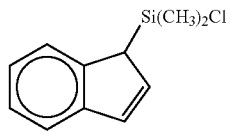

37.5 mL of a 2.5 M solution of n-BuLi in hexane (93.75 mmol, n-BuLi:indene=1.1:1) was added dropwise to a solution of indene purity 90%, 11 g, 85.23 mmol) in 60 mL of Et$_2$O, previously cooled to −78° C. At the end of the addition, the yellow slurry was allowed to reach room temperature and stirred for 4 hours to give an orange solution. The solvents were evaporated off under reduced pressure to give a yellow solid, which was taken up in 75 mL of hexane; the milky suspension was stirred for few minutes and the lithium salt of indene (white precipitate) was filtered and washed with hexane (3×20 mL). The solid was again slurried in hexane (40 mL) and added to a stirred solution of Me$_2$SiCl$_2$ (15.5 mL, 127.84 mmol, Me$_2$SiCl$_2$/IndLi=1.5:1) in 50 mL of hexane, previously cooled to −78° C. At the end of the addition, the mixture was allowed to reach room temperature and stirred overnight. The suspension was then filtered, and the filtrate brought to dryness in vacuum to yield a pale yellow oil (16.5 g) of (1-Ind)SiMe$_2$Cl free from its vinylic isomer (yield 89%).

$^1$H NMR (□ in ppm, CDCl$_3$): 0.21 (s, 3H, Si—CH$_3$), 0.26 (s, 3H, Si—CH$_3$), 3.77 (bs, 1H, Cp-H), 6.68 (dd, 1H, Cp-H), 7.03 (dd, 1H, Cp-H), 7.19–7.36 (m, 2H, Ar), 7.48–7.52 (m, 1H, Ar), 7.57–7.61 (m, 1H, Ar).

Synthesis of (1-indenyl)-7-(2,5-dimethyl-cyclopenta[1,2-b:4,3-b']-dithiophene) dimethylsilane

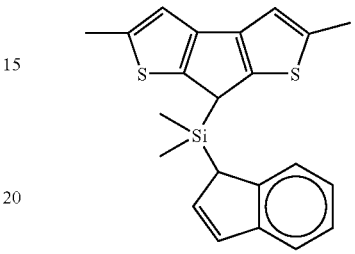

A 2.5 M solution of n-BuLi in hexane (4.80 mL, 12.00 mmol) was added at −20° C. to a suspension of 2.25 g of 2,5-dimethyl-7H-cyclopenta[1,2-b:4,3-b']-dithiophene (Mw=206.32, 10.90 mmol, n-BuLi: MeTh$_2$Cp=1.1:1) in 50 mL of ether. The resulting mixture was stirred for additional 1 h at 0° C. with final formation of a dark brown suspension. This suspension was cooled again to −20° C. and added of a solution of 2.20 g of chloro(1-indenyl)dimethylsilane (Mw=208.76, 10.54 mmol, IndSiMe$_2$Cl:MeTh$_2$Cp=1:1) in 10 mL of ether. The reaction mixture was then allowed to warm to room temperature and stirred for 2 h. The final dark suspension (almost black) was concentrated under vacuum and the residue was extracted with 50 mL of toluene. The extract was dried under vacuum to give 4.06 g of a brown product, which was characterized by $^1$H-NM spectroscopy. The $^1$H-NM analysis showed the presence of the desired ligand (78.5 wt %) together with 15.1 wt % of starting IndSiMe$_2$Cl and 6.4 wt % of toluene. The ligand was used as such in the next step without further purification.

Yield of the pure product=79.9%. $^1$H NMR (δ, ppm, CDCl$_3$): −0.39 (s, 3H, Si—CH$_3$); −0.20 (s, 3H, Si—CH$_3$); 2.57 (s, 6H, CH$_3$); 3.82 (t, 1H, CH, J=1.85 Hz); 3.89 (s, 1H, CH); 6.45 (dd, 1H, CH, J=5.33 Hz, J=1.85 Hz); 6.77–7.52 (m, 7H, Ar).

Synthesis of dimethylsilyl{(1-indenyl)-7-(2,5-dimethyl-cyclopenta[1,2-b:4,3-b']-dithiophene)}zirconium dichloride C-10

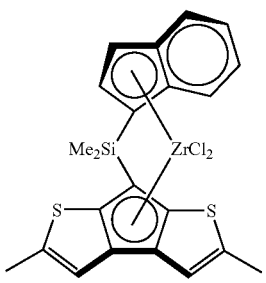

A 2.5 M solution of n-BuLi in hexane (9.00 mL, 22.50 mmol) was added at −20° C. to a solution of 4.06 g of (1-indenyl)-7-(2,5-dimethyl-cyclopenta[1,2-b:4,3-b']- dithiophene)dimethylsilane (Mw=378.64, 10.72 mmol, n-BuLi:ligand=2:1 considering the ligand 100% pure) in 50 mL of ether. The resulting mixture was stirred for additional 1 h at 0° C. with final formation of a dark brown suspension. This suspension was cooled again at −20° C. and added of a suspension of 2.50 g of ZrCl$_4$ (Mw=233.03, 10.72 mmol, ZrCl$_4$:ligand=1:1 considering the ligand 100% pure) in 50 mL of pentane, previously cooled to −20° C. The reaction mixture was kept at −20° C. for 20 min, then allowed to warm to room temperature and stirred for 2 h. The final orange-brown suspension was evaporated off under vacuum and the residue extracted with 50 mL of toluene. The extract was eliminated, while the insoluble in toluene was washed with ether to give an orange powder (4.10 g), which resulted to be the desired catalyst by $^1$H-NMR An aliquot of this powder (1.50 g) was washed very quickly with EtOH (10 mL) and subsequently with Et$_2$O. After drying 0.90 g of pure catalyst as orange powder was recovered. Yield of the crude product (with LiCl)=71.0%.

$^1$H NMR (δ, ppm, CD$_2$Cl$_2$): 1.01 (s, 3H, Si—CH$_3$); 1.29 (s, 3H, Si—CH$_3$); 2.46 (d, 3H, CH$_3$, J=1.17 Hz); 2.58 (d, 3H, CH$_3$, J=1.17 Hz); 6.07 (d, 1H, CH, J=3.28 Hz); 6.70 (q, 1H, CH, J=1.17 Hz); 6.85 (q, 1H, CH, J=1.17 Hz); 6.90–7.64 (m, 5H, Ar).

Example 11

Synthesis of chloro(2-methyl-1-indenyl)dimethylsilane

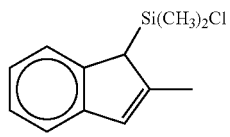

A 2.5 M n-BuLi solution in hexane (22.1 mL, 55.25 mmol, n-BuLi:2-Me-indene=1.1:1) was added dropwise to a solution of 6.54 g of 2-methylindene (Boulder Scientific Company 419-0128, MW=130.19, 50.23 mmol) in 70 mL of Et$_2$O, previously cooled to −20° C. At the end of the addition, the mixture was kept at −20° C. for 15 min, then allowed to warm to room temperature and stirred overnight. The solvents were evaporated off under reduced pressure to give a pale orange solid, which was taken up in 50 mL of hexane; the suspension was stirred for 10 minutes at room temperature and filtered. The lithium salt of 2-methylindene on the filter was washed with hexane (2×10 mL) and dried. The solid was again slurried in 70 mL of hexane and added to a stirred solution of Me$_2$SiCl$_2$ (9.1 mL, d=1.064, MW=129.06, 75.02 mmol, Me$_2$SiCl$_2$/2-Me-IndLi=1.5:1) in 60 mL of hexane, previously cooled to □20° C. At the end of the addition, the pale orange slurry was kept at −20° C. for 15 min, then allowed to warm to room temperature and stirred overnight. The final white-pale yellow suspension was filtered and the filtrate brought to dryness in vacuo at 40° C. to yield a yellow-orange oil as product (8.40 g). Yield=75.1%. Purity=89.1%.

$^1$H NMR (δ, ppm, CDCl$_3$): 0.22 (s, 3H, Si—CH$_3$), 0.47 (s, 3H, Si—CH$_3$), 2.36 (m, 3H, CH$_3$), 3.65 (bs, 1H, CH), 6.70 (m, 1H, Cp-H), 7.18–7.56 (m, 4H, Ar). About 6% (by GC-MS) of bis(2-methyl-1-indenyl)dimethylsilane (rac/meso=1.3:1) was also present. m/z (%): 224 (28) [M$^+$+2], 222 (74) [M$^+$], 129 (20), 128 (67), 127 (17), 95 (35), 93 (100).

Alternative Process Without 2-Me-1-IndLi$^+$ Salt Isolation

A 2.5 M n-BuLi solution in hexane (23.6 mL, 59.00 mmol, n-BuLi:2-Me-indene=1:1) was added dropwise to a solution of 7.87 g of 2-methylindene (B3Boulder Scientific Company 419-0128, MW=130.19, 97.6%, 59.00 mmol) in 50 mL of Et$_2$O, previously cooled to 0° C. At the end of the addition, the mixture was kept at 0° C. for 15 min, then allowed to warm to room temperature and stirred for 2 h with final formation of a pale yellow suspension. It was cooled again to 0° C. and added dropwise of Me$_2$SiCl$_2$ (7.86 mL, d=1.064, MW=129.06, 64.80 mmol, Me$_2$SiCl$_2$/2-Me-IndLi=1.1:1). At the end of the addition, the reaction mixture was allowed to warm to room temperature and stirred overnight. The final white-pale yellow suspension was concentrated in vacuo and the residue extracted with 30 mL of toluene. The extract was brought to dryness in vacuo at 40° C. to yield a orange oil as product (10.41 g).

Yield=79.2%. Purity=83.6%. Traces of starting 2-methylindene and 9.8% of bis(2-methyl-1-indenyl)dimethylsilane (by GC-MS) were also present. m/z for bis(2-methyl-1-indenyl)dimethylsilane (%): 316 (21) [M$^+$], 187 (100), 159 (24), 128 (18), 59 (57).

Synthesis of (2-methyl-I-indenyl)-7-(2,5-dimethyl-cyclopenta[1,2-b:4,3-b']-dithiophene) dimethylsilane

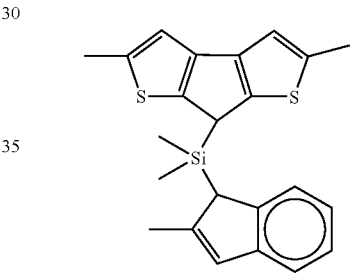

A 2.5 M solution of n-BuLi in hexane (4.15 mL, 10.37 mmol) was added at −20° C. to a solution of 2.13 g of 2,5-dimethyl-7H-cyclopenta[1,2-b:4,3-b']-dithiophene (Mw 206.32, 87.9% by GC-MS, 9.07 mmol, n-BuLi:MeTh$_2$Cp=1.1:1) in 20 mL of ether. The resulting mixture was stirred for additional 1 h at 0° C. with final formation of a dark brown solution. This solution was cooled again to −20° C. and added of a solution of 2.03 g of chloro(2-methyl-1-indenyl)dimethylsilane 9.10 mmol, (2-Me-1-Ind)SiMe$_2$Cl:MeTh$_2$Cp=1:1) in 3 mL of ether. The reaction mixture was then allowed to warm to room temperature and stirred for 2 h. The final dark solution (almost black) was concentrated under vacuum and the sticky residue was extracted with 50 mL of toluene. The extract was dried under vacuum to give 3.93 g of a brown sticky product, which was characterized by GC-MS analysis and $^1$H-NMR spectroscopy. The $^1$H-NMR analysis showed the presence of the desired ligand together with 10 wt % of toluene.

Purity (by GC-MS)=90.4%. Yield of the pure product=89.9%. $^1$H NMR (δ, ppm, CDCl$_3$): −0.37 (s, 6H, Si—CH$_3$); 2.26 (d, 3H, CH$_3$, J=0.8 Hz); 2.56 (dd, 3H, CH$_3$, J=1.1 Hz, J=0.6 Hz ); 2.58 (dd, 3H, CH$_3$, J=1.1 Hz, J=0.6 Hz); 3.88 (bs, 1H, CH); 4.04 (s, 1H, CH); 6.65–6.66 (m, 1H, CH); 6.87 (q, 1H, CH, J=1.1 Hz); 6.89 (q, 1H, CH, J=1.1 Hz); 7.10–7.50 (m, 4H, Ar). m/z (%): 393 (13) [M$^+$+1], 392 (40) [M$^+$], 263 (100), 235 (18), 187 (44), 159 (15), 59 (13).

Synthesis of dimethylsilyl{(2-methyl-1-indenyl)-7-(2,5-dimethyl-cyclopenta[1,2-b:4,3-b']-dithiophene)} zirconium dichloride C-20

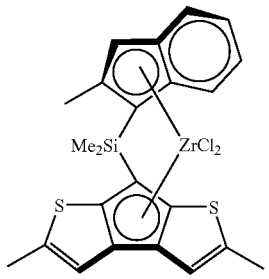

A 2.5 M solution of n-BuLi in hexane (7.20 mL, 18.00 mmol) was added at −20° C. to a solution of 3.93 g of (2-methyl-1-indenyl)-7-(2,5-dimethyl-cyclopenta[1,2-b:4,3-b']-dithiophene)dimethylsilane (Mw=392.66, 90.4% by GC-MS, 8.15 mmol, n-BuLi:ligand=2:1 considering the ligand 90.4% pure) in 30 mL of ether. The resulting mixture was stirred for additional 1 h at 0° C. and 30 min at room temperature with final formation of a dark brown suspension. This suspension was cooled again at −20° C. and added of a suspension of 1.91 g of ZrCl$_4$ (Mw=233.03, 8.20 mmol, ZrCl$_4$:ligand=1:1 considering the ligand 90.4% pure) in 50 mL of pentane, previously cooled to −20° C. The reaction mixture was kept at −20° C. for 1 h, then allowed to warm to room temperature and stirred overnight. The final orange-pale brown suspension was evaporated off under vacuum and the residue washed with ether to give an orange powder (5.32 g), which was analysed by $^1$H-NMR in CD$_2$Cl$_2$. The $^1$H-NMR analysis showed the presence of the desired catalyst together with an adduct of coordination not identified probably ZrCl$_4$(Et$_2$O)$_2$ or LiCl(Et$_2$O)). The powder was washed very quickly with 15 mL of HCl 4N, then with water (30 mL), subsequently with EtOH (20 mL) and finally with Et$_2$O. After drying 3.50 g of pure catalyst as orange powder was recovered. Yield of the pure product=77.7%.

$^1$H NMR (δ, ppm, CD$_2$Cl$_2$): 1.20 (s, 3H, Si—CH$_3$); 1.35 (s, 3H, Si—CH$_3$); 2.39 (d, 3H, CH$_3$,J=0.59); 2.45 (d, 3H, CH$_3$, J=1.2 Hz); 2.62 (d, 3H, CH$_3$, J=1.2 Hz); 6.66 (q, 1H, CH, J=1.2 Hz); 6.81 (bs, 1H, CH); 6.87 (ddd, 1H, CH, J=0.98 Hz, J=6.65 Hz, J=9.0 Hz); 7.21 (ddd, 1H, CH, J=0.98 Hz, J=6.65 Hz, J=8.61 Hz); 7.45 (dt, 1H, CH, J=0.98, Hz J=8.61 Hz); 7.73 (dq, 1H, CH, J=0.98 Hz, J=9.0 Hz).

Example 12

Synthesis of chloro(2-methyl-4-phenyl-1-indenyl)dimethylsilane

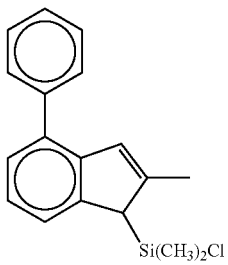

A 2.5 M solution of n-BuLi in hexane (4.85 mL, 12.12 mmol) was added at 0° C. to a solution of 2.50 g of 2-methyl-4-phenyl-indene (Boulder Scientific Company, Mw=206.29, 12.12 mmol, n-BuLi:2-Me-4-Ph-Ind=1:1) in 30 mL of ether. The resulting mixture was stirred for additional 2 h at room temperature with final formation of an orange solution. This solution was cooled again to 0° C. and added slowly of a solution of 1.58 mL of dichlorodimethylsilane (Aldrich, Mw=129.06, d=1.064, 13.03 mmol, Me$_2$SiCl$_2$:2-Me-4-Ph-Ind=1.08:1) in 20 mL of ether. The reaction mixture was then allowed to warm to room temperature and stirred for 1 h. The final straw yellow suspension was concentrated under vacuum and the residue was extracted with 50 mL of toluene. The extract was dried under vacuum to give 3.36 g of a straw yellow solid, which was characterized by GC-MS analysis and $^1$H-NMR spectroscopy. Yield=92.8%.

$^1$H NMR (δ, ppm, CDCl$_3$): 0.24 (s, 3H, Si—CH$_3$); 0.48 (s, 3H, Si—CH$_3$); 2.31 (d, 3H, CH$_3$,J=0.78 Hz); 3.70 (bs, 1H, CH); 6.85 (m, 1H, CH, J=0.78 Hz); 7.19–7.59 (m, 8H, Ar). m/z (%): 300 (26) [M$^+$+2], 299 (18) [M$^+$+1], 298 (72) [M$^+$]; 205 (23), 204 (45), 203 (28), 202 (32), 189 (15), 165 (13), 95 (35), 93 (100).

Synthesis of (2-methyl-4-phenyl-1-indenyl)-7-(2,5-dimethyl-cyclopenta[1,2-b:4,3-b']-dithiophene)dimethylsilane

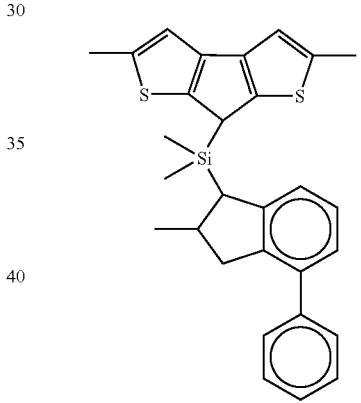

A 2.5 M solution of n-BuLi in hexane (2.72 mL, 6.80 mmol) was added at −20° C. to a solution of 1.40 g of 2,5-dimethyl-7H-cyclopenta[1,2-b:4,3-b']-dithiophene (Mw=206.32, 90.7%, 6.15 mmol, n-BuLi:MeTh$_2$Cp=1.1:1) in 30 mL of ether. The resulting mixture was stirred for additional 1 h at 0° C. with final formation of a dark brown suspension. This suspension was cooled again to −20° C. and added slowly of a solution of 1.90 g of chloro(2-methyl-4-phenyl-1-indenyl)dimethylsilane (Mw=298.89, 6.37 mmol, (2-Me-4-Ph-1-Ind)SiMe$_2$Cl:MeTh$_2$Cp=1.04:1) in 20 mL of ether. The reaction mixture was then allowed to warm to room temperature and stirred for 2 h. The final dark solution (almost black) was concentrated under vacuum and the residue extracted with 50 mL of toluene to give an oily product, which was treated at 30° C. under stirring with 30 mL of pentane. After 15 min stirring a powdery solid was formed and isolated by filtration. After drying in vacuo, 2.03 g of a brown product was recovered.

Purity (by GC-MS)=83.8%. Yield of the pure product=59.0%. $^1$H NMR (δ, ppm, CDCl$_3$): −0.35 (s, 3H, Si—CH$_3$); −0.32 (s, 3H, Si—CH$_3$); 2.23 (d, 3H, CH$_3$, J=0.78 Hz); 2.55 (bs, 3H, CH₃); 2.58 (bs, 3H, CH₃); 3.96 (s, 1H, CH); 4.04 (s, 1H, CH); 6.82 (q, 1H, CH, J=0.78 Hz); 6.86 (q, 1H, CH, J=1.17 Hz); 6.88 (q, 1H, CH, J=1.17 Hz); 7.13–7.59 (m, 8H, Ar). m/z (%): 469 (10) [M⁺+1], 468 (24) [M⁺], 264 (28), 263 (100), 248 (14), 247 (21), 235 (20), 205 (13), 203 (16), 190 (10), 59 (14).

Synthesis of dimethylsilyl{(2-methyl-4-phenyl-1-indenyl)-7-(2,5-dimethyl-cyclopenta[1,2-b:4,3-b']-dithiophene)}zirconium dichloride C-28

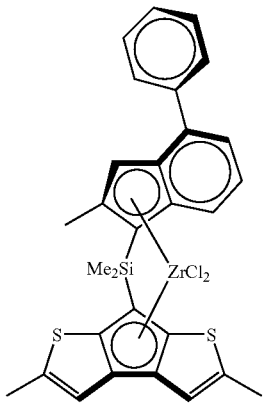

A solution of 2.58 g (5.5 mmol) of (2-methyl-4-phenyl-1-indenyl)-7-(2,5-dimethyl-cyclopenta[1,2-b:4,3-b']-dithiophene)dimethylsilane in 40 mL of ether was treated at −70° C. with 7.0 mL of a 1.6 M n-BuLi solution (11.2 mmol). The reaction mixture was allowed to reach room temperature and stirred for 1 h. The solvent was removed under reduced pressure and the dilithium salt obtained was suspended in hexane. After cooling to −70° C., 1.28 g (5.5 mmol) of ZrCl were added. The reaction mixture was stirred at room temperature overnight, the yellow precipitate was filtered, washed twice with ether, dried and finally recrystallized from CH₂Cl₂. Yield 1.65 g (48%). The title compound was characterized by ¹H NMR spectroscopy.

Example 13

Synthesis of (2-methyl-1-indenyl)-7-(cyclopenta[1,2-b:4,3-b']-dithiophene) dimethylsilane

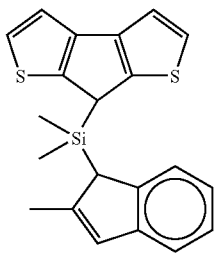

A 2.5 M solution of n-BuLi in hexane (1.50 mL, 3.75 mmol) was added at −20° C. to a solution of 1.29 g of 711-cyclopenta[1,2-b:4,3-b']-dithiophene (Mw=178.28, purity valued by ¹H NMR ca. 50 wt %, 3.62 mmol, n-BuLi:TH₂Cp=1.04:1) in 20 mL of ether. The resulting mixture was stirred for additional 1 h at 0° C. with final formation of a dark brown suspension. This suspension was cooled again to −20° C. and added of a solution of 0.96 g of chloro(2-methyl-1-indenyl)dimethylsilane (83,6% by GC-MS, Mw=222.79, 3.62 mmol, (2-Me-1-Ind)SiMe₂Cl:Th₂Cp=1:1) in 5 mL of ether. The reaction mixture was then allowed to warm to room temperature and stirred for 2 h. The final black suspension was concentrated under vacuum and the stick residue was extracted with 30 mL of toluene to remove the LiCl formed. The extract was dried under vacuum to give 2.26 g of a black oil, which was analysed by ¹H-NMR spectroscopy. Starting chloro(2-methyl-1-indenyl)dimethylsilane, hexaethylsiloxane coming from previous steps and tars were also present as by-products, but attempts to purify the desired ligand failed because of the high solubility of the mixture in apolar solvent as pentane. The crude product was then used as such in the next step without further purification.

¹H NMR (δ, ppm, CDCl₃): −0.36 (s, 3H, Si—CH₃); −0.35 (s, 3H, Si—Cl₃); 2.26 (d, 3H, CH₃, J=0.98 Hz); 3.89 (s, 1H, CH); 4.15 (s, 1H, CH); 6.69–7.52 (m, 9H, Ar).

Synthesis of dimethylsilyl{(2-methyl-1-indenyl)-7-(cyclopenta[1,2-b:4,3-b']-dithiophene)}zirconium dichloride C-36

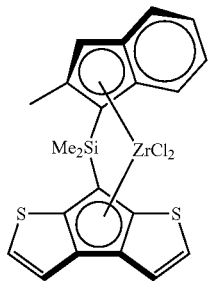

A 2.5 M solution of n-BuLi in hexane (5.00 mL, 12.50 mmol) was added at −20° C. to a solution of 2.26 g of (2-methyl-1-indenyl)-7-(cyclopenta[1,2-b:4,3-b']-dithiophene)dimethylsilane (Mw=364.61, 6.20 mmol, n-BuLi:ligand=2.02:1 considering the ligand 100% pure) in 20 mL of ether. The resulting mixture was stirred for additional 1 h at 0° C. with final formation of a brown suspension. This suspension was cooled again to −20° C. and added of a suspension of 1.44 g of ZrCl₄ (Mw=233.03, 6.20 mmol, ZrCL₄:ligand=1:1 considering the ligand 100% pure) in 30 mL of pentane, previously cooled to −20° C. The reaction mixture was kept at −20° C. for 1 h, then allowed to warm up slowly to room temperature and stirred for 3 h. The final brown suspension was evaporated off under vacuum and the residue extracted with 30 mL of toluene: the extract, containing mainly tars, was eliminated, while the brown residue (3.33 g) was dried and washed with 20 mL of ether. The ¹H-NMR analysis in CD₂Cl₂ showed for the residue from ether the presence of the desired catalyst together with an adduct of coordination not identified probably ZrCl₄(Et₂O)₂ or LiCl(Et₂O)) and few tars. Again the brown powder (2.28 g) was washed very quickly with 20 mL of CH₂Cl₂, then with EtOH (10 mL) and finally with Et₂O (15 mL). After drying 0.44 g of catalyst as pale brown powder was recovered. Yield=13.5%.

¹H NMR (δ, ppm, CD₂Cl₂): 1.25 (s, 3H, Si—CH₃); 1.41 (s, 3H, Si—CH₃); 2.38 (bs, 3H, CH₃); 6.82–7.79 (m, 9H, Ar).

Example 14

Synthesis of chlorodimethyl-(2-phenyl-1-indenyl)silane

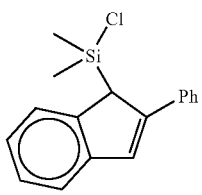

A solution of 0.96 g (5.0 mmol) of 2-phenylindene in 30 mL of Et$_2$O was treated at −70° C. with 3.13 mL (5.0 mmol) of a 1.6 M solution of n-BuLi. After the addition, the mixture was allowed to warm to room temperature and stirred for 50 min. Then it was cooled again to −70° C. and treated with a solution of 0.65 g (5.0 mmol) of Me$_2$SiCl$_2$ in 10 mL of ether. When the addition was completed, the mixture was allowed to reach room temperature and stirred overnight. The resulting reaction mixture was filtered to remove LiCl and the solvent was removed under reduced pressure. The crude product was used in the next step without further purification.

$^1$H-NMR (δ, ppm, C$_6$D$_6$): 7.90–7.10 (m, 9H, CH); 6.95 (s, 1H, CH); 4.15 (s, 1H, CH); −0.02 (s, 3H, Si—CH$_3$); −0.20 (s, 3H, Si—CH$_3$).

Synthesis of dimethylsilyl{(2-phenyl-1-indenyl)-7-(2,5-dimethyl-cyclopenta[1,2-b:4,3-b']-dithiophene)} zirconium dichloride C-31

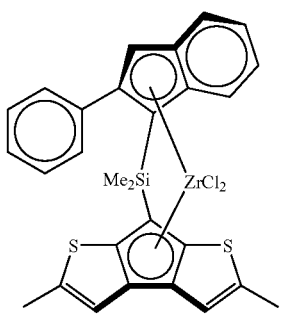

A suspension of 1.03 g (5.0 mmol) of 2,5-dimethyl-7H-cyclopenta[1,2-b:4,3-b']-dithiophene in 30 mL of ether was treated at −70° C. with 3.13 mL of a 1.6 M n-BuLi solution (5.0 mmol). After the addition, the resulting mixture was allowed to warm to room temperature and stirred for additional 50 min at this temperature. Then it was cooled again to −70° C. and added of an etheral solution (10 mL) of chlorodimethyl-(2-phenyl-1-indenyl)silane coming from the previous step. The mixture was allowed to warm to room temperature and stirred overnight. The ligand (2-phenyl-1-indenyl)-7-{(2,5-dimethyl-cyclopenta[1,2-b:4,3-b']-dithiophene)}dimethylsilane was characterized by $^1$H-NMR spectroscopy.

$^1$H-NMR (δ, ppm, CDCl$_3$): 7.70–7.25 (m, 9H, CH); 7.20 (s, 1H, CH); 6.90 (m, 2H, CH); 4.60 (s, 1H, CH); 3.70 (s, 1H, CH); 2.65 (s, 3H, CH$_3$); 2.60 (s, 3H, CH$_3$); −0.44 (s, 3H, Si—CH$_3$); −0.66 (s, 3H, Si—CH$_3$).

The ligand was not isolated: its solution was treated at −70° C. with 7.0 mL of a 1.6 M n-BuLi solution (11.2 mmol). Then the reaction mixture was allowed to reach room temperature and stirred for 1 h. The solvent was removed under reduced pressure and the dilithium salt obtained was suspended in hexane. After cooling to −70° C., 1.28 g (5.5 mmol) of ZrCl$_4$ were added. The reaction mixture was stirred at room temperature overnight, the red precipitate was filtered, washed twice with ether, dried and finally recrystallized from CH$_2$Cl$_2$.

Yield 1.64 g (53% based on Me$_2$Th).

Example 15

Synthesis of (2-methyl-1-indenyl)-7-(2,5-diethyl-cyclopenta[1,2-b:4,3-b']-dithiophene)dimethylsilane

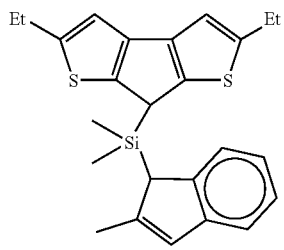

A suspension of 1.17 g (5.0 mmol) of 2,5-diethyl-7H-cyclopenta[1,2-b:4,3-b']-dithiophene in 75 mL of ether was treated at −70° C. with 3.13 mL of a 1.6 M n-BuLi solution (5.0 mmol). After the addition, the mixture was allowed to warm to room temperature and stirred for additional 1 h at this temperature. Then it was cooled again to −70° C. and added of a solution of 1.11 g (5 mmol) of chloro(2-methyl-1-indenyl)dimethylsilane in 10 mL of ether. The resulting mixture was allowed to reach room temperature and stirred overnight. The ligand (2-methyl-1-indenyl)-7-(2,5-diethyl-cyclopenta[1,2-b:4,3-b']-dithiophene)dimethylsilane was not isolated, but used in solution for the catalysts synthesis (see below).

$^1$H-NMR (δ, ppm, CDCl$_3$): 7.55 (d, 1H, CH); 7.44 (d, 1H, CH); 7.28 (m, 1H, CH); 7.15 (m, 1H, CH); 6.98 (m, 1H, CH); 6.96 (m, 1H, CH); 6.70 (m, 1H, CH); 4.10 (s, 1H, CH); 3.94 (s, 1H, CH); 2.98 (m, 4H, CH$_2$); 2.31 (s, 3H, CH$_3$); 1.43 (t, 3H, CH$_3$); 1.41 (t, 3H, CH$_3$); −0.30 (s, 3H, Si—CH$_3$); −0.31 (s, 3H, Si—CH$_3$).

Synthesis of dimethylsilyl{(2-methyl-1-indenyl)-7-(2,5-diethyl-cyclopenta[1,2-b:4,3-b']-dithiophene)} zirconium dichloride C-34

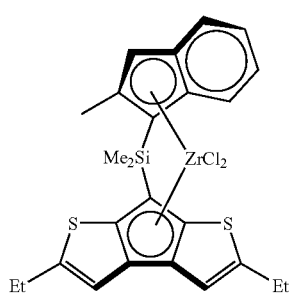

The ligand solution coming from the previous step was treated at −70° C. with 7.0 mL of a 1.6 M n-BuLi solution (11.2 mmol). Then the reaction mixture was allowed to reach room temperature and stirred for 1 h. The solvent was removed under reduced pressure and the dilithium salt so-obtained was suspended in hexane. After cooling to −70° C., 0.75 g (3.2 mmol) of ZrCl₄ were added. The reaction mixture was stirred at room temperature overnight, the yellowish-red precipitate was filtered, washed twice with ether, dried and finally recrystallized from CH₂Cl₂. Yield 1.52 g (52% with respect to Et₂Th).

Example 16

Synthesis of (2-methyl-1-indenyl)-7-(2,5-diphenyl-cyclopenta[1,2-b:4,3-b']-dithiophene)dimethylsilane

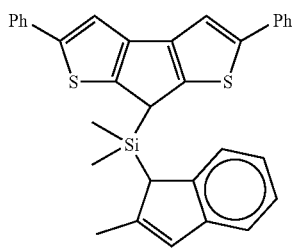

A solution of 1.32 g (4.0 mmol) of 2,5-diphenyl-7H-cyclopenta[1,2-b:4,3-b']-dithiophene in 30 mL of ether was treated at −70° C. with 2.50 mL of a 1.6 M n-BuLi solution (4.0 mmol). After the addition, the mixture was allowed to warm to room temperature and stirred for additional 50 min at this temperature. Then it was cooled again to −70° C. and added of a solution of 0.90 g (4.0 mmol) of chlorodimethyl (2-methyl-1-indenyl)silane in 10 mL of ether. The resulting mixture was allowed to reach room temperature and stirred overnight. The ligand (2-methyl-1-indenyl)-7-(2,5-diphenyl-cyclopenta[1,2-b:4,3-b']-dithiophene)dimethylsilane was not isolated, but used in solution for the catalysts synthesis.

Synthesis of dimethylsilyl{(2-methyl-1-indenyl)-7-(2,5-diphenyl-cyclopenta[1,2-b:4,3-b']-dithiophene)} zirconium dichloride C-35

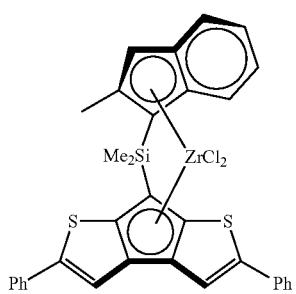

The ligand solution coming from the previous step was treated at −70° C. with 5.6 mL of a 1.6 M n-BuLi solution (9.0 mmol). Then the reaction mixture was allowed to reach room temperature and stirred for additional 1 h After cooling to −70° C., 1.05 g (4.5 mmol) of ZrCl₄ were added. The reaction mixture was stirred at room temperature overnight, then the violet precipitate was filtered, washed twice with ether, dried and finally recrystallized from CH₂Cl₂.
Yield 1.27 g (47% with respect to Ph₂Th).

Example 17

Synthesis of 3,6,6-trimethylfulvene

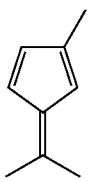

A solution of 2-methyl-1,3-cyclopentadiene (125 g, 1.56 mol) in 1.2 L of ethanol was treated at low temperature with 126 mL (1.72 mol) of acetone and 142 mL (1.72 mol) of pyrrolidine. The resulting solution was kept below room temperature overnight. Then the reaction mixture was neutralized with a 10% aq. solution of H₃PO₄, extracted with hexane (3×150 mL) and washed with water until neutral pH. The organic phase was separated, dried with MgSO₄ and concentrated. The residue was distilled at 70° C./60 mmHg. Yield 112.6 g (60%).
¹H NMR (δ, ppm, CDCl₃): 6.53 (dd, 1H, CH); 6.35 (dd, 1H, CH); 6.20 (m, 1H, CH); 2.17 (s, 3H, CH₃); 2.16 (s, 3H, CH₃); 2.09 (s, 3H, CH₃).

Synthesis of
3-isopropyl-1-methyl-1,3-cyclopentadiene

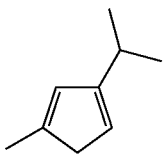

A solution of 24 g (0.2 mol) of 3,6,6-trimethylfulvene in 100 mL of ether was added at 78° C. under argon atmosphere to a solution of 7.59 g (0.2 mol) of lithium aluminium hydride in 200 mL of ether. The reaction mixture was allowed to warm to room temperature, stirred for 2 h and then treated with a 10% aq. solution of NH₄Cl. The organic phase was collected, washed with water, dried with MgSO₄ and concentrated. The residue was distilled at 63° C./50 mmHg. Yield 15.88 g (65%).The desired title compound was characterized by ¹H-NR Synthesis of
1-methyl-3-isopropyl-6,6-dimethylfulvene

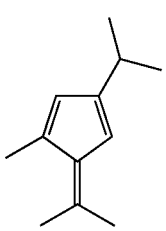

3-isopropyl-1methyl-1,3-cyclopentadiene (39 g, 0.32 mol) was added at low temperature to a suspension of 12.8 g (0.32 mol) of sodium hydroxide in 200 mL of dry THF. After 30 min stirring, the reaction mixture was treated with 23.8 mL (0.32 mol) of acetone. The resulting solution was kept below room temperature overnight. Then the resulting mixture was neutralized with a 10% aq. solution of $H_3PO_4$, extracted with hexane (3×100 mL) and washed with water until neutral pH. The organic phase was separated, dried with $MgSO_4$ and concentrated. The residue was distilled at 80° C./10 mmHg. Yield 25.96 g (50%).

$^1$H NMR (δ, ppm, $CDCl_3$): 6.21 (m, 1H, CH); 6.05 (d, 1H, CH); 2.67 (m, 1H, CH); 2.24 (s, 3H, $CH_3$); 2.21 (s, 3H, $CH_3$); 2.20 (s, 3H, $CH_3$); 1.26 (s, 3H, $CH_3$); 1.28 (s, 3H, $CH_3$).

Synthesis of 2,2-(2-methyl-4-isopropyl-cyclopentadienyl)-7-(2,5-dimethyl-cyclopenta[1,2-b:4,3-b']dithiophene)propane

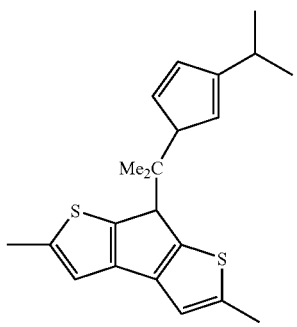

A 1.6 M solution of n-BuLi (6.25 mL, 10 mmol) was added at −70° C. to a suspension of 2.06 g (10 mmol) of 2,5-dimethyl-7H-cyclopenta[1,2-b:4,3-b']-dithiophene in 100 mL of ether. At the end of the addition, the mixture was allowed to warm to room temperature and stirred for additional 50 min at the same temperature. The resulting reaction mixture was treated at −70° C. with a solution of 0.74 g (5 mmol) of 1-methyl-3-isopropyl-6,6-dimethylfulvene, then was allowed to warm to room temperature and stirred overnight. The final mixture was poured into 100 mL of a 10% aq. solution of $NH_4Cl$ and extracted with hexane (2×50 mL). The organic phase was collected, washed with water, dried with $MgSO_4$ and evaporated off. The residue was passed through a column packed with $SiO_2$ by using hexane as eluent. The resulting solution was dried giving the crystalline product. Yield 1.5 g (41% based on starting $MeTh_2Cp$).

Synthesis of isopropilydene{(2-methyl-4-isopropyl-cyclopentadienyl)-7-(2,5-dimethyl-cyclopenta[1,2-b:4,3-b']-dithiophene)}zirconium dichloride C-17

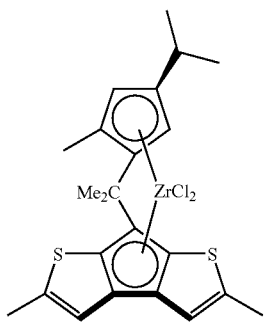

A suspension of 1.11 g (3 mmol) of 2,2-(2-methyl-4-isopropyl-1-cyclopentadienyl)-7-{(2,5-dimethyl-cyclopenta[1,2-b:4,3-b']dithiophene)}propane in 10 mL of ether and 50 mL of hexane was treated at −70° C. with 3.8 mL of a 1.6 M n-BuLi solution (6.1 mmol). After the addition, the reaction mixture was allowed to warm to 0° C. and added of 0.75 g (3.2 mmol) of $ZrCl_4$. The resulting mixture was allowed to reach room temperature and stirred overnight. Then the yellow precipitate obtained was filtered, washed twice with ether, dried and finally recrystallized from $CH_2Cl_2$.

Yield 1.43 g (90%). $^1$H-NMR (δ, ppm, $CD_2Cl_2$): 6.88 (m, 1H, CH); 6.80 (m, 1H, CH); 6.10 (d, 1H, CH); 5.58 (d, 1H, CH); 2.78 (m, 1H, CH); 2.58 (m, 3H, $CH_3$); 2.56 (d, 3H, $CH_3$); 2.40 (s, 3H, $CH_3$); 2.18 (s, 3H, $CH_3$); 1.96 (s, 3H, $CH_3$); 1.14 (d, 3H, $CH_3$); 1.08 (d, 3H, $CH_3$).

Example 18

Synthesis of 1,3-dimethyl-1,3-cyclopentadiene

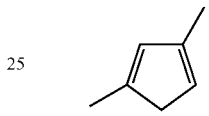

A solution of 25 g (0.26 mol) of 3-methyl-2-cyclopenten-1-one in 100 mL of ether was added at −78° C. under argon atmosphere to a solution of methyl litium in 200 mL of ether, previous prepared from 5.76 g (0.83 mol) of lithium and 26 mL (0.42 mol) of iodomethane. The reaction mixture was stirred for 4 h and then treated with a 10% aq. solution of $NH_4Cl$. The organic phase was collected, washed with water, dried with $MgSO_4$ and concentrated. The residue was distilled at 42° C./100 mmHg. Yield 7.3 g (30%).

$^1$H-NMR (δ, ppm, $CD_3COCD_3$): 5.98 (m, 1H, CH); 5.75 (m, 1H, CH); 2.80 (m, 2H, $CH_2$); 2.02 (d, 3H, $CH_3$); 1.90 (d, 3H, $CH_3$).

The ligand synthesis was carried out by coupling the lithium salt of the $MeTh_2Cp$ precursor with chloro(2,4-dimethylcyclopentadienyl)dimethylsilane, previous prepared from the lithium salt of 1,3-dimethyl-1,3-cyclopentadiene and $Me_2SiCl_2$.

Synthesis of dimethylsilyl{(2,4-dimethyl-cyclopentadienyl)-7-(2,5-dimethyl-cyclopenta[1,2-b:4,3-b']-dithiophene)}zirconium dichloride C-18

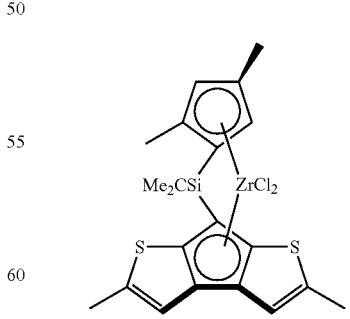

A suspension of 1.07 g (3 mmol) of (2,4-dimethyl-cyclopentadienyl)-7-{(2,5-dimethyl-cyclopenta[1,2-b:4,3-b']dithiophene)}dimethylsilane in 20 mL of ether was treated at −70° C. with 4.1 mL of a 1.6 M n-BuLi solution (6.5 mmol). After the addition, the reaction mixture was allowed to warm to 0° C. and added of 0.75 g (3.2 mmol) of ZrCl$_4$. The resulting mixture was allowed to reach room temperature and stirred overnight. Then the yellow precipitate obtained was filtered, washed twice with ether, dried and finally recrystallyzed from CH$_2$Cl$_2$.

Yield 1.35 g (87%). $^1$H-NMR (δ, ppm, CD$_2$Cl$_2$): 6.93 (m, 1H, CH); 6.87 (m, 1H, CH); 6.80–6.70 (m, 1H, CH); 6.25 (t, 1H, CH); 2.59 (d, 3H, CH$_3$); 2.56 (d, 3H, CH$_3$); 2.18 (s, 3H, CH$_3$); 2.11 (s, 3H, CH$_3$); 1.03 (s, 3H, Si—CH$_3$); 0.84 (s, 3H, Si—CH$_3$).

Example 19

Synthesis of dimethylsilyl{(3-tert-butyl-cyclopentadienyl-7-(2,5-dimethyl-cyclopenta[1,2-b:4,3-b']-dithiophene)}zirconium dichloride C4

The synthesis was carried out by following the same procedure described in the Example 18 by using 3-tert-butyl-1,3-cyclopentadiene instead of 1,3-dimethyl-1,3cyclopentadiene. The product was characterized by NMR spectroscopy.

Example 20

Synthesis of isopropilydene{(tetramethyl-cyclopentadienyl)-7-(2,5-dimethyl-cyclopenta[1,2-b:4,3-b']-dithiophene)}zirconium dichloride C-5

The synthesis was carried out by following the same procedure described in the Example 17 by using 1,2,3,4,6,6-esamethylfulvene instead of 1-methyl-3-isopropyl-6,6-dimethylfulvene. The product was characterized by NMR spectroscopy.

Example 21

Synthesis of dimethylsilyl{(3-trimethylsilyl-cyclopentadienyl)-7-(2,5-dimethyl-cyclopenta[1,2-b:4,3-b']-dithiophene)}

The ligand synthesis was carried out by coupling the lithium salt of the MeTh$_2$Cp precursor with chloro(3-trimethylsilyl-cyclopentadienyl)dimethylsilane, previous prepared from the lithium salt of trimethylsilyl-1,3-cyclopentadiene and Me$_2$SiCl$_2$.

Synthesis of dimethylsilyl{(3-trimethylsilyl-cyclopentadienyl)-7-(2,5-dimethyl-cyclopenta[1,2-b:4,3-b']-dithiophene)}zirconium dichloride C-9

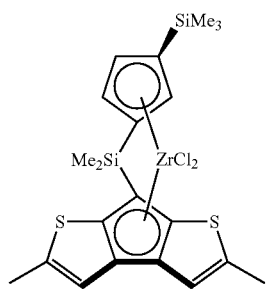

A suspension of 1.20 g (3 mmol) of (3-trimethylsilyl-1-cyclopentadienyl)-7-{(2,5-dimethyl-cyclopenta[1,2-b:4,3-b']dithiophene)}dimethylsilane in 20 mL of ether was treated at −70° C. with 4.1 mL of a 1.6 M n-BuLi solution (6.5 mmol). After the addition, the reaction mixture was allowed to warm to 0° C. and added of 0.75 g (3.2 mmol) of ZrCl$_4$. The resulting mixture was allowed to reach room temperature and stirred overnight Then the yellow precipitate obtained was filtered, washed twice with ether, dried and finally recrystallyzed from CH$_2$Cl$_2$.

Yield 1.17 g (70%). $^1$H-NMR (δ, ppm, CD$_2$Cl$_2$): 6.91 (m, 1H, CH); 6.88 (m, 1H, CH); 6.78 (m, 1H, CH); 6.08 (t, 1H, CH); 5.83 (t, 1H, CH); 2.59 (d, 3H, CH$_3$); 2.57 (d, 3H, CH$_3$); 0.91 (s, 3H, Si—CH$_3$); 0.89 (s, 3H, Si—CH$_3$); 0.20 (s, 9H, Si(CH$_3$)$_3$).

Example 22

Synthesis of 1-methyl-3-phenyl-1,3-cyclopentadiene

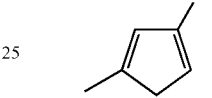

A solution of 25 g (0.26 mol) of 3-methyl-2cyclopenten-1-one in 100 mL of ether was added at −78° C. under argon atmosphere to a solution of phenyl litium in 200 mL of ether, previous prepared from 5.76 g (0.83 mol) of lithium and 44 mL (0.42 mol) of bromobenzene. The reaction mixture was stirred for 4 h and then treated with a 10% aq. solution of NH$_4$Cl. The organic phase was collected, washed with water, dried with MgSO$_4$ and concentrated. The residue was distilled at 54° C./1 mmHg. Yield 24.37 g (60%).

$^1$H-NMR (δ, ppm, CD$_3$COCD$_3$): 7.60–7.10 (m, 5H, CH); 6.80 (d, 1H, CH); 6.00 (m, 1H, CH); 3.00 (s, 2H, CH$_2$); 1.98 (q, 3H, CH$_3$).

Synthesis of 1-methyl-3-phenyl-6,6-dimethylfulvene

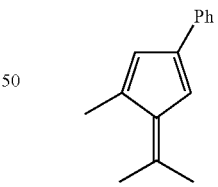

A solution of 1-methyl-3-phenyl-1,3-cyclopentadiene (15.62 g, 0.1 mol) in 100 mL of ethanol was treated at low temperature with 8.6 mL (0.12 mol) of acetone and 9.7 mL (0.12 mol) of pyrrolidine. The resulting solution was kept below room temperature overnight. Then the reaction mixture was neutralized with a 10% aq. solution of H$_3$PO$_4$, extracted with hexane (3×50 mL) and washed with water until neutral pH. The organic phase was separated, dried with MgSO$_4$ and concentrated. The residue was distilled at 85° C./10 mmHg. Yield 5.89 g (30%). The desired title compound was characterized by $^1$H-NMR.

The ligand synthesis was carried out by following the same procedure described in the Example 17, by using 1-methyl-3-phenyl-6,6-dimethylfulvene instead of 1-methyl-3-isopropyl-6,6-dimethylfulvene and 2,5-ditrimethylsilyl-7H-cyclopenta[1,2-b:4,3-b']dithiophene instead of MeTh₂Cp.

Synthesis of isopropilydene{(2methyl-4-phenyl-cyclopentadienyl)7-(2,5-trimethylsilylcyclopenta[1,2-b:4,3-b']-dithiophene)}zirconium dichloride C-14

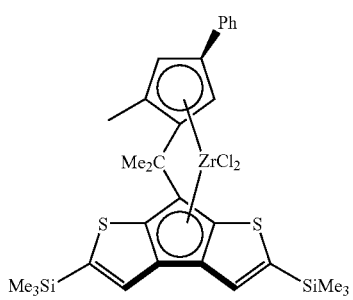

A suspension of 2.0 g (3.85 mmol) of 2,2-(2-methyl-4-phenyl-1-cyclopentadienyl)-7-(2,5-trimethylsilylcyclopenta[1,2-b:4,3-b']-dithiophene)propane in 50 mL of ether was treated at −70° C. with 4.8 mL of a 1.6 M n-BuLi solution (7.71 mmol). After the addition, the reaction mixture was allowed to warm to 0° C. and added of 0.90 g (3.85 mmol) of ZrCl₄. The resulting mixture was allowed to reach room temperature and stirred overnight. Then the brown precipitate obtained was filtered, washed twice with ether, dried and finally recrystallyzed from CH₂Cl₂. Yield 1.82 g (70%).

¹H-NMR (δ, ppm, CD₂Cl₂): 7.34 (s, 2H, CH); 7.32–7.12 (m, 5H, CH); 6.62 (d, 1H, CH); 6.26 (d, 1H, CH); 2.50 (s, 3H, CH₃); 2.30 (s, 3H, CH₃); 2.10 (s, 3H, CH₃); 0.36 (s, 9H, Si(CH₃)₃; 0.32 (s, 9H, Si(CH₃)₃).

Example 23

Synthesis of isopropilydene{(2-methyl-4-phenyl-cyclopentadienyl)-7-(2,5-dimethyl-cyclopenta[1,2-b:4,3-b']-dithiophene)}zirconium dichloride C-11

The synthesis was carried out by following the same procedure described in the Example 22 by using 2,5-dimethyl-cyclopenta[1,2-b:4,3-b']-dithiophene instead of 2,5-trimethylsilylcyclopenta [1,2-b:4,3-b']-dithiophene. The product was characterized by NMR spectroscopy.

Example 24

Synthesis of isopropilydene{(4-phenyl-cyclopentadienyl)-7-(2,5-dimethyl-cyclopenta[1,2-b:4,3-b']-dithiophene)}zirconium dichloride C-19

The synthesis was carried out by following the same procedure described in the Example 22 by using 3-phenyl-6,6-dimethylfulvene instead of 1-methyl-3-phenyl-6,6-dimethylfulvene. The product was characterized by NMR spectroscopy.

Example 25

The synthesis of 1,3-dimethyl-1,3-cyclopentadiene has been reported above in the Example 18.

Synthesis of 1,3,6,6-tetramethylfulvene

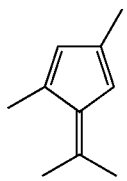

A solution of 1,3-dimethyl-1,3-cyclopentadiene (9.42 g, 0.1 mol) in 100 mL of ethanol was treated at low temperature with 8.6 mL (0.12 mol) of acetone and 9.7 mL (0.12 mol) of pyrrolidine. The resulting solution was kept below room temperature overnight. Then the reaction mixture was neutralized with a 10% aq. solution of H₃PO₄, extracted with hexane (3×50 mL) and washed with water until neutral pH. The organic phase was separated, dried over MgSO₄ and concentrated. The residue was distilled at 63° C./20 mmHg. Yield 6.7 g (50%).

¹H NMR (δ, ppm, CDCl₃): 6.08 (m, 1H, CH); 6.03 (m, 1H, CH); 2.23 (d, 3H, CH₃); 2.17 (s, 3H, CH₃); 2.16 (s, 3H, CH₃); 1.99 (s, 3H, CH₃).

The ligand synthesis was carried out by following the same procedure described in the Example 17, by using 1,3,6,6-tetramethylfulvene instead of 1-methyl-3-isopropyl-6,6-dimethylfulvene and 2,5-ditrimethylsilyl-7H-cyclopenta[1,2-b:4,3-b']dithiophene instead of MeTh₂Cp.

Synthesis of isopropilydene{(2,4-dimethyl-cyclopentadienyl)-7-(2,5-trimethylsilylcyclopenta[1,2-b:4,3-b']-dithiophene)}zirconium dichloride C-15

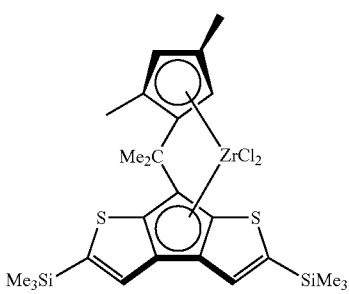

A suspension of 2.19 g (4.8 mmol) of 2,2-(2,4-dimethyl-1-cyclopentadienyl)-7-(2,5-trimethylsilylcyclopenta[1,2-b:4,3-b']-dithiophene)propane in 50 mL of ether was treated at −70° C. with 6.0 mL of a 1.6 M n-BuLi solution (9.6 mmol). After the addition, the reaction mixture was allowed to warm to 0° C. and added of 1.12 g (4.8 mmol) of ZrCl₄. The resulting mixture was allowed to reach room temperature and stirred overnight. Then the red-brown precipitate obtained was filtered, washed twice with ether, dried and finally recrystallyzed from CH₂Cl₂. Yield 2.07 g (70%). The desired title compound was characterized by ¹H-NMR.

Example 26

Synthesis of 3-chloro-2-methyl-2-butenal

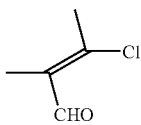

1.3 mol (120 mL) of POCl$_3$ was added at 0° C. to a 1.6 mol (120 mL) of DMF. At the end of the addition, the mixture was allowed to warm to room temperature and stirred for 1 h. Then it was cooled again to 0° C. and treated with 1 mol (90 mL) of 2-butanone. The resulting reaction mixture was allowed to reach room temperature and stirred overnight. Then it was poured into a mixture of ice and water, added of sodium acetate and extracted with CHCl$_3$ (3×150 mL). The organic phase was separated, washed with water until neutral pH, dried over MgSO$_4$ and evaporated off to dryness. The residue was distilled in vacuo, b.p. 45° C./10 torr. Yield 73 g (62%).

Synthesis of 4,5-dimethyl-2-thiophene-ethylcarboxylate

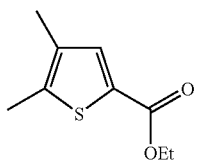

Ethyl-2-mercaptoacetate (0.2 mol, 24 g) was added at 0° C. to a solution of sodium ethoxide (0.21 mol, 14.3 g) in 150 mL of ethanol and the resulting mixture was stirred at the same temperature for 30 min. Then 3-chloro-2-methyl-2-butenal (0.2 mol, 23.7 g) was added and stirring was continued overnight. The resulting product was diluted in 100 mL of water, the organic layer was collected and the water layer was extracted with CH$_2$Cl$_2$ (2×150 mL). The combined organic layers were dried over MgSO$_4$, evaporated off to dryness and the residue distilled in vacuo. Yield 22.48 g (61%).

$^1$H-NMR (δ, ppm, CDCl$_3$): 7.52 (s, 1H, CH); 4.32 (q, 2H, OCH$_2$); 2.35 (s, 3H, CH$_3$); 2.12 (s, 3H, CH$_3$); 1.35 (t, 3H, CH$_3$).

Synthesis of 4,5-dimethyl-2-thiophenecarboxylic acid

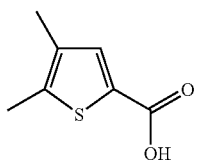

4,5-dimethyl-2-thiophene-ethylcarboxylate (0.122 mol, 22.48 g) was added to a 30% solution of sodium hydroxide in 100 mL of ethanol and the resulting mixture was refluxed for 2 h. Then it was diluted in water, acidified and filtered. The precipitate was dried under P$_2$O$_5$.

Yield 15.6 g (82%). $^1$H-NMR (δ, ppm, CDCl$_3$): 7.60 (s, 1H, CH); 2.42 (s, 3H, CH$_3$); 2.17 (s, 3H, CH$_3$).

Synthesis of 2,3-dimethylthiophene

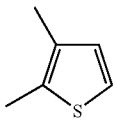

The 4,5-dimethyl-2-thiophenecarboxylic acid prepared as described above (0.58 mol, 90 g) was heated to 180° C. until the evolution of carbon dioxide ceased. The product was collected and distilled, b.p. 140° C.

Yield 30 g (46%). $^1$H-NMR (δ, ppm, CDCl$_3$): 7.02 (d, 1H, CH); 6.82 (d, 1H, CH); 2.42 (s, 3H, CH$_3$); 2.20 (s, 3H, CH$_3$).

Synthesis of 2,3,5-trimethyl-5,6-dihydro-4H-cyclopenta[b]thiophene-4-one

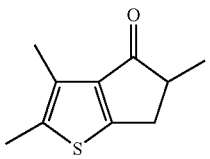

A solution of 10 g of P$_2$O$_5$ (0.07 mol) in 100 mL of methanesulfonic acid (1.54 mol) was heated at 80° C. under stirring. A mixture of 2,3-dimethylthiophene (0.27 mol, 30 g) and methacrylic acid (0.35 mol) in 20 mL of CH$_2$Cl$_2$ was added and the resulting reaction mixture was stirred at the same temperature for 1.5 h. Then it was poured into a mixture of ice and water and stirred vigorously. The water layer was extracted with CH$_2$Cl$_2$ (3×50 mL), the organic layers were collected, washed with a 10% aqueous solution of sodium carbonate until neutral pH and finally with water. Then the organic phase was isolated, dried over MgSO$_4$, evaporated off to dryness and distilled in vacuo, b.p. 110° C./1 torr. Yield 10 g (20%).

$^1$H-NMR (δ, ppm, CDCl$_3$): 3.35 (dd, 1H, CH$_2$); 2.98 (qd, 1H, CH); 2.66 (dd, 1H, CH$_2$); 2.35 (s, 3H, CH$_3$); 2.25 (s, 3H, CH$_3$); 1.52 (d, 3H, CH$_3$).

Synthesis of 2,3,5-trimethyl-6H-cyclopenta[b]thiophene (or 2,3,5trimethyl-1-thiopentalene)

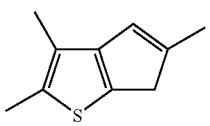

A solution of 2,3,5-trimethyl-5,6-dihydro-4H-cyclopenta[b]thiophene-4-one (11 g, 61 mmol) in 100 mL of ether was slowly added to a solution of LiAlH$_4$ (1.16 g, 30 mmol) in 100 mL of ether and stirred overnight. The resulting suspension was poured into a mixture of ice and water, the organic layer was isolated, while the water layer was extracted with ether (3×50 mL). The combined organic layers were washed with water, dried over MgSO$_4$ and evaporated off to dryness. The 2,3,5-trimethyl-5,6-dihydro-4H-cyclopenta[b]thiophen-4-ol so obtained was dissolved in 100 mL of benzene, added of 1 g of p-toluenesulfonic acid and was refluxed for 10 min. Then the reaction mixture was cooled to room temperature and treated with a saturated aqueous solution of Na$_2$CO$_3$. The organic phase was isolated, dried over MgSO$_4$ and evaporated off to dryness. Yield 8 g (80% based on starting ketone).

$^1$H-NMR (δ, ppm, CDCl$_3$): 6.44 (m, 1H, CH); 3.05 (s, 2H, CH$_2$); 2.45 (s, 3H, CH$_3$); 2.20 (s, 3H, CH$_3$); 2.15 (s, 3H, CH$_3$).

Synthesis of 6H-6-(2,3,5-trimethyl-cyclopenta[b]thiophene)chlorodimethylsilane

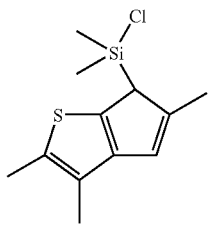

A solution of 1.28 g (5 mmol) of 2,3,5-trimethyl-6H-cyclopenta[b]thiophene in 40 mL of Et$_2$O was treated at −70° C. with 3.13 mL (5 mmol) of a 1.6 M solution of n-BuLi. After the addition, the mixture was allowed to warm to room temperature and stirred for 1 h. Then it was cooled again to −70° C. and treated with a solution of 1.30 g (10 mmol) of Me$_2$SiCl$_2$ in 10 mL of ether. When the addition was completed, the mixture was allowed to reach room temperature and stirred overnight. The resulting reaction mixture was filtered to remove LiCl and solvent was removed under reduced pressure. The crude product was used as such in the next step without further purification.

$^1$H-NM (δ, ppm, C$_6$D$_6$): 6.30 (s, 1H, CH); 3.25 (s, 1H, CH); 2.20 (s, 3H, CH$_3$); 2.10 (s, 3H, CH$_3$); 1.90 (s, 3H, CH$_3$); 0.30 (s, 3H, Si—CE$_3$); −0.10 (s, 3H, Si—CH$_3$).

Synthesis of dimethylsilyl{6-(2,3,5-trimethyl-cyclopenta[b]thiophene)-7-(2,5-dimethyl-cyclopenta[1,2-b:4,3-b']-dithiophene)}zirconium dichloride C-27

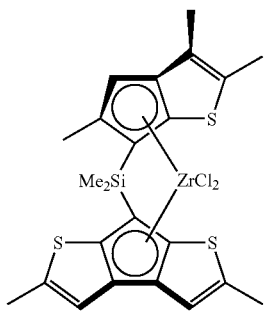

A suspension of 0.9 g (4.4 mmol) of 2,5-dimethyl-7H-cyclopenta[1,2-b:4,3-b']-dithiophene in 20 mL of ether was treated at −70° C. with 2.75 mL of a 1.6 M n-BuLi solution (4.4 mmol). After the addition, the resulting mixture was allowed to warm to room temperature and stirred for additional 50 min at this temperature. Then it was cooled again to −70° C. and added of an etheral solution (10 mL) of 6H-6-(2,3,5-trimethyl-cyclopenta[b]thiophene)chlorodimethylsilane coming from the previous step. The mixture was allowed to warm to room temperature and stirred overnight. The ligand 6-{(2,3,5-trimethyl-cyclopenta[b]thiophene)}-7-{(2,5-dimethyl-cyclopenta[1,2-b:4,3-b']dithiophene)}dimethylsilane so-obtained was characterized by $^1$H-NMR.

$^1$H-NMR (δ, ppm, C$_6$D$_6$): 6.70 (m, 2H, CH); 6.50 (s, 1H, CH); 4.40 (s, 1H, CH); 4.10 (s, 1H, CH); 2.39 (m, 3H, CH$_3$); 2.37 (d, 6H, CH$_3$); 2.25 (s, 3H, CH$_3$); 2.14 (s, 3H, CH$_3$); 0.18 (s, 3H, Si—CH$_3$); 0.07 (s, 3H, Si—CH$_3$).

The ligand was not isolated: its solution was treated at −70° C. with 5.60 mL of a 1.6 M n-BuLi solution (9.0 mmol). Then the reaction mixture was allowed to reach room temperature and stirred for 1 h. The solvent was removed under reduced pressure and the dilithium salt obtained was suspended in hexane. After cooling to −70° C., 1.17 g (5 mmol) of ZrCl$_4$ were added. The reaction mixture was stirred at room temperature overnight, the yellow precipitate was filtered, washed twice with ether, dried and finally recrystallized from CH$_2$Cl$_2$. Yield 1.62 g (60% with respect to Me$_2$Th). The desired title compound was characterized by $^1$H-NMR spectroscopy.

Example 27

Synthesis of 3-chloro-2-methyl-3-phenyl-2-propenal

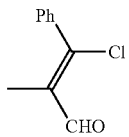

1.2 mol (110 mL) of POCl$_3$ was added at 0° C. to a 2.8 mol (216 mL) of DMF (excess of DMF used as solvent). At the end of the addition, the mixture was allowed to warm to room temperature and stirred for 1 h. Then it was cooled again to 0° C. and treated with 1 mol (134 g) of propiophenone. The resulting reaction mixture was allowed to reach room temperature and stirred overnight. Then it was poured into a mixture of ice and water, added of sodium acetate and extracted with CHCl$_3$ (3×150 mL). The organic phase was separated, washed with water until neutral pH, dried over MgSO$_4$ and evaporated off to dryness. The residue was distilled in vacuo, b.p. 120° C./10 torr. Yield 163 g (90%).

$^1$H-NMR (δ, ppm, CDCl$_3$): 9.52 (s, 1H, CHO); 7.45 (m, 5H, CH); 2.12 (s, 3H, CH$_3$).

Synthesis of 4-methyl-5-phenyl-2-thiophene-ethylcarboxylate

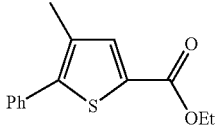

Ethyl-2-mercaptoacetate (0.9 mol, 100 mL) was added at 0° C. to a solution of sodium ethoxide (1 mol, 68 g) in 500 mL of ethanol and the resulting mixture was stirred at the same temperature for 30 min. Then 3-chloro-2-methyl-3-phenyl-2-propenal (0.9 mol, 163 g) was added and stirring was continued overnight. The resulting product was diluted in 1.5 L of water, the organic layer was collected and the water layer was extracted with $CH_2Cl_2$ (4×150 mL). The combined organic layers were dried over $MgSO_4$, evaporated off to dryness and the residue was used in the next step without further purification. The title compound was characterized by $^1H$-NMR spectroscopy.

Synthesis of
4-methyl-5-phenyl-2-thiophenecarboxylic acid

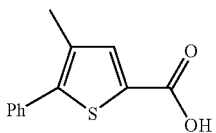

The 4-methyl-5-phenyl-2-thiophene-ethylcarboxylate coming from the previous step was added to a 30% solution of sodium hydroxide in 1 L of ethanol and the resulting mixture was refluxed for 2 h. Then it was diluted in water and extracted with 200 mL of benzene. The water phase was isolated, acidified and the mixture was filtered. The precipitate was dried under $P_2O_5$. Yield 127 g (65% with respect to 03-chloro-2-methyl-3-phenyl-2-propenal).

$^1$H-NMR (δ, ppm, $CDCl_3$): 7.75 (s, 1H, CH); 7.50–7.40 (m, 5H, CH); 2.37 (s, 3H, $CH_3$).

Synthesis of 3-methyl-2-phenylthiophene

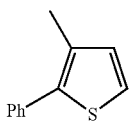

The 4-methyl-5-phenyl-2-thiophenecarboxylic acid (127 g, 0.58 mol) prepared as described above was heated to 220–230° C. until the evolution of carbon dioxide ceased. The product was collected and distilled, b.p. 120° C./10 torr. Yield 30.3 g (30%).

$^1$H-NMR (δ, ppm, $CDCl_3$): 7.60 (d, 2H, CH); 7.48 (t, 2H, CH); 7.35 (t, 1H, CH); 7.25 (d, 1H, CH); 6.98 (d, 1H, CH); 2.39 (s, 3H, $CH_3$).

Synthesis of 2-formyl-4-methyl-5-phenylthiophene

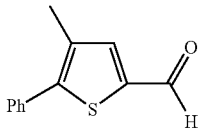

0.35 mol (32 mL) of $POCl_3$ was added at 0° C. to a 1.0 mol (77 mL) of DMF (excess of DMF used as solvent). At the end of the addition, the mixture was allowed to warm to room temperature and stirred for 1 h. Then it was cooled again to 0° C. and treated with 3-methyl-2-phenylthiophene (60 g, 0.35 mol). The resulting reaction mixture was allowed to reach room temperature and after 12 h stirring at the same temperature was heated at 80° C. for 2 days. Then it was poured into a mixture of ice and water, added of sodium acetate and extracted with $CHCl_3$ (3×150 mL). The organic phase was separated, washed with water until neutral pH, dried over $MgSO_4$ and evaporated off to dryness. The residue was crystallized. Yield 60.2 g (85%).

$^1$H-NMR (δ, ppm, $CDCl_3$): 9.88 (s, 1H, CHO); 7.62 (s, 1H, CH); 7.55–7.40 (m, 5H, CH); 2.39 (s, 3H, $CH_3$).

Synthesis of 2-methyl-3-(4-methyl-5-phenyl-2-thienyl)-acrylic acid

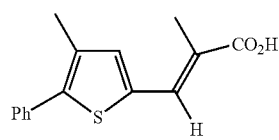

A mixture of 2-formyl-4-methyl-5-phenylthiophene (20.2 g, 0.1 mol) and ethyl-2-bromopropionate (0.12 mol, 15.5 mL) was added to a suspension of Zn (7 g, 0.1 mol) in 150 mL of benzene with a catalytic amount of $HgBr_2$. The resulting mixture was refluxed under stirring while all amount of Zn will not be dissolved, and subsequently dissolved in water. The organic layer was isolated, washed with a 10% aq. solution of HCl, dried over $MgSO_4$ and evaporated off to dryness. The residue, corresponding to 2-methyl-3-(4-methyl-5-phenyl-2-thienyl)ethyl acrylate, was used without further purification in the synthesis of the related acid. In fact, it was added to a 30% aq. solution of sodium hydroxide in 100 mL of ethanol and refluxed for 2 h. The resulting reaction mixture was diluted in water, acidified and filtered. The precipitate was dried under $P_2O_5$. Yield 16.7 g (65%).

$^1$H-NMR (δ, ppm, $CDCl_3$): 7.90 (s, 1H, CH); 7.50–7.30 (m, 5H, CH); 7.20 (s, 1H, CH); 2.40 (s, 3H, $CH_3$); 2.20 (s, 3H, $CH_3$).

Synthesis of 2-methyl-3-(4-methyl-5-phenyl-2-thienyl)-2-propanoic acid

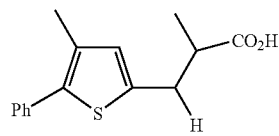

The desired 2-methyl-3-(4-methyl-5-phenyl-2-thienyl)-2-propanoic acid was obtained by electrochemical reduction of 2-methyl-3-(4-methyl-5-phenyl-2-thienyl)acrylic acid. Yield≈100%.

$^1$H-NMR (δ, ppm, $CDCl_3$): 7.50–7.30 (m, 5H, CH); 6.70 (s, 1H, CH); 3.30 (dd, 1H, CH); 2.90 (m, 2H, $CH_2$); 2.30 (s, 3H, $CH_3$); 1.30 (d, 3H, $CH_3$).

Synthesis of 3,5-dimethyl-2-phenyl-5,6-dihydro-4H-cyclopenta[b]thiophene4-one

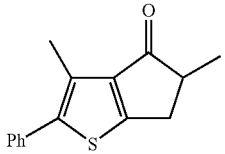

A solution of 3 g of $P_2O_5$ (21 mmol) in 30 mL of methanesulfonic acid (0.46 mol) was heated at 80° C. under stirring. A solution of 2-methyl-3-(4-methyl-5-phenyl-2-thienyl)-2-propanoic acid (65 mmol, 16.9 g) in 20 mL of $CH_2Cl_2$ was added and the resulting reaction mixture was stirred at the same temperature for 1.5 h. Then it was poured into a mixture of ice and water and stirred vigorously. The water layer was extracted with $CH_2Cl_2$ (3×50 mL), the organic layers were collected, washed with a 10% aqueous solution of sodium carbonate until neutral pH and finally with water. Then the organic phase was isolated, dried over $MgSO_4$ and evaporated off to dryness. Yield 6.3 g (40%).

$^1$H-NMR (δ, ppm, $CDCl_3$): 7.50–7.40 (m, 5H, CH); 3.40 (dd, 1H, $CH_2$); 3.05 (m, 1H, CH); 2.80 (dd, 1H, $CH_2$); 2.55 (s, 3H, $CH_3$); 1.40 (d, 3H, $CH_3$).

Synthesis of 3,5-dimethyl-2-phenyl-6H-cyclopenta[b]thiophene (or 3,5-dimethyl-2-phenyl-1-thiopentalene)

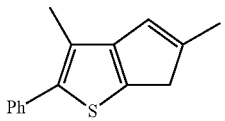

A solution of 3,5-dimethyl-2-phenyl-5,6-dihydro-4H-cyclopenta[b]thiophene-4-one (6.3 g, 26 mmol) in 75 mL of ether was slowly added to a solution of $LiAlH_4$ (0.5 g, 13 mmol) in 50 mL of ether and stirred overnight. The resulting suspension was poured into a mixture of ice and water, the organic layer was isolated, while the water layer was extracted with ether (3×50 mL). The combined organic layers were washed with water, dried over $MgSO_4$ and evaporated off to dryness.

The 3,5-dimethyl-2-phenyl-5,6-dihydro-4H-cyclopenta[b]thiophen-4-ol so obtained was dissolved in 100 mL of benzene, added of 1 g of p-toluenesulfonic acid and was refluxed for 10 min. Then the reaction mixture was cooled to room temperature and treated with a saturated aqueous solution of $Na_2CO_3$. The organic phase was isolated, dried over $MgSO_4$ and evaporated off to dryness. Yield 4.66 g (80% based on the starting ketone).

$^1$H-NMR (δ, ppm, $CDCl_3$): 7.50–7.40 (m, 5H, CH); 6.50 (q, 1H, CH); 3.20 (d, 1H, $CH_2$); 2.60 (dd, 1H, $CH_2$); 2.20 (s, 3H, $CH_3$); 1.66 (s, 3H, $CH_3$).

Synthesis of 6H-6-(2-phenyl-3,5-dimethyl-cyclopenta[b]thiophene)chloro dimethylsilane

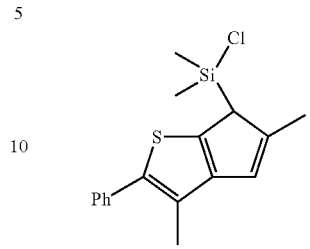

A solution of 1.70 g (7.5 mmol) of 3,5-dimethyl-2-phenyl-6H-cyclopenta[b]thiophene in 40 mL of $Et_2O$ was treated at −70° C. with 5.0 mL (8 mmol) of a 1.6 M solution of n-BuLi. After the addition, the mixture was allowed to warm to room temperature and stirred for 1 h. Then it was cooled again to −70° C. and treated with a solution of 1.30 g (10 mmol) of $Me_2SiCl_2$ in 10 mL of ether. When the addition was completed, the mixture was allowed to reach room temperature and stirred overnight. The resulting reaction mixture was filtered to remove LiCl and solvent was removed under reduced pressure. The crude product was used as such in the next step without further purification.

$^1$H-NMR (δ, ppm, $C_6D_6$): 7.60–7.20 (m, 5H, CH); 6.50 (m, 1H, CH); 3.40 (s, 1H, CH); 2.84 (s, 3H, $CH_3$); 2.21 (s, 3H, $CH_3$); 0.39 (s, 3H, Si—$CH_3$); 0.12 (s, 3H, Si—$CH_3$).

Synthesis of dimethylsilyl{6-(2-phenyl-3,5-dimethyl-cyclopenta[b]thiophene)-7-(2,5-dimethyl-cyclopenta[1,2-b:4,3-b']-dithiophene)}zirconium dichloride C-29

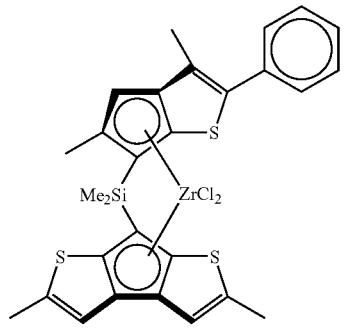

A suspension of 1.3 g (6.3 mmol) of 2,5-dimethyl-7H-cyclopenta[1,2-b:4,3-b']-dithiophene in 30 mL of ether was treated at −70° C. with 4.0 mL of a 1.6 M n-BuLi solution (6.4 mmol). After the addition, the resulting mixture was allowed to warm to room temperature and stirred for additional 50 min at this temperature. Then it was cooled again to −70° C. and added of an etheral solution (10 mL) of 6H-6-(3,5-dimethyl-2-phenyl-cyclopenta[b]thiophene)chlorodimethylsilane coming from the previous step. The mixture was allowed to warm to room temperature and stirred overnight. The ligand 6-{(3,5-dimethyl-2-phenyl-cyclopenta[b]thiophene)}-7-{(2,5-dimethyl-cyclopenta[1,2-b:4,3-b']-dithiophene)}dimethylsilane so-obtained was characterized by $^1$H-NMR.

¹H-NMR (δ, ppm, C₆D₆): 7.60–7.10 (m, 5H, CH); 6.85 (s, 1H, CH); 6.80 (s, 1H, CH); 6.50 (m, 1H, CH); 4.37 (s, 1H, CH); 4.10 (s, 1H, CH); 2.38 (d, 3H, CH₃); 2.37 (d, 3H, CH₃); 2.36 (s, 3H, CH₃); 2.12 (s, 3H, CH₃); −0.05 (s, 3H, Si—CH₃); −0.16 (s, 3H, Si—CH₃).

The ligand was not isolated: its solution was treated at −70° C. with 8.2 mL of a 1.6 M n-BuLi solution (13.1 mmol). Then the reaction mixture was allowed to reach room temperature and stirred for 1 h. The solvent was removed under reduced pressure and the dilithium salt obtained was suspended in hexane. After cooling to −70° C., 1.51 g (6.5 mmol) of ZrCl₄ were added. The reaction mixture was stirred at room temperature overnight, the yellow-brown precipitate was filtered, washed twice with ether, dried and finally recrystallized from CH₂Cl₂. Yield 2.30 g (56% with respect to Me₂Th). The desired title compound was characterized by ¹H-NMR.

¹H-NMR (δ, ppm, CD₂Cl₂): 7.44–7.36 (m, 5H, CH); 6.86 (q, 1CH, J=1.24 Hz); 6.73 (q, 1H, CH, J=1.24 Hz); 6.56 (bs, 1H, CH); 2.63 (d, 3H, CH₃, J=1.24 Hz); 2.50 (d, 3H. CH₃, J=1.24 Hz); 2.35 (s, 3H, CH₃); 2.20 (s, 3H, CH₃); 1.22 (s, 3H, Si—CH₃); 1.14 (s, 3H, Si—CH₃).

Example 28

Synthesis of 3-chloro-2,3-diphenyl-2-propenal

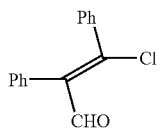

0.25 mol (23 mL) of POCl₃ was added at 0° C. to a 0.3 mol (23.5 mL) of DMF. At the end of the addition, the mixture was allowed to warm to room temperature and stirred for 1 h. Then it was cooled again to 0° C. and treated with 0.1 mol (19.6 g) of deoxybenzoin. The resulting reaction mixture was allowed to reach room temperature, stirred for 12 h at the same temperature and subsequently heated at 100° C. for 2 h. Finally it was poured into a mixture of ice and 10% solution of sodium acetate in water. The oily precipitate was filtered and washed with cold methanol and hexane. The residue was crystallized. Yield 18.5 g (76%).

¹H-NMR (δ, ppm, CDCl₃): 9.70 (s, 1H, CHO); 7.60–7.20 (m, 10H, CH).

Synthesis of 4,5-diphenyl-2-thiophene-ethylcarboxylate

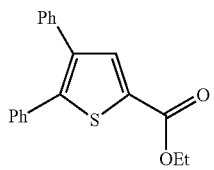

Ethyl-2-mercaptoacetate (40 mmol, 4.4 mL) was added at 0° C. to a solution of sodium ethoxide (42 mmol, 2.86 g) in 50 mL of ethanol and the resulting mixture was stirred at the same temperature for 30 min. Then 3-chloro-2,3-diphenyl-2-propenal (37 mmol, 9.0 g) was added and stirring was continued overnight. The resulting orange suspension was heated at 50° C. for 2 h, then cooled to room temperature and diluted in 100 mL of water. The so-obtained red solution containing a precipitate was extracted with Et₂O (3×50 mL). The combined organic layers were washed with NH₄Cl/water, dried over MgSO₄ and evaporated off to dryness. The solid residue was recrystallized from hexane. Yield 9.2 g (81%).

¹H-NMR (δ, ppm, CDCl₃): 7.40–7.30 (m, 11H, CH); 4.40 (q, 2H, CH₂); 1.40 (t, 3H, CH₃).

Synthesis of 4,5-diphenyl-2-thiophenecarboxylic acid

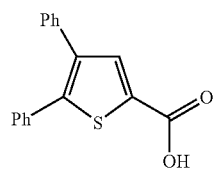

The 4,5-diphenyl-2-thiophene-ethylcarboxylate (3.6 g, 12 mmol) coming from the previous step was added to a 30% solution of sodium hydroxide in 20 mL of ethanol and the resulting mixture was refluxed for 2 h. Then it was diluted in water and the water phase was acidified. The white precipitate obtained was filtered and dried at 80° C. Yield 3.16 g (94%).

¹H-NMR (δ, ppm, (CD₃)₂SO): 7.80 (s, 1H, CH); 7.40–7.30 (m, 10H, CH).

Synthesis of 2,3-diphenylthiophene

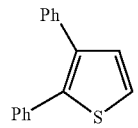

The 4,5-diphenyl-2-thiophenecarboxylic acid (28 g, 0.1 mol) prepared as described above was heated to 220–230° C. until the evolution of carbon dioxide ceased. The residue was diluted in water and extracted with 100 mL of benzene. The organic phase was dried over MgSO₄ and evaporated off to give the crystallized product. Yield 22.45 g (95%).

¹H-NMR (δ, ppm, CDCl₃): 7.35 (d, 1H, CH); 7.34–7.26 (m, 10H, CH); 7.19 (d, 1H, CH).

Synthesis of 2-formyl-4,5-diphenylthiophene

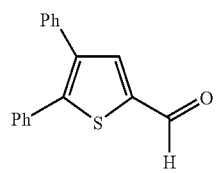

POCl₃ (80 mmol, 7.32 mL) was added at 0° C. to a solution of 2,3-diphenylthiophene (18 g, 76 mmol) in DMF (18 mL, 0.23 mol). At the end of the addition, the reaction mixture was allowed to warm to room temperature and refluxed for 3 h. Then it was cooled to room temperature and poured into a mixture of ice and a 10% solution of sodium hydroxide in water. The oily precipitate obtained was filtered and washed with cold methanol and hexane. The residue was crystallized. Yield 15 g (75%).

$^1$H-NMR (δ, ppm, CDCl$_3$): 9.95 (s, 1H, CHO); 7.82 (s, 1H, CH); 7.40–7.25 (m, 10H, CH).

Synthesis of 2-methyl-3-(4,5-diphenyl-2-thienyl)-ethyl acrylate

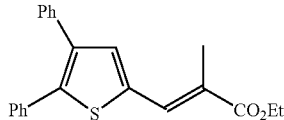

A mixture of 2-formyl-4,5-diphenylthiophene (14.8 g, 56 mmol) and ethyl-2-bromopropionate (60 mmol, 7.8 mL) was added to a suspension of Zn (4.25 g, 65 mmol) in 100 mL of benzene with a catalytic amount of I$_2$. The resulting mixture was refluxed under stirring while all amount of Zn will not be dissolved, and subsequently dissolved in water. The organic layer was isolated, washed with a 10% aq. solution of HCl, dried over MgSO$_4$ and evaporated off to dryness. The residue was dissolved into 50 mL of benzene and was refluxed with 0.5 g of p-toluenesulfonic acid for 1 h. Then the reaction mixture was cooled to room temperature and treated with a saturated aqueous solution of Na$_2$CO$_3$. The organic phase was isolated, dried over MgSO$_4$ and evaporated off to dryness. Yield 17.6 g (90%).

$^1$H-NMR (δ, ppm, CDCl$_3$): 7.90 (s, 1H, CH); 7.40–7.25 (m, 11H, CH); 4.30 (q, 2H, CH$_2$); 2.30 (d, 3H, CH$_3$); 1.40 (t, 3H, CH$_3$).

Synthesis of 2-methyl-3-(4,5-diphenyl-2-thienyl)-acrylic acid

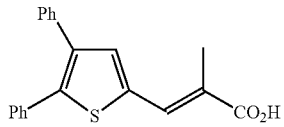

The 2-methyl-3-(4,5-diphenyl-2-thienyl)-ethyl acrylate (18.9 g, 54 mmol), coming from the previous step, was added to a 30% aq. solution of sodium hydroxide in 300 mL of ethanol and refluxed for 2 h. The resulting reaction mixture was diluted in water, acidified and filtered. The precipitate was dried under P$_2$O$_5$. Yield 12.1 g (70%).

$^1$H-NMR (δ, ppm, (CD$_3$)$_2$SO): 7.85 (d, 1H, CH); 7.55 (s, 1H, CH); 7.40–7.20 (m, 10H, CH); 2.15 (s, 3H, CH$_3$).

Synthesis of 2-methyl-3-(4,5-diphenyl-2-thienyl)-2-propanoic acid

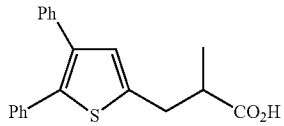

The desired 2-methyl-3-(4,5-diphenyl-2-thienyl)-2-propanoic acid was obtained by electrochemical reduction of 2-methyl-3-(4,5-diphenyl-2-thienyl)-acrylic acid. Yield≈100%.

$^1$H-NMR (δ, ppm, (CD$_3$)$_2$SO): 7.30–7.15 (m, 10H, CH); 6.90 (s, 1H, CH); 3.10 (dd, 1H, CH); 2.70 (m, 2H, CH$_2$); 1.10 (d, 3H, CH$_3$).

Synthesis of 5-methyl-2,3-diphenyl-5,6-dihydro-4H-cyclopenta[b]thiophene-4-one

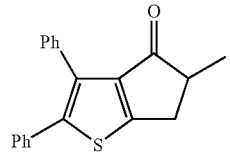

A solution of P$_2$O$_5$ (2.6 g, 18 mmol) in 15 mL of methanesulfonic acid (0.23 mol) was heated at 80° C. under stirring. A solution of 2-methyl-3-(4,5-diphenyl-2-thienyl)-2-propanoic acid (18 mmol, 6.0 g) in 20 mL of CH$_2$Cl$_2$ was added and the resulting reaction mixture was stirred at the same temperature for 15 min. Then it was poured into a mixture of ice and water and stirred vigorously. The water layer was extracted with CH$_2$Cl$_2$ (3×50 mL), the organic layers were collected, washed with a 10% aqueous solution of sodium carbonate until neutral pH and finally with water. Then the organic phase was isolated, dried over MgSO$_4$ and evaporated off to dryness. The residue was passed through a column packed with silica gel 60 by using a mixture hexane/ethyl acetate=5/1 as eluent. The evaporation of the red fraction was given the crystallized product. Yield 2.18 g (40%).

$^1$H-NMR (δ, ppm, CDCl$_3$): 7.40–7.20 (m, 10H, CH); 3.50 (dd, 1H, CH$_2$); 3.05 (m, 1H, CH); 2.85 (dd, 1H, CH$_2$); 1.40 (d, 3H, CH$_3$).

Synthesis of 5-dimethyl-2,3-diphenyl-6H-cyclopenta[b]thiophene (or 5-dimethyl-2,3-diphenyl-1-thiopentalene)

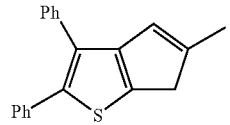

A solution of 5-methyl-2,3-diphenyl-5,6-dihydro-4H-cyclopenta[b]thiophene-4-one (6.08 g, 20 mmol) in 75 mL of ether was slowly added to a solution of LiAlH$_4$ (0.38 g, 10 mmol) in 50 mL of ether and stirred overnight. The resulting suspension was poured into a mixture of ice and water, the organic layer was isolated, while the water layer was extracted with ether (3×50 mL). The combined organic layers were washed with water, dried over MgSO$_4$ and evaporated off to dryness. The 5-methyl-2,3-diphenyl-5,6-dihydro-4H-cyclopenta[b]thiophen -4-ol so obtained was dissolved in 100 mL of benzene, added of 1 g of p-toluenesulfonic acid and was refluxed for 10 min. Then the reaction mixture was cooled to room temperature and treated with a saturated aqueous solution of Na$_2$CO$_3$. The organic phase was isolated, dried over MgSO$_4$ and evaporated off to dryness giving the crystallized product. Yield 3.46 g (60% with respect to the starting ketone).

$^1$H-NMR (δ, ppm, CDCl$_3$): 7.40–7.20 (m, 10H, CH); 6.48 (q, 1H, CH); 3.24 (s, 2H, CH$_2$); 2.24 (d, 3H, CH$_3$).

Synthesis of 6H-6-(5-methyl-2,3-diphenyl-cyclopenta[b]thiophene)chloro dimethylsilane

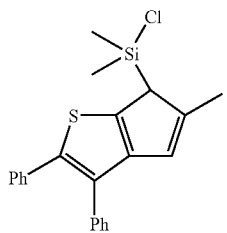

A solution of 1.28 g (4.4 mmol) of 5-methyl-2,3-diphenyl-6H-cyclopenta[b]thiophene in 40 mL of Et$_2$O was treated at −70° C. with 3.5 mL (5.6 mmol) of a 1.6 M solution of n-BuLi. After the addition, the mixture was allowed to warm to room temperature and stirred for 1 h. Then it was cooled again to −70° C. and treated with a solution of 1.30 g (10 mmol) of Me$_2$SiCl$_2$ in 10 mL of ether. When the addition was completed, the mixture was allowed to reach room temperature and stirred overnight. The resulting reaction mixture was filtered to remove LiCl and the solvent was removed under reduced pressure. The crude product was used as such in the next step without further purification.

$^1$H-NMR (δ, ppm, C$_6$D$_6$): 7.60–7.00 (m, 10H, CH); 6.56 (m, 1H, CH); 3.40 (s, 1H, CH); 2.13 (s, 3H, CH$_3$); 0.37 (s, 3H, Si—CH$_3$); 0.15 (s, 3H, Si—CH$_3$).

Synthesis of dimethylsilyl{6-(5-methyl-2,3-diphenyl-cyclopenta[b]thiophene)-7-(2,5-dimethyl-cyclopenta[1,2-b:4,3-b']-dithiophene)}zirconium dichloride C-30

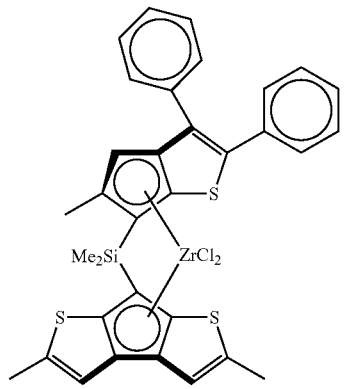

A suspension of 0.9 g (4.4 mmol) of 2,5-dimethyl-7H-cyclopenta[1,2-b:4,3-b']-dithiophene in 30 mL of ether was treated at −70° C. with 3.0 mL of a 1.6 M n-BuLi solution (4.8 mmol). After the addition, the resulting mixture was allowed to warm to room temperature and stirred for additional 50 min at this temperature. Then it was cooled again to −70° C. and added of an etheral solution (10 mL) of 6H-6-(5-methyl-2,3-diphenyl-cyclopenta[b]thiophene)chlorodimethylsilane coming from the previous step. The mixture was allowed to warm to room temperature and stirred overnight. The ligand 6-{(5-methyl-2,3-diphenyl-cyclopenta[b]thiophene)}-7-{(2,5-dimethyl-cyclopenta[1,2-b:4,3-b']-dithiophene)}dimethylsilane so-obtained was characterized by $^1$H-NMR.

$^1$H-NMR (δ, ppm, C$_6$D$_6$): 7.60–7.00 (m, 10H, CH); 6.85 (m, 1H, CH); 6.80 (m, 1H, CH); 6.60 (m, 1H, CH); 4.35 (s, 1H, CH); 4.10 (s, 1H, CH); 2.40 (d, 3H, CH$_3$); 2.38 (d, 3H, CH$_3$); 2.05 (s, 3H, CH$_3$); 0.05 (s, 3H, Si—CH$_3$); −0.20 (s, 3H, Si—CH$_3$).

The ligand was not isolated: its solution was treated at −70° C. with 5.6 mL of a 1.6 M n-BuLi solution (9.0 mmol). Then the reaction mixture was allowed to reach room temperature and stirred for 1 h. The solvent was removed under reduced pressure and the dilithium salt obtained was suspended in hexane. After cooling to −70° C., 1.17 g (5.0 mmol) of ZrCl$_4$ were added. The reaction mixture was stirred at room temperature overnight, the yellow precipitate was filtered, washed twice with ether, dried and finally recrystallized from CH$_2$Cl$_2$. Yield 1.46 g (47% with respect to Me$_2$Th).

$^1$H-NMR (δ, ppm, CD$_2$Cl$_2$): 7.39–7.24 (m, 10H, CH); 6.88 (q, 1H, CH, J=1.17 Hz); 6.76 (q, 1H, CH, J=1.17 Hz); 6.59 (bs, 1H, CH); 2.63 (d, 3H, CH$_3$, J=1.17 Hz); 2.51 (d, 3H, CH$_3$, J=1.17 Hz); 2.35 (s, 3H, CH$_3$); 1.25 (s, 3H, Si—CH$_3$); 1.16 (s, 3H, Si—CH$_3$).

Example 29

Synthesis of 3-chloro-2-phenyl-2-butenal

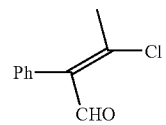

0.375 mol (35 mL) of POCl$_3$ was added at 0° C. to a 0.45 mol (35 mL) of DMF. At the end of the addition, the mixture was allowed to warm to room temperature and stirred for 1 h. Then it was cooled again to 0° C. and carefully treated with 0.15 mol (20.1 g) of phenylacetone. The resulting reaction mixture was stirred at the same temperature for 1 h. Then it was poured into a mixture of ice and water, added of sodium acetate and extracted with CHC$_3$ (3×50 mL). The organic phase was separated, washed with water until neutral pH, dried over MgSO$_4$ and carefully evaporated off to dryness. The residue was distilled in vacuo, b.p. 90–110° C./0.21 torr.

Yield 10 g (37%). $^1$H-NMR (δ, ppm, CDCl$_3$): 10.50 (s, 1H, CHO); 7.40–7.00 (m, 5H, CH); 2.20 (s, 3H, CH$_3$).

Synthesis of 5-methyl-4-phenyl-2-thiophene-ethylcarboxylate

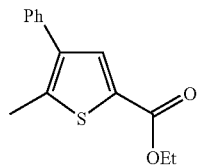

Ethyl-2-mercaptoacetate (45.8 mmol, 5 mL) was added at 0° C. to a solution of sodium ethoxide (46 mmol, 3.13 g) in 50 mL of ethanol and the resulting mixture was stirred at the same temperature for 30 min. Then 3-chloro-2-phenyl-2-butenal (45.8 mmol, 8.27 g) was added and stirring was continued overnight. The resulting product was refluxed for 2 h, cooled to room temperature and diluted in 100 mL of water. The organic layer was collected and the water layer was extracted with $CH_2Cl_2$ (3×50 mL). The combined organic layers were dried over $MgSO_4$, evaporated off to dryness and the residue was used in the next step without further purification. The title compound was characterized by $^1$H-NMR spectroscopy.

Synthesis of 5-methyl-4-phenyl-2-thiophenecarboxylic acid

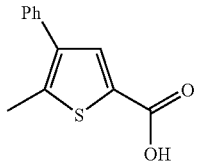

The 5-methyl-4-phenyl-2-thiophene-ethylcarboxylate coming from the previous step was added to a 30% solution of sodium hydroxide in 100 mL of ethanol and the resulting mixture was refluxed for 2 h. Then it was diluted in water and extracted with 50 mL of benzene. The water phase was isolated, acidified and the mixture was filtered. The precipitate was dried under $P_2O_5$. Yield 9.5 g (95% based on 3-chloro-2-phenyl-2-butenal).

$^1$H-NMR (δ, ppm, $CDCl_3$): 12.00 (s, 1H, COOH); 7.90 (s, 1H, CH); 7.50–7.40 (m, 5H, CH); 2.55 (s, 3H, CH3).

Synthesis of 2-methyl-3-phenylthiophene

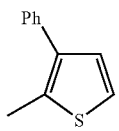

The 5-methyl-4-phenyl-2-thiophenecarboxylic acid (54 g, 0.25 mol) prepared as described above was heated to 220–230° C. until the evolution of carbon dioxide ceased. The product was collected and distilled, b.p. 117° C./10 torr. Yield 30 g (70%).

$^1$H-NMR (δ, ppm, $CDCl_3$): 7.45 (m, 5H, CH); 7.15 (d, 1H, CH); 7.10 (d, 1H, CH); 2.55 (s, 3H, $CH_3$).

Synthesis of 2-formyl-5-methyl-4-phenylthiophene

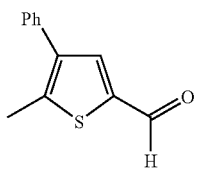

0.166 mol (15 mL) of $POCl_3$ was added at 0° C. to a 0.5 mol (39 mL) of DMF. At the end of the addition, the mixture was allowed to warm to room temperature and stirred for 1 h. Then it was cooled again to 0° C. and treated with 2-methyl-3-phenylthiophene (29 g, 0.166 mol). The resulting reaction mixture was allowed to reach room temperature and after 12 h stirring at the same temperature was heated at 80° C. for 2 days. Then it was poured into a mixture of ice and water and added of sodium acetate. The precipitate so obtained was filtered, washed with water and subsequently with hexane. The yellow powder was dried in vacuo.

Yield 27.7 g (83%). $^1$H-NMR (δ, ppm, $CDCl_3$): 9.88 (s, 1H, CHO); 7.70 (s, 1H, CH); 7.55–7.40 (m, 5H, CH); 2.55 (s, 3H, $CH_3$).

Synthesis of 2-methyl-3-(5-methyl-4-phenyl-2-thienyl)-ethyl acrylate

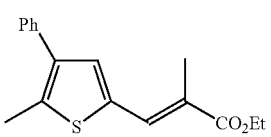

A mixture of 2-formyl-5-methyl-4-phenylthiophene (27.6 g, 0.136 mol) and ethyl-2-bromopropionate (0.14 mol, 18.2 mL) was added to a suspension of Zn (9.8 g, 0.15 mol) in 250 mL of benzene with a catalytic amount of $I_2$. The resulting mixture was refluxed under stirring while all amount of Zn will not be dissolved, and subsequently dissolved in water. The organic layer was isolated, washed with a 10% aq. solution of HCl, dried over $MgSO_4$ and evaporated off to dryness. The residue was used without further purification in the synthesis of the related acid. The title compound was characterized by $^1$H-NMR spectroscopy.

Synthesis of 2-methyl-3-(5-methyl-4-phenyl-2-thienyl)-acrylic acid

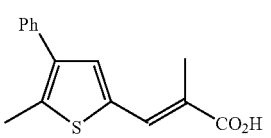

The 2-methyl-3-(5-methyl-4-phenyl-2-thienyl)-ethyl acrylate coming from the previous step was added to a 30% aq. solution of sodium hydroxide in 200 mL of ethanol and refluxed for 2 h. The resulting reaction mixture was diluted in water, acidified and filtered. The precipitate was dried under $P_2O_5$. Yield 26.0 g (74% based on 2-formyl-5-methyl-4-phenylthiophene).

$^1$H-NMR (δ, ppm, $CDCl_3$): 7.90 (s, 1H, CH); 7.50–7.30 (m, 5H, CH); 7.25 (d, 1H, CH); 2.60 (s, 3H, $CH_3$); 2.25 (s, 3H, $CH_3$).

Synthesis of 2-methyl-3-(5-methyl-4-phenyl-2-thienyl)-2-propanoic acid

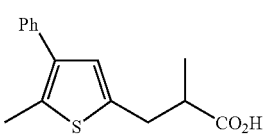

The desired 2-methyl-3-(5-methyl-4-phenyl-2-thienyl)-2-propanoic acid was obtained by electrochemical reduction of 2-methyl-3-(5-methyl-4-phenyl-2-thienyl)acrylic acid. Yield≈100%.

$^1$H-NMR (δ, ppm, CDCl$_3$): 7.50–7.20 (m, 5H, CH); 6.80 (s, 1H, CH); 3.25 (dd, 1H, CH); 2.85 (m, 2H, CH$_2$); 2.50 (s, 3H, CH$_3$); 1.30 (d, 3H, CH$_3$).

Synthesis of 2,5-dimethyl-3-phenyl-5,6-dihydro-4H-cyclopenta[b]thiophene-4-one

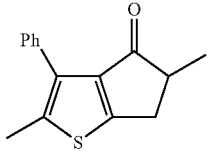

A solution of 3 g of P$_2$O$_5$ (21 mmol) in 30 mL of methanesulfonic acid (0.46 mol) was heated at 80° C. under stirring. A solution of 2-methyl-3-(5-methyl-4-phenyl-2-thienyl)-2-propanoic acid (65 mmol, 16.9 g) in 20 ml, of CH$_2$Cl$_2$ was added and the resulting reaction mixture was stirred at the same temperature for 1.5 h. Then it was poured into a mixture of ice and water and stirred vigorously. The water layer was extracted with CH$_2$Cl$_2$ (3×50 mL), the organic layers were collected, washed with a 10% aqueous solution of sodium carbonate until neutral pH and finally with water. Then the organic layers were collected, dried over MgSO$_4$ and evaporated off to dryness. The residue was passed through a column packed with silica gel 60 by using a mixture of hexane/ethyl acetate=3/1 as eluent. The evaporation of the red fraction was given the oily product. Yield 4.4 g (28%).

$^1$H-NMR (δ, ppm, CDCl$_3$): 7.50–7.40 (m, 5H, CH); 3.42 (dd, 1H, CH$_2$); 3.02 (m, 1H, CH); 2.79 (dd, 1H, CH$_2$); 2.50 (s, 3H, CH$_3$); 1.35 (d, 3H, CH$_3$).

Synthesis of 2,5-dimethyl-3-phenyl-6H-cyclopenta[b]thiophene (or 2,5-dimethyl-3-phenyl-1-thiopentalene)

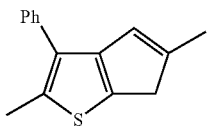

A solution of 2,5-dimethyl-3-phenyl-5,6-dihydro-4H-cyclopenta[b]thiophene-4-one (4.4 g, 18 mmol) in 50 mL of ether was slowly added to a solution of LiAlH$_4$ (0.35 g, 9 mmol) in 50 mL of ether and stirred overnight. The resulting suspension was poured into a mixture of ice and water, the organic layer was isolated, while the water layer was extracted with ether (3×50 mL). The combined organic layers were washed with water, dried over MgSO$_4$ and evaporated off to dryness. The 2,5-dimethyl-3-phenyl-5,6-dihydro-4H-cyclopenta[b]thiophen-4-ol so obtained was dissolved in 100 mL of benzene, added of 1 g of p-toluenesulfonic acid and was refluxed for 10 min. Then the reaction mixture was cooled to room temperature and treated with a saturated aqueous solution of Na$_2$CO$_3$. The organic phase was isolated, dried over MgSO$_4$ and evaporated off to dryness. The residue was passed through a column packed with Al$_2$O$_3$ by using hexane as eluent. The evaporation of the yellow fraction was given the crystallized product. Yield 1.5 g (37% based on the starting ketone).

$^1$H-NMR (δ, ppm, CDCl$_3$): 7.50–7.40 (m, 5H, CH); 6.52 (q, 1H, CH); 3.24 (d, 1H, CH$_2$); 2.60 (d, 1H, CH$_2$); 2.24 (dd, 3H, CH$_3$); 1.66 (s, 3H, CH$_3$).

Synthesis of 6H-6-(2,5-dimethyl-3-phenyl-cyclopenta[b]thiophene)chloro dimethylsilane

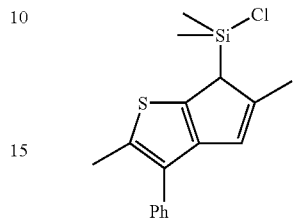

A solution of 1.20 g (5.3 mmol) of 2,5-dimethyl-3-phenyl-6H-cyclopenta[b]thiophene in 40 mL of Et$_2$O was treated at −70° C. with 3.3 mL (5.3 mmol) of a 1.6 M solution of n-BuLi. After the addition, the mixture was allowed to warm to room temperature and stirred for 1 h. Subsequently it was cooled again to −70° C. and treated with a solution of 1.30 g (10.1 mmol) of Me$_2$SiCl$_2$ in 10 mL of ether. When the addition was completed, the mixture was allowed to reach room temperature and stirred overnight. The resulting reaction mixture was filtered to remove LiCl and solvent was removed under reduced pressure. The crude product was used as such in the next step without further purification.

$^1$H-NMR (δ, ppm, C$_6$D$_6$): 7.45–7.20 (m, 5H, CH); 6.50 (m, 1H, CH); 3.40 (m, 1H, CH); 2.38 (s, 3H, CH$_3$); 2.12 (s, 3H, CH$_3$); 0.36 (s, 3H, Si—CH$_3$); 0.11 (s, 3H, Si—CH$_3$).

Synthesis of dimethylsilyl{6-(2,5-dimethyl-3-phenyl-cyclopenta[b]thiophene)-7-(2,5-dimethyl-cyclopenta[1,2-b:4,3-b']-dithiophene)} zirconium dichloride C-33

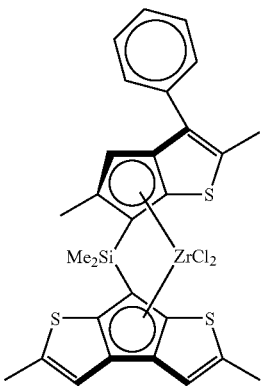

A suspension of 0.9 g (4.4 mmol) of 2,5-dimethyl-7H-cyclopenta[1,2-b:4,3-b']-dithiophene in 30 mL of ether was treated at −70° C. with 3.0 mL of a 1.6 M n-BuLi solution (4.8 mmol). After the addition, the resulting mixture was allowed to warm to room temperature and stirred for additional 50 min at this temperature. Then it was cooled again to −70° C. and added of an etheral solution (10 mL) of 6H-6-(2,5-dimethyl-3-phenyl-cyclopenta[b]thiophene)chlorodimethylsilane coming from the previous step. The mixture was allowed to warm to room temperature and stirred overnight. The ligand 6-{(2,5-dimethyl-3-phenyl-cyclopenta[b]thiophene)}-7-{(2,5-dimethyl-cyclopenta[1,2-b:4,3-b']-dithiophene)}dimethylsilane so-obtained was characterized by $^1$H-NMR.

$^1$H-NMR (δ, ppm, CDCl$_3$): 7.45–7.20 (m, 5H, CH); 6.85 (s, 1H, CH); 6.80 (s, 1H, CH); 6.60 (m, 1H, CH); 4.30 (s, 1H, CH); 4.00 (s, 1H, CH); 2.70 (d, 3H, CH3); 2.65 (d, 3H, CH$_3$); 2.60 (s, 3H, CH$_3$); 2.30 (s, $_3$H, CH$_3$); −0.18 (s, 3H, Si—CH3); −0.30 (s, 3H, Si—CH$_3$).

The ligand was not isolated: its solution was treated at −70° C. with 5.6 mL of a 1.6 M n-BuLi solution (9.0 mmol). Then the reaction mixture was allowed to reach room temperature and stirred for 1 h. The solvent was removed under reduced pressure and the dilithium salt obtained was suspended in hexane. After cooling to −70° C., 1.17 g (5.0 mmol) of ZrCl$_4$ were added. The reaction mixture was stirred at room temperature overnight, the yellow precipitate was filtered, washed twice with ether, dried and finally recrystallized from CH$_2$Cl$_2$. Yield 1.68 g (59% with respect to Me$_2$Th). The desired title compound was characterized by $^1$H-NMR spectroscopy.

Example 30

Synthesis of 1-bromo-2-(3-indenyl)ethane

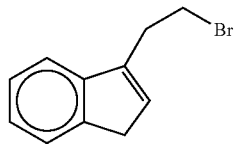

A 1.6 M n-BuLi solution in hexane (100 mL, 0.16 mol) was added at 0° C. to a solution of indene (18.6 g, MW=116.16, 0.16 mol) in 300 mL of ether. The resulting suspension was allowed to warm to room temperature and stirred for 4 h at the same temperature. Then the indenyl lithium suspension was cooled again to −50° C. and added of a solution of 1,2-dibromoethane (0.24 mol, 21 mL) in 50 mL of ether. The reaction mixture was allowed to warm up slowly to room temperature and stirred overnight. Then it was treated with a saturated aqueous solution of NH$_4$Cl. The organic phase was isolated, evaporated off to dryness and distilled in vacuo, b.p. 110° C./0.5 torr. Yield 21.6 g (60%). The title compound was characterized by NMR spectroscopy.

Synthesis of 1,2-(3-indenyl)-7-(2,5-dimethylcyclopenta[1,2-b:4,3-b']-dithiophene)ethane

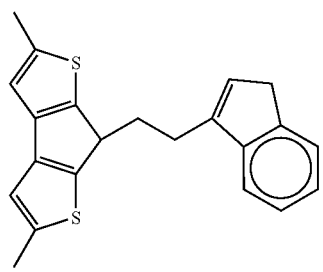

A solution of 2,5-dimethylcyclopenta[1,2-b:4,3-b']-dithiophene (1.03 g, 5 mmol) in 50 mL of THF was treated at −70° C. with a 1.6 M n-BuLi solution in hexane (3.1 mL, 5 mmol). The resulting mixture was stirred for additional 45 min at 0° C., then cooled again to −70° C. and treated with 1-bromo-2-(3-indenyl)ethane (1.12 g, 5 mmol) in 25 mL of THF. The reaction mixture was allowed to warm to room temperature and subsequently treated with a saturated aqueous solution of NH$_4$Cl. The organic phase was isolated and the solvents were removed. The residue was passed through a column packed with silica gel by using hexane as eluent. Yield 1.26 g (72%). The title compound was characterized by NMR spectroscopy.

Synthesis of ethylidene{(1-indenyl)-7-(2,5-dimethylcyclopenta[1,2-b:4,3-b']-dithiophene)}zirconium dichloride C-37

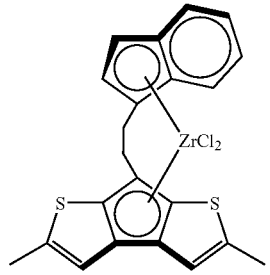

A solution of 1,2-(3-indenyl)-7-(2,5-dimethylcyclopenta[1,2-b:4,3-b']-dithiophene)ethane (1.26 g, 3.62 mmol) in 15 mL of ether and 60 mL of hexane was treated at −70° C. with a 1.6 M n-BuLi solution in hexane (4.7 mL, 7.5 mmol). The resulting suspension was stirred for additional 2 h at room temperature, then cooled again to −70° C. and added of ZrCl$_4$ (0.94 g, 4 mmol). The reaction mixture was allowed to warm to room temperature and stirred overnight. The dark orange precipitate was filtered, washed twice with ether, dried and then recrystallyzed from CH$_2$Cl$_2$. Yield 0.92 g (50%).

$^1$H-NMR (δ, ppm, CD$_2$Cl$_2$): 7.70 (dd, 1H, CH); 7.45 (dd, 1H, CH); 7.20 (m, 1H, CH); 7.10 (m, 1H, CH); 6.75 (q, 1H, CH); 6.60 (q, 1H, CH); 6.55 (dd, 1H, CH); 6.40 (d, 1H, CH); 3.95–3.80 (m, 2H, CH$_2$); 3.65–3.55 (m, 2H, CH$_2$); 2.60 (d, 3H, CH$_3$); 2.45 (d, 3H, CH$_3$).

Example 31

Synthesis of chloro(4,7-dimethyl-1-indenyl)dimethylsilane

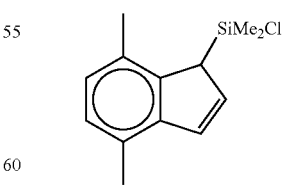

The precursor 4,7-dimethylindene was prepared by following standard procedure (as reported in Tetrahedron, 51, (1995), 4347).

A 1.6 M n-BuLi solution in hexane (62.5 mL, 0.1 mol) was added at 0° C. to a solution of 4,7-dimethylindene (14.42 g, MW=144.22, 0.1 mol) in 200 mL of hexane and 50 mL of THF. The resulting suspension was allowed to warn to room temperature and stirred for 4 h at the same temperature. Then the indenyl lithium suspension was cooled again to −50° C. and added of a solution of dichlorodimethylsilane (0.2 mol, 24 mL) in 50 mL of THF. The resulting suspension was allowed to warm to room temperature and stirred overnight. The precipitate of lithium chloride was filtered, the filtrate was evaporated off to dryness and distilled in vacuo, b.p. 98° C. 0.5 torr. Yield 16.5 g (70%). The title compound was characterized by NMR spectroscopy.

Synthesis of (4,7-dimethyl-1-indenyl)-7-(2,5-dimethylcyclopenta[1,2-b:4,3-b']-dithiophene)dimethylsilane

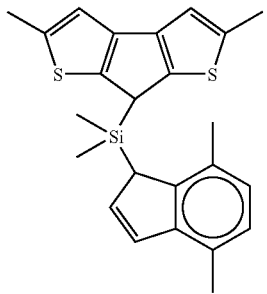

A solution of 2,5-dimethylcyclopenta[1,2-b:4,3-b']-dithiophene (1.90 g, 9.2 mmol) in 50 mL of ether was treated at −70° C. with a 1.6 M n-BuLi solution in hexane (5.8 mL, 9.2 mmol). The resulting mixture was stirred for additional 45 min at 0° C., then cooled again to −70° C. and treated with chloro(4,7-dimethyl-1-indenyl)dimethylsilane (2.18 g, 9.2 mmol) in 10 mL of ether. The reaction mixture was allowed to warm to room temperature and subsequently treated with a saturated aqueous solution of NH$_4$Cl. The organic phase was isolated and the solvents were removed. The residue was recrystallysed from hexane. Yield 3.67 g (98%).

$^1$H-NMR (δ, ppm, CDCl$_3$): 7.07 (dd, 1H, CH); 7.05 (d, 1H, CH); 6.95 (d, 1H, CH); 6.90 (m, 2H, CH); 6.60 (dd, 1H, CH); 4.00 (s, 1H, CH); 3.85 (s, 1H, CH); 2.64 (s, 3H, CH$_3$); 2.60 (s, 3H, CH$_3$); 2.50 (s, 3H, CH$_3$); 2.40 (s, 3H, CH$_3$); −0.20 (3H, Si—CH$_3$); −0.40 (s, 3H, Si—CH$_3$).

Synthesis of dimethylsily{(4,7-dimethyl-1-indenyl)-7-(2,5-dimethylcyclopenta[1,2-b:4,3-b']-dithiophene)}zirconium dichloride C-38

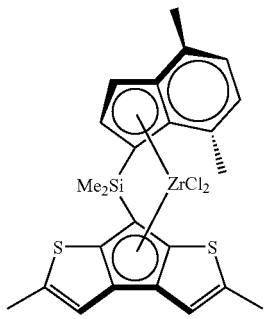

A solution of (4,7-dimethyl-1-indenyl)-7-(2,5-dimethylcyclopenta[1,2-b:4,3-b']-dithiophene)dimethylsilane (3.67 g, 9.02 mmol) in 15 mL of ether and 50 mL of hexane was treated at −70° C. with a 1.6 M n-BuLi solution in hexane (12.5 mL, 20 mmol). The resulting suspension was stirred for additional 2 h at room temperature, then cooled again to −70° C. and added of ZrCl$_4$ (2.52 g, 10.8 mmol). The reaction mixture was allowed to warm to room temperature and stirred overnight. The yellow precipitate was filtered, washed twice with ether, dried and then recrystallyzed from CH$_2$Cl$_2$. Yield 3.57 g (70%). The title compound was characterized by NMR spectroscopy.

Example 32

Synthesis of-chloro(2,4,7-trimethyl-1-indenyl)dimethylsilane

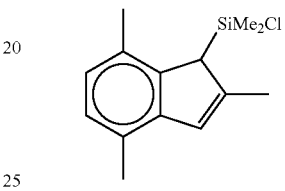

The precursor 2,4,7-trimethylindene was prepared by following standard procedure (as reported in Eur. Pat. Appl. 0693506).

A 1.6 M n-BuLi solution in hexane (37.5 mL, 60 mmol) was added at 0° C. to a solution of 2,4,7-trimethylindene (9.5 g, MW=158.24, 60 mmol) in 200 mL of hexane and 50 mL of THF. The resulting suspension was allowed to warm to room temperature and stirred for 4 h at the same temperature. Then the indenyl lithium suspension was cooled again to −50° C. and added of a solution of dichlorodimethylsilane (90 mmol, 11 mL) in 50 mL of THF. The resulting suspension was allowed to warm to room temperature and stirred overnight. The precipitate of lithium chloride was filtered, the filtrate was evaporated off to dryness and distilled in vacuo, b.p. 110° C./0.5 torr. Yield 10.1 g (67%).

$^1$H-NMR (δ, ppm, C$_6$D$_6$): 6.75 (d, 1H, CH); 6.60 (d, 1H, CH); 6.30 (s, 1H, CH); 3.25 (s, 1H, CH); 2.25 (s, 3H, CH$_3$); 2.15 (s, 3H, CH$_3$); 2.10 (s, 3H, CH$_3$); −0.05 (s, 3H, Si—CH$_3$); −0.02 (s, 3H, Si—CH$_3$).

Synthesis of (2,4,7-trimethyl-1-indenyl)-7-(2,5-dimethylcyclopenta[1,2-b:4,3-b']-dithiophene)dimethylsilane

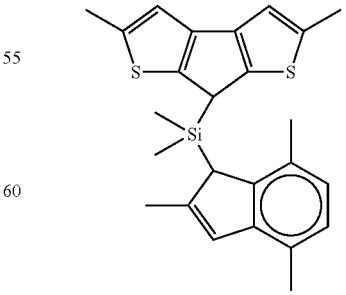

A solution of 2,5-dimethylcyclopenta[1,2-b:4,3-b']-dithiophene (1.65 g, 8 mmol) in 50 mL of ether was treated at −70° C. with a 1.6 M n-BuLi solution in hexane (5.0 mL, 8 mmol). The resulting mixture was sired for additional 45 min at 0° C., then cooled again to −70° C. and treated with chloro(2,4,7-trimethyl-1-indenyl)dimethylsilane (2.0 g, 8 mmol) in 20 mL of ether. The reaction mixture was allowed to warm to room temperature and subsequently treated with a saturated aqueous solution of NH$_4$Cl. The organic phase was isolated and the solvents were removed. Yield 3.36 g (~100%).

$^1$H-NMR (δ, ppm, CDCl$_3$): 6.90 (d, 1H, CH); 6.80 (d, 1H, CH); 6.70 (m, 2H, CH); 6.65 (m, 1H, CH); 4.15 (s, 1H, CH); 4.00 (s, 1H, CH); 2.65 (s, 3H, CH$_3$); 2.63 (s, 3H, CH$_3$); 2.55 (s, 3H, CH$_3$); 2.50 (s, 3H, CH$_3$); 2.20 (s, 3H, CH$_3$); −0.15 (s, 3H, Si—CH$_3$); −0.30 (s, 3H, Si—CH$_3$).

Synthesis of dimethylsilyl{(2,4,7-trimethyl-1-indenyl)-7-(2,5-dimethylcyclopenta[1,2-b:4,3-b']-dithiophene)}zirconium dichloride C-39

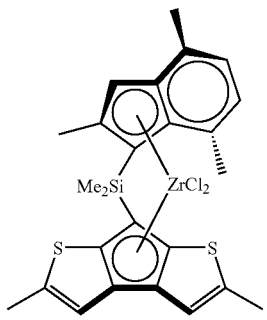

A solution of (2,4,7-trimethyl-1-indenyl)-7-(2,5-dimethylcyclopenta[1,2-b:4,3-b']-dithiophene)dimethylsilane (3.36 g, 8.0 mmol) in 80 mL of ether was treated at −70° C. with a 1.6 M n-BuLi solution in hexane (12.5 mL, 20 mmol). The resulting suspension was stirred for additional 2 h at room temperature, then cooled again to −70° C. and added of ZrCl$_4$ (2.34 g, 10 mmol). The reaction mixture was allowed to warm to room temperature and stirred overnight. The orange precipitate was filtered, washed twice with ether, dried and then recrystallyzed from CH$_2$Cl$_2$. Yield 2.73 g (59%). The title compound was characterized by NMR spectroscopy. cl Example 33

Synthesis of 2-methyl-2,3-dihydro-1H-cyclopenta[a]naphtalen-1-one

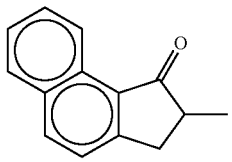

To a suspension of AlCl$_3$ (85 g, 0.635 mol) in 200 mL of CH$_2$Cl$_2$ were added at 0° C. first naphalene (32.5 g, 0.254 mol) and then a solution of 2-methylacryloyl chloride (26.5 g, 0.254 mol) in 50 mL of CH$_2$Cl$_2$. The reaction mixture was stirred for 30 min at 0° C., then 2 h at room temperature and finally poured into a mixture of ice and water. The dark organic layer was separated, while the water layer was extracted with CHCl$_3$ (3×150 mL). The organic layers were collected, washed with potassium carbonate/water until neutral pH, dried over MgSO$_4$ and evaporated off to dryness. Yield 28.09 g (56%). The title compound was characterized by NMR spectroscopy.

Synthesis of 2-methyl-2,3-dihydro-1H-cyclopenta[a]naphtalen-1-ol

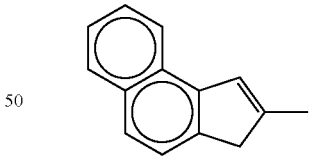

A solution of 2-methyl-2,3-dihydro-1H-cyclopenta[a]naphtalen-1-one (28.09 g, 0.143 mol) in 100 mL of THF was slowly added to a suspension of LiAlH$_4$ (2.18 g, 58 mmol) in 200 mL of ether and refluxed for 2 h under stirring. The reaction mixture was subsequently transferred into a 2-L beaker and slowly hydrolyzed, under constant stirring, by dropwise addition of a 10% aq. solution of HCl until pH 5. The organic layer was separated, while the water layer was extracted with ether (3×100 mL). The organic layers were collected, washed with potassium carbonate/water until neutral pH, dried over MgSO$_4$ and evaporated off to dryness. The so-obtained product, as a mixture of two isomers, was used in the next step without further purification.

Synthesis of 2-methyl-3H-cyclopenta[a]naphtalene

A mixture of 2-methyl-2,3-dihydro-1H-cyclopenta[a]naphthalen-1-ol (obtained as described above) and 1 g of p-toluenesulphonic acid in 200 mL of benzene was refluxed for 1 h. Then the reaction mixture was cooled to room temperature and treated with a saturated aqueous solution of Na$_2$CO$_3$. The organic phase was isolated, dried over MgSO$_4$ and evaporated off to dryness. Yield 14.2 g (55% based on starting 2-methyl-2,3-dihydro-1H-cyclopenta[a]naphtalen-1-one).

$^1$H-NMR (δ, ppm, CDCl$_3$): 8.10–7.40 (m, 6H, CH); 7.10 (m, 1H, CH); 3.50 (s, 2H, CH$_2$); 2.33 (s, 3H, CH$_3$).

Synthesis of chloro(2-methyl-3H-cyclopenta[a]naphthalen-3-yl)dimethylsilane

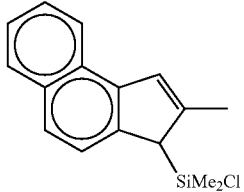

A 1.6 M n-BuLi solution in hexane (7.5 mL, 12 mmol) was added at −50° C. to a solution of 2-methyl-3H-cyclopenta[a]naphthalene (2.14 g, MW=180.25, 11.9 mmol) in 50 mL of ether. The resulting suspension was allowed to warm to room temperature and stirred for 45 min at the same temperature. Then the lithium suspension was cooled again to −70° C. and added of dichlorodimethylsilane (18 mmol, 2.2 mL). The reaction mixture was allowed to warm to room temperature and stirred overnight. The precipitate of lithium chloride was filtered, the filtrate was evaporated off to dryness and dried in vacuo. Yield 3.14 g (97%).

$^1$H-NMR (δ, ppm, $C_6D_6$): 8.10 (d, 1H, CH); 7.85 (d, 1H, CH); 7.50–7.40 (m, 4H, CH); 7.10 (s, 1H, CH); 3.55 (s, 1H, CH); 2.30 (s, 3H, $CH_3$); 0.22 (s, 3H, Si—$CH_3$); −0.05 (s, 3H, Si—$CH_3$).

Synthesis of (2-methylcyclopenta[a]naphthalen-3-yl)-7-(2,5-dimethylcyclopenta[1,2-b:4,3-b']-dithiophene)dimethylsilane

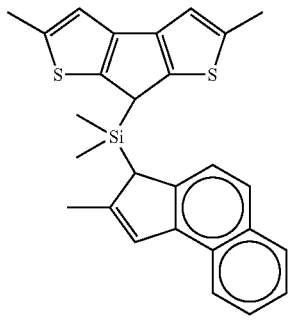

A solution of 2,5-dimethylcyclopenta[1,2-b:4,3-b']-dithiophene (2.37 g, 11.5 mmol) in 75 mL of ether was treated at −70° C. with a 1.6 M n-BuLi solution in hexane (7.5 mL, 12 mmol). The resulting mixture was stirred for additional 45 min at 0° C., then cooled again to −70° C. and treated with chloro(2-methyl-3H-cyclopenta[a]naphthalen-3-yl)dimethylsilane (3.14 g, 11.5 mmol) in 25 mL of ether. The reaction mixture was allowed to warm to room temperature and subsequently treated with a saturated aqueous solution of $NH_4Cl$. The organic phase was isolated and the solvents were removed. The residue was passed through a short column packed with silica gel by using hexane as eluent. Yield 4.07 g (80%).

$^1$H-NMR (δ, ppm, $CDCl_3$): 8.20 (d, 1H, CH); 8.00 (d, 1H, CH); 7.70–7.40 (m, 4H, CH); 6.95 (d, 2H, CH); 6.80 (s, 1H, CH); 4.20 (s, 1H, CH); 4.15 (s, 1H, CH); 2.66 (s, 6H, $CH_3$); 2.45 (s, 3H, $CH_3$); −0.27 (s, 3H, Si—$CH_3$); −0.29 (s, 3H, Si—$CH_3$).

Synthesis of dimethylsilyl{(2-methylcyclopenta[a]naphthalene)-7-(2,5-dimethylcyclopenta[2-b:4,3-b']-dithiophene)}zirconium dichloride C-40

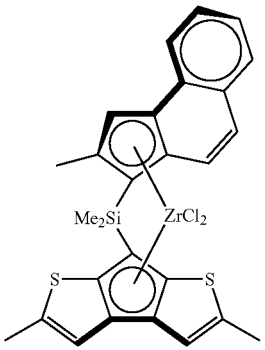

A solution of (2-methylcyclopenta[a]naphthalen-3-yl)-7-(2,5-dimethylcyclopenta[1,2-b:4,3-b']-dithiophene)dimethylsilane (4.07 g, 9.2 mmol) in 100 mL of ether was treated at −70° C. with a 1.6 M n-BuLi solution in hexane (15 mL, 24 mmol). The resulting suspension was stirred for additional 2 h at room temperature, then cooled again to −70° C. and added of $ZrCl_4$ (2.79 g, 12 mmol). The reaction mixture was allowed to warm to room temperature and stirred overnight. The orange precipitate was filtered, washed twice with ether, dried and then recrystallyzed from $CH_2Cl_2$. Yield 2.77 g (50%).

$^1$H-NMR (δ, ppm, $CD_2Cl_2$): 8.00 (d, 1H, CH); 7.70 (d, 1H, CH); 7.60 (d, 1H, CH); 7.55 (t, 1H, CH); 7.48 (t, 1H, CH); 7.25 (s, 1H, CH); 7.15 (d, 1H, CH); 6.78 (q, 1H, CH); 6.65 (q, 1H, CH); 2.60 (d, 3H, CH3); 2.55 (d, 3H, $CH_3$); 2.40 (d, 3H, $CH_3$); 1.32 (s, 3H, Si—$CH_3$); 1.18 (s, 3H, Si—$CH_3$).

Example 34

Synthesis of dimethylsily {(1-indenyl)-7-(2,5-ditrimethylsilyl-cyclopenta[1,2-b:4,3-b']-dithiophene)}zirconium dichloride C-13

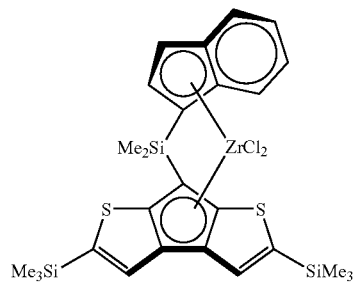

The C13-ligand synthesis was carried out by coupling the lithium salt of 2,5-ditrimethylsilyl-7H-cyclopenta[1,2-b:4,3-b']dithiophene with chloro(1-indenyl)dimethyl silane. A suspension of 1.48 g (3 mmol) of (1-indenyl)-7-{(2,5-ditrimethylsilyl-cyclopenta[1,2-b:4,3-b']dithiophene)} dimethylsilane in 50 mL of ether was treated at −70° C. with 4.1 mL of a 1.6 M n-BuLi solution (6.5 mmol). After the addition, the reaction mixture was allowed to warm to 0° C. and added of 0.75 g (3.2 mmol) of $ZrCl_4$. The resulting mixture was allowed to reach room temperature and stirred overnight. Then the red precipitate obtained was filtered, washed twice with ether, dried and finally recrystallyzed from $CH_2Cl_2$. Yield 1.38 g (70%).

$^1$H-NMR (δ, ppm, $CD_2Cl_2$): 7.90–6.90 (m, 7H, CH); 6.10 (m, 1H, CH); 1.40 (s, 3H, Si—$CH_3$); 1.10 (s, 3H, Si—$CH_3$); 0.41 (s, 9H, Si$(CH_3)_3$); 0.20 (s, 9H, Si$(CH_3)_3$).

Example 35

Synthesis of (3-methyl-4-trimethylsilyl-1-cyclopentadienyl)-7-(2,5-dimethyl-cyclopenta[1,2-b:4,3-b']-dithiophene)dimethylsilane

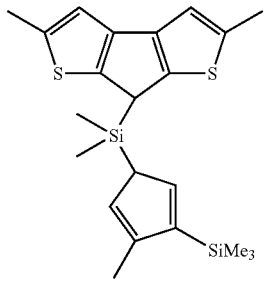

A solution of 1.03 g (5.0 mmol) of 2,5-dimethyl-7H-cyclopenta[1,2-b:4,3-b']-dithiophene in 40 mL of ether was treated at −70° C. with 3.13 mL of a 1.6 M n-BuLi solution (5.0 mmol). After the addition, the mixture was allowed to warm to room temperature and stirred for additional 1 h at this temperature. Then it was cooled again to −70° C. and added of a solution of 1.22 g (5 mmol) of chlorodimethyl (3-methyl-4-trimethylsilyl-1-cyclopentadienyl)silane in 10 mL of ether. The resulting mixture was allowed to reach room temperature and stirred overnight. The ligand (3-methyl-4-trimethylsilyl-1-cyclopentadienyl)-7-(2,5-dimethyl-cyclopenta[1,2-b:4,3-b']-dithiophene)dimethylsilane was not isolated, but used in solution for the catalysts synthesis (see below).

Synthesis of dimethylsilyl{(3-methyl-4trimethylsilyl-1-cyclopentadienyl)-7-(2,5-dimethyl-cyclopenta[1,2-b:4,3-b']-dithiophene)}zirconium dichloride [C-32]

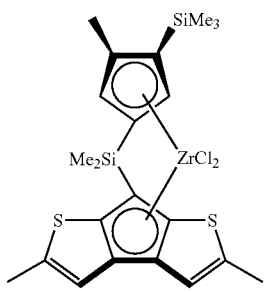

The ligand solution coming from the previous step was treated at −70° C. with 6.3 mL of a 1.6 M n-BuLi solution (10.1 mmol). After the addition, the reaction mixture was allowed to reach room temperature and stirred for additional 50 min at this temperature. The solvent was removed under reduced pressure and the dilithium salt obtained was suspended in hexane. After cooling to −70° C., 1.17 g (5.0 mmol) of $ZrCl_4$ were added. The reaction mixture was stirred at room temperature overnight, the yellow precipitate was filtered, washed twice with hexane, dried and finally recrystallized from $Et_2O$. Yield 0.90 g (31%).

$^1$H-NMR (δ, ppm, $CD_2Cl_2$): 6.95 (q, 1H, CH, J=1.17 Hz); 6.91 (q, 1H, CH, J=1.17 Hz); 5.77 (d, 1H, CH, J=2.74 Hz); 5.68 (d, 1H, CH, J=2.74 Hz); 2.62 (q, 3H, $CH_3$, J=1.17 Hz); 2.59 (q, 3H, $CH_3$, J=1.17 Hz); 2.22 (s, 3H, $CH_3$); 0.91 (s, 3H, Si—$CH_3$); 0.89 (s, 3H, Si—$CH_3$); 0.22 (s, 9H, Si—$(CH_3)_3$).

Polymerization Examples

General Procedures

The cocatalyst methylalumoxane (MAO) was a commercial product which was used as received (Witco AG, 10% wt/vol toluene solution, 1.7 M in Al). The catalyst mixture was prepared by dissolving the desired amount of the metallocene with the proper amount of the MAO solution, obtaining a solution which was stirred for 10 min at ambient temperature before being injected into the autoclave.

Polymerization Examples 1–33 Propylene Polymerization 1 mmol of Al(i-Bu)$_3$ (as a 1M solution in hexane) and 290 g of propylene were charged at room temperature in a 1-L jacketed stainless-steel autoclave, equipped with magnetically driven stirrer and a 35-mL stainless-steel vial, connected to a thermostat for temperature control, previously purified by washing with an Al(i-Bu)$_3$ solution in hexanes and dried at 50° C. in a stream of propene. The autoclave was then thermostatted at 2° C. below the polymerization temperature, and then the toluene solution containing the catalyst/cocatalyst mixture was injected in the autoclave by means of nitrogen pressure through the stainless-steel vial, the temperature rapidly raised to the polymerization temperature and the polymerization carried out at constant temperature for 1 hour. After venting the unreacted monomer and cooling the reactor to room temperature, the polymer was dried under reduced pressure at 60 ° C. The polymerization conditions and the characterization data of the obtained polymers are reported in Table 1.

Polymerization Example 34 Propylene/Butene Copolymerization

Operating as in the case of propylene homopolymerizations, 1 mmol of Al(i-Bu)$_3$ (as a 1M solution in hexane), 160 g of propylene and 154 g of 1-butene were charged at room temperature in the 1-L jacketed stainless-steel autoclave, thermostatted at 58° C., in order to have a 50/50 mol % in the liquid phase, and then the toluene solution containing the catalyst/cocatalyst mixture (0.5 mg of C-20, 0.45 mmol of MAO, in 3 mL of toluene) was injected in the autoclave by means of nitrogen pressure through the stainless-steel vial, the temperature rapidly raised to the polymerization temperature and the polymerization carried out at constant temperature for 1 hour. 26.5 g of essentially amorphous polymer were recovered, which has I.V.=2.29 dL/g, $T_g$=−13.6° C., and butene=27.7 wt % (22.3 mol %).

Polymerization Example 35 Propylene/Ethylene Copolymerization

Operating as in the case of propylene homopolymerizations, 1 mmol of Al(i-Bu)$_3$ (as a 1M solution in hexane), propylene and ethylene were charged at room temperature in the 1-L jacketed stainless-steel autoclave, thermostatted at 58° C., in order to have a liquid phase composition of 288 g propylene and 1.5 g ethylene (0.42% wt) in the liquid phase, and then the toluene solution containing the catalyst/cocatalyst mixture (0.3 mg of C-20, 0.27 mmol of MAO, in 3 mL of toluene) was injected in the autoclave by means of nitrogen pressure through the stainless-steel vial, the temperature rapidly raised to the polymerization temperature and the polymerization carried out at constant temperature and pressure (25 bar-g) by feeding ethylene (13.3 g total absorption) for 1 hour. 52.7 g of essentially amorphous polymer were recovered, which has I.V.=1.23 dL/g, and ethylene=6.3 wt % (9.2 mol %).

Polymerization Example 36 Propylene Polymerization with Supported Catalyst a) Preparation of the Supported Catalyst The apparatus used for the supportation is a glass cylindrical vessel mechanically stirred in order to allow a good mixing between the carrier and the catalytic solution during the impregnation operation. 6 g of a porous polyethylene having I.V. 21 dL/g, mean Particle size 386 μm and porosity 50.9% VN (1.07 cc/g) was loaded into the vessel and mechanically suspended under nitrogen flow. The catalytic solution was prepared by dissolving 24 mg of C-20 in 12 mL of a MAO solution (WITCO, 100 g/L in toluene). Due to the limited porosity of the carrier the liquid is dropped onto the solid until the incipient wetness condition is reached. At this point the solvent is evaporated off under vacuum. All the operations are carried out at room temperature. The catalytic solution is then added to the carrier step by step. The final catalyst appears as a pink-violet free flowing solid with the following composition: Al 5.0% w and Zr 0.0705% w (Al/Zr molar ratio 240).

b) Polymerization

A 4L stainless-steel reactor, equipped with a blade turbine magnetic stirrer, pressure indicator, temperature indicator and a thermosetting jacket, was used. A batch polymerization was carried with the following procedure. 1200 g of liquid monomer was loaded at 30° C., followed by 3 ml of a TIBA solution 100 g/l in hexane used as a scavenger. The polymerization was started by injecting 305 mg of the catalyst into the autoclave at 30° C., by means of nitrogen overpressure, then the temperature was raised up to 60° C. in 10 minutes and maintained for 1 hour. The polymerization was stopped by venting and cooling the reactor. No significant fouling was observed. The product obtained was collected and dried in an oven flushed with nitrogen at 70° C. for 3 hours. 360 g of polymer was obtained with a good morphology having an I.V. of 1.94 dL/g. The activity of the catalyst was 1.2 kg PP/g cat supp.h, corresponding to 1.7 ton PP/gZr.h.

d) Physical Characterization

The polymer was additivated with the reported stabilisation formula and pelletised with the following processing parameters:

Stabilisation Formula

| Components | Kg |
|---|---|
| CALCIUM STEARATE M | 0.0500 |
| FLI-PP | 99.7500 |
| IRGANOX B215/ANOX BB 021 | 0.1500 |
| VASELIN OIL OB 30 | 0.0500 | single screw extruder: MACGI 14 mm diameter

Cylinder Temperature: 230° C.

Feeding Temperature: 230° C.

Screw speed: 50 rpm

The so obtained pellets were compression moulded with Carver press

Compression moulding:

Plaque thickness:

| | |
|---|---|
| Haze, Gloss, DMTA: | 1.0 mm |
| Tensile test: | 2.0 mm |
| Notched Izod: | 3.2 mm |

Press Plaque Temperature: 200° C.
Preheating time (no press): 5 min
Pressure time: 5 min
Pressure: 14 bar
Cooling: rapid in ice/water bath The plaques, after compression moulding were stored at room temperature at least 48 hours before characterisation.

DSC measurement: obtained with a Mettler calorimeter with the following procedure:

First run: Heating the sample from −120 to 200° C. at 20° C./min

Crystallisation: Cooling from 200° C. to −120° C. at 20° C./min

Second run: Heating the sample from −120 to 200° C. at 20° C./min

The physical characterization of the polymer is reported at table 2.

Polymerization Examples 37–59 Ethylene/Propylene Polymerization

The Ethylen Propylene mixtures were prepared in a 5 L steel cylinder, filled with quantities of the two gases small enough to prevent their condensation. The composition of the gaseous mixture in the cylinder was controlled through GC analysis. The copolymerizations were carried out at 50° C. in a 250 mL glass reactor equipped with a mechanical stirrer, an Allihn condenser, a thermometer and a pipe for monomers feeding, and kept in a thermostatic bath. First, 100 mL of toluene and 3.5 mmol of TIOAO solution were introduced into the nitrogen-purged reactor. At the polymerization temperature, the nitrogen was removed and replaced with the comonomers mixture, with a flow rate of 1.5 L/min. When the equilibrium pressure (1.1 atm of total pressure) was reached, 3.5 μmol of the metallocene dissolved in 5 mL of hexane in the presence of a 35 μmol of TIOA (35 μL of solution 1 M), was added to start the polymerization. During the reaction, the temperature was kept within 50±1° C. After 15 min the polymerization was quenched by adding 1 mL of methanol, and the copolymer was precipitated with 300 mL of methanol acidified with HCl, filtered, washed and dried overnight in vacuo at 50° C. Polymerization results characterization and reactivity ratios r1 and r2 of ethylene/propylene copolymers are reported in tables 3, 4 and 5.

ethylene partial pressure also was increased to 10 bar. The polymerization was stopped after 2 hours by venting and cooling the reactor. The polymer discharged was dried in an oven flushed with nitrogen at 70° C. for 3 hours. 90 g of polymer was obtained with an intrinsic viscosity of 4.29 dL/g and a melting temperature of 141.40° C.

TABLE 1 propylene polymerization

| Ex. | Cat. | mg | Yield | Activity kg/(gcat.h) | MAO/Zr molar | I.V. THN (dL/g) | Tm (° C.) | AH (J/g) | mm % |
|---|---|---|---|---|---|---|---|---|---|
| 1* | C-0 | 2 | 147 | 73 | 3000 | 0.65 | amorphous | — | 6.7 |
| 2 | C-1 | 0.8 | 87 | 153 | 3000 | 0.54 | 80 | 13 | 58.7 |
| 3 | CH-1 | 2 | 23 | 12 | 1000 | 0.77 | amorphous (TmI = 63) | 20 | 55.5 |
| 4* | C-3 | 1 | 61 | 122 | 3000 | 0.58 | 139 | 91 | 89.2 |
| 5* | C-4 | 1 | 24 | 24 | 1000 | 0.19 | 148 | 98 | 94.3 |
| 6* | C-5 | 0.5 | 69.2 | 138 | 1000 | 0.57 | amorphous | — | 24.8 |
| 7 | C-2 | 0.3 | 87 | 290 | 500 | 0.82 | 103 | 40 | 73.1 |
| 8 | C-8 | 1 | 31 | 30 | 500 | 0.64 | — | — | 50.6 |
| 9 | C-16 | 1 | 44 | 44 | 500 | 0.74 | amorphous | — | 54 |
| 10 | C-7 | 1 | 81 | 81 | 500 | 0.88 | 107 | 47 | 76 |
| 11 | C-17 | 1 | 120 | 120 | 500 | 1.06 | 80 | 19 | 66.5 |
| 12 | C-9 | 1 | 300 | 300 | 500 | 0.72 | amorphous | — | 30.8 |
| 13 | C-19 | 1 | 160 | 190 | 500 | 0.83 | amorphous | — | — |
| 14 | C-11 | 1 | 240 | 240 | 500 | 0.9 | amorphous | — | 42.6 |
| 15 | C-14 | 1 | 13 | 13 | 500 | 0.84 | amorphous | — | — |
| 16 | C-12 | 1 | 94 | 94 | 500 | 0.79 | amorphous | — | — |
| 17 | C-18 | 1 | 64 | 64 | 500 | 1.24 | 123 | 62 | 84 |
| 18 | C-15 | 1 | 60 | 119 | 500 | 0.8 | amorphous | — | — |
| 19 | C-10 | 1 | 36 | 36 | 500 | 1.25 | 114 | 61 | 79.9 |
| 20 | C-36 | 1 | 42 | 41.9 | 500 | 1.43 | 93 | 28 | 72 |
| 21 | C-20 | 1 | 79 | 79 | 500 | 2.34 | 115 | 50 | 82.1 |
| 22 | C-34 | 1 | 63 | 63 | 500 | 1.69 | 120 | 61 | 82.3 |
| 23 | C-35 | 1 | 12 | 12 | 500 | 1.42 | — | — | — |
| 24§ | C-28 | 2.5 | 125 | 50 | 1000 | 1.19 | 146 | 88 | 93.7 |
| 25§ | C-31 | 3.5 | 150 | 43 | 1000 | 0.55 | 111 | 55 | 77.1 |
| 26§ | C-27 | 2.4 | 320 | 133 | 1000 | 1.24 | 126 | 73 | 84.9 |
| 27 | C-29 | 0.3 | 38 | 138 | 500 | 2.38 | 123 | 67 | — |
| 28§ | C-30 | 2.4 | 490 | 204 | 1000 | 0.86 | 137 | 83 | 90.5 |
| 29 | C-33 | 1 | 87 | 87 | 500 | 1.86 | 139 | 86 | 91.7 |
| 30# | C-37 | 2 | 39 | 19.5 | 500 | 1.29 | 121 | 67 | 84.6 |
| 31# | C-38 | 1 | 74 | 74 | 500 | 1.48 | 121 | 70 | 81.8 |
| 32# | C-39 | 1 | 148 | 148 | 500 | 1.75 | 137 | 82 | 90.4 |
| 33# | C-40 | 1 | 140 | 140 | 500 | 2.09 | 119 | 63 | 82.9 |

Polymerization was carried out at 60° C. For examples 2 and 6 the polymerization time is 0.75 hour; for examples 14 the time is 0.85 hour; for example 27 the time is 0.92 hour; for all the other examples the polymerization time is 1 hour.
*Comparative
Polymerization was carried out in a 2 L reactor with 620 g of liquid propylene
§Polymerization was carried out in a 4 L reactor with 1200 g of liquid propylene Polymerization Example 60 Ethylene Polymerization with Supported Catalyst A 4L stainless-steel reactor, equipped with a blade turbine magnetic stirrer, pressure indicator, temperature indicator, feed line for monomer equipped with a thermal-mass flow-meter for the measure of the ethylene uptake and a thermosetting jacket, was used. A batch polymerization was carried out with the following procedure. 1600 ml of liquid propane is loaded into the reactor at 30° C., followed by 2.5 mmoles of tri-isobutylaluminum as the scavenger. The autoclave was pressurized with an ethylene partial pressure of 5 bar. The polymerization was started by injecting 162 mg of the catalyst prepared in example 37 a) into the autoclave at 30° C., by means of nitrogen overpressure. A prepolymerization step was carried out at 30° C. for 30 minutes. After this time the reactor temperature was increased up to 75° C. and the

TABLE 2 polypropylene characterization

| Description | Units | Value |
|---|---|---|
| Melt Flow Rate "L" METHOD ASTM D1238 | g/10' | 2.100 |
| HAZE on 1 mm compresion moulded plaque METHOD ASTM D1003 | % | 26.0 |
| GLOSS (60 °) HAZE on 1 mm Compresion moulded plaque METHOD ASTM 2457 | % | 81.0 |
| DSC measurement: | | |
| Melting temperature (second run) | ° C. | 113.6 |
| Melting enthalpy (second run) | J/g | 56.7 |
| CRISTALLIZZATION temperature | ° C. | 71.5 |
| Crystallisation enthalpy | J/g | 57.5 |

TABLE 2-continued polypropylene characterization

| Description | Units | Value |
|---|---|---|
| Dynamical mechanical analysis DMTA - tensile configuration METHOD ASTM D4065 | | |
| Tensile modulus at 23° C. | Mpa | 500 |
| temperaturerature gradient | C./min | 2.0 |
| Compresion moulded plaque | Quenched Thickness | 1 mm |
| Glass transition temperature | ° C. | 10 |
| Tensile test: Elongational properties - METHOD ASTM D638 | | |
| Elongation at break | % | 670 |
| Elongation at yield | % | 21.0 |
| Strength at break | Mpa | 27.0 |
| Strength at yield | Mpa | 16.0 |
| Specimen width | mm | 5.98 |
| SPAN | mm | 25 |
| TEMPERATURE | ° C. | 23 |
| Elongation speed | mm/min | 500.00 |
| RHEOLOGY MEASUREMENTS VIA DYNAMIC VISCOSIMETRY | | |
| Polydispersity Index | — | 2.4 |
| Frequency range | | 0.01–100 rad/s |
| TEMPERATURe | ° C. | 200.0 |

TABLE 3

Ethylene/propylene copolymerization with thiocene/TIOAO catalytic systems

| | | Ethylene/Propylene[a] | | | | Copolymer |
|---|---|---|---|---|---|---|
| Ex. | Metallocene | gas phase mol/mol | liquid phase mol/mol | Activity $Kg_{pol}/g_{cat}h$ | I.V. [η] dL/g | Composition[b] Ethylene, % wt |
| 37 | C-4 | 2.46 | 0.582 | 1.2 | 2.01 | 79.25 |
| 38 | C-4 | 1.16 | 0.274 | 0.4 | 0.90 | 66.94 |
| 39 | C-9 | 2.60 | 0.614 | 3.7 | 1.09 | 72.59 |
| 40 | C-9 | 1.17 | 0.277 | 0.5 | n.m.[c] | 68.29 |
| 41 | C-13 | 2.21 | 0.522 | 0.8 | 1.50 | 90.33 |
| 42 | C-13 | 1.16 | 0.274 | 0.2 | 1.00 | 82.57 |
| 43 | C-20 | 2.60 | 0.614 | 3.4 | 1.50 | 72.08 |
| 44 | C-20 | 1.17 | 0.277 | 8.4 | 0.96 | 53.96 |
| 45 | C-27 | 2.52 | 0.596 | 7.7 | 1.85 | 63.49 |
| 46 | C-27 | 1.19 | 0.282 | 7.4 | 1.41 | 52.49 |
| 47 | C-29 | 2.52 | 0.596 | 3.9 | 2.15 | 71.00 |
| 48 | C-29 | 1.19 | 0.282 | 0.4 | 1.57 | 64.91 |
| 49 | C-30 | 1.82 | 0.432 | 3.3 | 1.35 | 74.34 |
| 50 | C-30 | 1.19 | 0.282 | 1.2 | 1.08 | 62.25 |
| 51 | C-32 | 1.82 | 0.432 | 4.5 | 1.94 | 84.31 |
| 52 | C-32 | 1.19 | 0.282 | 0.9 | 1.42 | 76.83 |
| 53 | C-32 | 1.82 | 0.432 | 5.1 | 1.73 | 79.37 |
| 54 | C-32 | 1.43 | 0.338 | 2.4 | 1.41 | 76.04 |
| 55 | C-33 | 1.82 | 0.432 | 2.5 | n.m.[c] | 77.51 |
| 56 | C-33 | 1.43 | 0.338 | 8.9 | 1.31 | n.m.[c] |
| 57 | C-34 | 1.82 | 0.432 | 9.4 | 0.88 | 57.00 |
| 58 | C-34 | 1.43 | 0.338 | 9.6 | 0.81 | 47.09 |
| 59 | C-35 | 1.82 | 0.432 | 0.3 | 1.31 | 75.32 |

[a]Molar ratio of the monomers in the gas and in the liquid phases
[b]from $^{13}$C NMR analysis.
[c]not measured.

TABLE 4

$^{13}$C NMR characterization of ethylene/propylene copolymers.

| Ex. | Metallocene | [E] | [PPP] | [PPE] | [EPE] molar fraction | [PEP] | [EEP] | [EEE] | $r_1 r_2$ |
|---|---|---|---|---|---|---|---|---|---|
| 37 | C-4 | 0.8514 | 0.0000 | 0.0386 | 0.1100 | 0.0181 | 0.2066 | 0.6267 | 0.92 |
| 38 | C-4 | 0.7523 | 0.0180 | 0.0844 | 0.1453 | 0.0725 | 0.2814 | 0.3984 | 0.91 |
| 39 | C-9 | 0.7989 | 0.0089 | 0.0524 | 0.1398 | 0.0363 | 0.2621 | 0.5005 | 0.75 |
| 40 | C-9 | 0.7636 | 0.0060 | 0.0694 | 0.1609 | 0.0589 | 0.2946 | 0.4101 | 0.62 |
| 41 | C-13 | 0.9334 | 0.0000 | 0.0190 | 0.0476 | 0.0000 | 0.1080 | 0.8254 | 2.85 |
| 42 | C-13 | 0.8766 | 0.0000 | 0.0502 | 0.0732 | 0.0118 | 0.1790 | 0.6858 | 2.45 |
| 43 | C-20 | 0.7948 | 0.0058 | 0.0682 | 0.1312 | 0.0291 | 0.2642 | 0.5015 | 0.96 |
| 44 | C-20 | 0.6374 | 0.0568 | 0.1628 | 0.1429 | 0.0811 | 0.2889 | 0.2674 | 1.07 |
| 45 | C-27 | 0.7229 | 0.0106 | 0.0974 | 0.1691 | 0.0735 | 0.2941 | 0.3553 | 0.66 |
| 46 | C-27 | 0.6237 | 0.0334 | 0.1588 | 0.1840 | 0.1091 | 0.2933 | 0.2213 | 0.59 |

TABLE 4-continued

<sup></sup>

| | | | | | | | | | |
|---|---|---|---|---|---|---|---|---|---|
| Ex. | Metallocene | [E] | [PPP] | [PPE] | [EPE] | [PEP] | [EEP] | [EEE] | $r_1r_2$ |
| | | | | | molar fraction | | | | |
| 47 | C-29 | 0.7860 | 0.0000 | 0.0620 | 0.1519 | 0.0381 | 0.2800 | 0.4679 | 0.63 |
| 48 | C-29 | 0.7351 | 0.0078 | 0.0843 | 0.1729 | 0.0541 | 0.3009 | 0.3801 | 0.58 |
| 49 | C-30 | 0.8129 | 0.0000 | 0.0598 | 0.1272 | 0.0357 | 0.2620 | 0.5152 | 0.91 |
| 50 | C-30 | 0.8326 | 0.0000 | 0.0193 | 0.1481 | 0.0239 | 0.2482 | 0.5605 | 0.27 |
| 51 | C-32 | 0.8896 | 0.0000 | 0.0048 | 0.1056 | 0.0197 | 0.1976 | 0.6723 | 0.16 |
| 52 | C-32 | 0.7121 | 0.0147 | 0.1133 | 0.1598 | 0.0624 | 0.3127 | 0.3370 | 0.79 |

TABLE 5

Reactivity ratios $r_1$ and $r_2$, and their product $r_1r_2$ for ethylene/propylene copolymerization

| Example | Metallocene | $r_1$ | $r_2$ | $r_1r_2$ |
|---|---|---|---|---|
| 37 | C-4 | 10.1 ± 0.3 | 0.08 ± 0.01 | 0.8 ± 0.1 |
| 39 | C-9 | 7.8 ± 1.2 | 0.06 ± 0.04 | 0.5 ± 0.4 |
| 41 | C-13 | 28.9 ± 0.7 | 0.09 ± 0.01 | 2.6 ± 0.4 |
| 43 | C-20 | 6.0 ± 0.2 | 0.16 ± 0.02 | 1.0 ± 0.1 |
| 45 | C-27 | 43 ± 0.4 | 0.13 ± 0.03 | 0.6 ± 0.2 |
| 47 | C-29 | 7.0 ± 1.0 | 0.07 ± 0.04 | 0.5 ± 0.3 |

The invention claimed is:

1. A metallocene compound of general formula (I):

LGZMXp      (I)

wherein

L is a divalent group bridging the moieties G and Z, selected from $CR^1R^2$, $SiR^1R^2$ or $(CR^1R^2)_2$, wherein $R^1$ and $R^2$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, which can form a ring having 3 to 8 atoms optionally bearing a substituent;

Z is a moiety of formula (II):

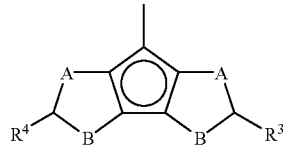

(II)

wherein $R^3$ and $R^4$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or $CR^5$, wherein $R^5$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom with the proviso that if A is S or O, then B is $CR^5$ or if B is S or O, then A is $CR^5$, and wherein either A or B is different than $CR^5$ and the rings containing A and B have a double bond in an allowed position;

G is a moiety of formula (III):

(III)

wherein $R^6$, $R^7$, $R^8$ and $R^9$, which may be the same as or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and at least one of substituent pairs $R^6$ and $R^7$, and $R^8$ and $R^9$ can form a ring comprising from 3 to 8 atoms, optionally bearing substituents, with the proviso that $R^7$ is different from $R^8$ and when $R^7$ is a tert-butyl radical, $R^8$ is not hydrogen;

M is an atom of a transition metal selected from those belonging to group 3, 4, 5, 6 or to the lanthanide or actinide groups in the Periodic Table of the Elements, X, which may be the same or different, is a hydrogen atom, halogen atom, a group $R^{10}$, $OR^{10}$, $OSO_2CF_3$, $OCOR^{10}$, $SR^{10}$, $NR^{10}{}_2$ or $PR^{10}{}_2$, wherein the substituents $R^{10}$ are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms;

p is an integer of from 1 to 3, being equal to the oxidation state of the metal M minus 2; with the proviso that said metallocene compound is different from: isopropylidene (3-trimethylsilylcyclopentadienyl)(7-cyclopentaditiophene)zirconium dichloride, dimethylsilanediyl (3-trimethylsilylcyclopentadienyl)(7-cyclopentaditiophene)zirconium dichloride, isopropylidene (3-ethylcyclopentadienyl)(7-cyclopentaditiophene)zirconium dichloride, dimethylsilanediyl (3 ethylcyclopentadienyl)(7-cyclopentaditiophene)zirconium dichloride, isopropylidene (3-n-butylcyclopentadienyl)(7-cyclopentaditiophene)zirconium dichloride, dimethylsilanediyl (3-n-butylcyclopentadienyl)(7-cyclopenaditiophene)zirconium dichloride, isopropylidene (3-methylcyclopentadienyl)(7-cyclopentaditiophene)zirconium dichloride, dimethylsilanediyl (3-methylcyclopentadienyl)(7-cyclopentaditiophene) zirconium dichloride, isopropylidene (3-i-propylcyclopentadienyl)(7-cyclopentaditiophene)zirconium dichloride and dimethylsilanediyl (3-i-propylcyclopentadienyl)(7-cyclopentaditiophene)zirconium dichloride.

2. The metallocene according to claim 1, wherein the transition metal M is selected from titanium, zirconium or hafnium.

3. The metallocene according to claim 1, wherein L is $CMe_2$ or $SiMe_2$.

4. The metallocene according to claim 1, wherein A or B is a sulfur atom and the other is a CH group.

5. The metallocene according to claim 1, wherein $R^3$ and $R^4$ are the same and are a $C_1$–$C_{20}$-alkyl group, which can contain a silicon atom.

6. The metallocene according to claim 1, wherein G is a moiety of formula (IIIa):

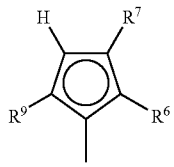

(IIIa)

wherein $R^6$ and $R^9$ equal to or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements;

$R^7$ is a $C_6$–$C_{20}$-aryl, $C_7$–$C_{20}$-alkylaryl or a $QR^{11}R^{12}R^{13}$ group, wherein Q is C, Si, or Ge;

$R^{11}$, $R^{12}$ and $R^{13}$, which may be the same as or different from each other, are hydrogen, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing a heteroatom, with the proviso that when Q is a carbon atom, at least one of $R^{11}$, $R^{12}$ and $R^{13}$ is a hydrogen atom.

7. The metallocene according to claim 6, wherein $R^7$ is a phenyl, a $CHR^{11}R^{12}$ or a $SiR^{11}R^{12}R^{13}$ group, wherein $R^{11}$, $R^{12}$ and $R^{13}$ are hydrogen or $C_1$–$C_{20}$-alkyl groups.

8. The metallocene according to claim 1, wherein G is a moiety of formula (IV):

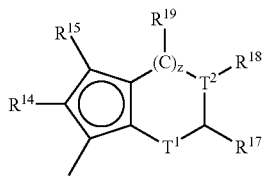

(IV)

wherein $T^1$ is a sulfur atom or a $CR^{16}$ group;

$T^2$ is a carbon atom or a nitrogen atom;

z is 1 or 0;

the ring containing $T^1$ and $T^2$ has double bonds in the allowed position; with the proviso that if z is 1, $T^1$ is a $CR^{16}$ group and $T^2$ is a carbon atom and the ring formed is a benzene ring; and if z is 0, $T^2$ bonds directly the cyclopentadienyl ring, the 5 membered ring formed has double bond in any of the allowed positions having an aromatic character and $T^1$ and $T^2$ are not at the same time, a sulfur atom and a nitrogen atom, $R^{14}$, $R^{15}$, $R^{16}$, $R^{17}$, $R^{18}$ and $R^{19}$, same or different, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, any of two adjacent $R^{14}$, $R^{15}$, $R^{16}$, $R^{17}$, $R^{18}$ and $R^{19}$ can form a ring comprising 4 to 8 atoms optionally bearing substituents.

9. The metallocene according to claim 8, wherein G is a moiety of formula (IVa):

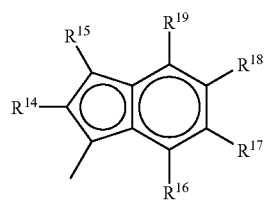

(IVa)

wherein $R^{14}$, $R^{15}$, $R^{16}$, $R^{17}$, $R^{18}$ and $R^{19}$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms, and any of two adjacent $R^{14}$, $R^{15}$, $R^{16}$, $R^{17}$, $R^{18}$ and $R^{19}$, can form a ring comprising 4 to 8 atoms optionally bearing substituents and the benzene ring optionally being perhydrated.

10. The metallocene according to claim 9, wherein G is a moiety of formula (IVb)

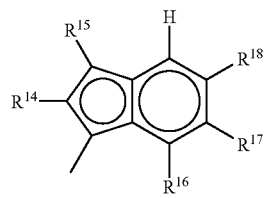

(IVb)

wherein $R^{15}$, $R^{16}$, $R^{17}$, and $R^{18}$ are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and any of two adjacent $R^{15}$, $R^{16}$, $R^{17}$, $R^{18}$ can form a ring comprising 4 to 8 atoms optionally bearing substituents; $R^{14}$ being a $C_1$–$C_{20}$-alkyl or $C_6$–$C_{20}$-aryl group.

11. The metallocene according to claim 9, wherein G is a moiety of formula (IVc)

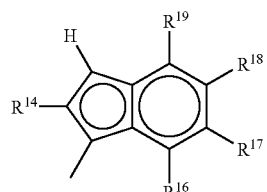

(IVc)

wherein $R^{14}$, $R^{16}$, $R^{17}$, and $R^{18}$ are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and optionally any of two adjacent $R^{16}$, $R^{17}$, and $R^{18}$ can form a ring comprising 4 to 8 atoms optionally bearing substituents;

$R^{19}$ is a $C_1$–$C_{20}$-alkyl or $C_6$–$C_{20}$-aryl group or forms with $R^{18}$ a benzene ring optionally bearing substituents.

12. The metallocene according to claim 11, wherein $R^{14}$ is a $C_1$–$C_{20}$-alkyl or $C_6$–$C_{20}$-aryl group.

13. The metallocene according to claim 11, wherein $R^{16}$ is a $C_1$–$C_{20}$-alkyl or $C_6$–$C_{20}$-aryl.

14. The metallocene according to claim 8, wherein G is a moiety of formula (IVd):

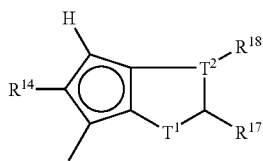

(IVd)

wherein
$T^1$ is a sulfur atom or a $CR^{16}$ group;
$T^2$ a carbon atom or a nitrogen atom;
the 5 member ring formed by $T^1$ and $T^2$ has double bonds in any of the allowed positions, having an aromatic character;
with the proviso that if $T^1$ is a sulphur atom $T^2$ is not a nitrogen atom;
$R^{14}$, $R^{17}$ and $R^{18}$ which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements and $R^{17}$ and $R^{18}$ can form a ring comprising 4 to 8 atoms optionally bearing substituents.

15. The metallocene according to claim 14 wherein $T^2$ is a carbon atom; $T^1$ is a sulphur atom and $R^{14}$, $R^{17}$ and $R^{18}$ equal to or different from each other are a $C_1$–$C_{20}$-alkyl, or $C_6$–$C_{20}$-aryl.

16. A ligand of formula (V):

LG'Z' (V)

wherein L is a divalent group bridging the moieties G and Z, selected from $CR^1R^2$, $SiR^1R^2$ or $(CR^1R^2)_2$, wherein $R^1$ and $R^2$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, and can form a ring having 3 to 8 atoms optionally bearing a substituent;

Z' is a moiety of formula (VI):

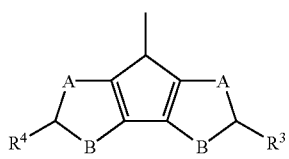

(VI)

or its double bond isomers;
wherein the double bonds are in an allowed position;

$R^3$ and $R^4$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or $CR^5$, wherein $R^5$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom with the proviso that if A is S or O, then B is $CR^5$ or if B is S or O, then A is $CR^5$, and wherein either A or B is different than $CR^5$ and the rings containing A and B have a double bond in the allowed position;

G' is a moiety of formula (VII):

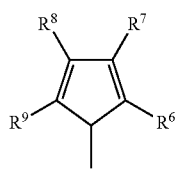

(VII)

or its double bond isomers;
wherein
$R^6$, $R^7$, $R^8$ and $R^9$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and at least one of substituent pairs $R^6$ and $R^7$, and $R^8$ and $R^9$ can form a ring comprising from 3 to 8 atoms, optionally bearing substituents, with the proviso that $R^7$ is different from $R^8$ and when $R^7$ is a tert-butyl radical, $R^8$ is not hydrogen.

17. A process for the preparation of a ligand of formula (V):

LG'Z' (V)

wherein
L is a divalent group bridging the moieties G and Z, selected from $CR^1R^2$, $SiR^1R^2$ or $(CR^1R^2)_2$, wherein $R^1$ and $R^2$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, and can form a ring having 3 to 8 atoms optionally bearing a substituent;

Z' is a moiety of formula (VI):

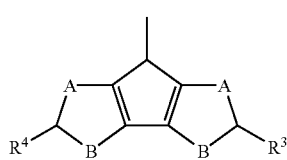

(VI)

or its double bond isomers;
wherein the double bonds are in an allowed position;
$R^3$ and $R^4$, which may be the same as or different from each other, are hydrogen, a $C_1$–$C_{20}$-alkyl, $C_3$–$C_{20}$- cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or $CR^5$, wherein $R^5$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical optionally containing a heteroatom with the proviso that if A is S or O, then B is $CR^5$ or if B is S or O, then A is $CR^5$, and wherein either A or B is different than $CR^5$ and the rings containing A and B have a double bond in the allowed position;

G' is a moiety of formula (VII):

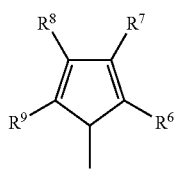

(VII)

or its double bond isomers;
wherein
$R^6$, $R^7$, $R^8$ and $R^9$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and at least one of substituent pairs $R^6$ and $R^7$, and $R^8$ and $R^9$ can form a ring comprising from 3 to 8 atoms, optionally bearing substituents, with the proviso that $R^7$ is different from $R^8$ and when $R^7$ is a tert-butyl radical, $R^8$ is not hydrogen;

comprising the following steps:
a) contacting a compound of the formula (VIII) with a base selected from the group consisting of metallic sodium and potassium, sodium and potassium hydroxide and an organic lithium compound, wherein the molar ratio between the compound of the formula (VIII) and said base is at least 1:1;

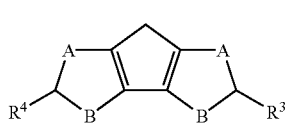

(VIII)

wherein
$R^3$ and $R^4$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or $CR^5$, wherein $R^5$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom with the proviso that if A is S or O, then B is $CR^5$ or if B is S or O, then A is $CR^5$, and wherein either A or B is different than $CR^5$ the rings containing A and B have a double bond in the allowed position;

b) contacting the obtained anionic compounds of the formula from step a) with a compound of formula (IX):

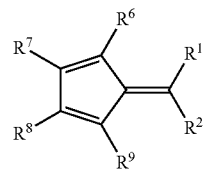

(IX)

wherein
$R^1$ and $R^2$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, and can form a ring having 3 to 8 atoms optionally bearing a substituent;

$R^6$, $R^7$, $R^8$ and $R^9$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and at least one of substituent pairs $R^6$ and $R^7$, and $R^8$ and $R^9$ can form a ring comprising from 3 to 8 atoms, optionally bearing substituents, with the proviso that $R^7$ is different from $R^8$ and when $R^7$ is a tert-butyl radical, $R^8$ is not hydrogen; and then (c) treating the obtained product from step b) with a protonating agent.

18. A process for the preparation of a ligand of formula (V):

LG'Z' (V)

wherein L is a divalent group bridging the moieties G and Z, selected from $CR^1R^2$, $SiR^1R^2$ or $(CR^1R^2)_2$, wherein $R^1$ and $R^2$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, and can form a ring having 3 to 8 atoms optionally bearing a substituent;

Z' is a moiety of formula (VI):

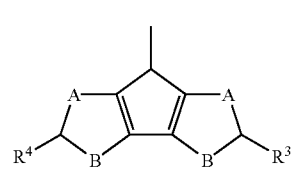

(VI)

or its double bond isomers;
wherein the double bonds are in an allowed position;
$R^3$ and $R^4$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or $CR^5$, wherein $R^5$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom with the proviso that if A is S or O, then B is $CR^5$ or if B is S or O, then A is $CR^5$, and wherein either A or B is different than $CR^5$ and the rings containing A and B have a double bond in the allowed position;

G' is a moiety of formula (VII):

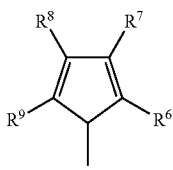

(VII)

or its double bond isomers;

wherein $R^6$, $R^7$, $R^8$ and $R^9$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and at least one of substituent pairs $R^6$ and $R^7$, and $R^8$ and $R^9$ can form a ring comprising from 3 to 8 atoms, optionally bearing substituents, with the proviso that $R^7$ is different from $R^8$ and when $R^7$ is a tert-butyl radical, $R^8$ is not hydrogen;

comprising the following steps:

a) contacting a compound of the formula (VIII) with a base selected from the group consisting of metallic sodium and potassium, sodium and potassium hydroxide and an organic lithium compound, wherein the molar ratio between the compound of the formula (VIII) and said base is at least 1:1

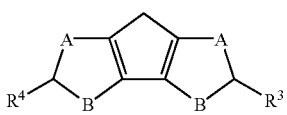

(VIII)

wherein $R^3$ and $R^4$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or $CR^5$, wherein $R^5$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom with the proviso that if A is S or O, then B is $CR^5$ or if B is S or O, then A is $CR^5$, and wherein either A or B is different than $CR^5$ and the rings containing A and B have a double bond in the allowed position;

b) contacting the obtained anionic compounds from step a) with a compound of formula (IX):

(IX)

wherein Y is a halogen radical selected from the group consisting of chloride, bromide and iodide;

L is a divalent group bridging the moieties G and Z, selected from $CR^1R^2$, $SiR^1R^2$ or $(CR^1R^2)_2$, wherein $R^1$ and $R^2$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, and can form a ring having 3 to 8 atoms optionally bearing a substituent;

$R^6$, $R^7$, $R^8$ and $R^9$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and at least one of substituent pairs $R^6$ and $R^7$, and $R^8$ and $R^9$ can form a ring comprising from 3 to 8 atoms, optionally bearing substituents, with the proviso that $R^7$ is different from $R^8$ and when $R^7$ is a tert-butyl radical, $R^8$ not hydrogen.

19. A process for the preparation of a metallocene compound of general formula (I):

LGZMXp (I)

wherein

L is a divalent group bridging the moieties G and Z, selected from $CR^1R^2$, $SiR^1R^2$ or $(CR^1R^2)_2$, wherein $R^1$ and $R^2$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, and can form a ring having 3 to 8 atoms optionally bearing a substituent;

Z is a moiety of formula (II):

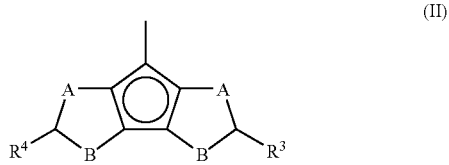

(II)

wherein $R^3$ and $R^4$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or $CR^5$, wherein $R^5$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom with the proviso that if A is S or O, then B is $CR^5$ or if B is S or O, then A is CR⁵, and wherein either A or B is different than CR⁵ and the rings containing A and B have a double bond in an allowed position;

G is a moiety of formula (III):

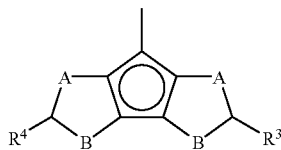

(II)

wherein
R⁶, R⁷, R⁸ and R⁹, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and at least one of substituent pairs R⁶ and R⁷, and R⁸ and R⁹ can form a ring comprising from 3 to 8 atoms, optionally bearing substituents, with the proviso that R⁷ is different from R⁸ and when R⁷ is a tert-butyl radical, R⁸ is not hydrogen;

M is an atom of a transition metal selected from those belonging to group 3, 4, 5, 6 or to the lanthanide or actinide groups in the Periodic Table of the Elements, X, which may be the same or different, is a hydrogen atom, halogen atom, a group $R^{10}$, $OR^{10}$, $OSO_2CF_3$, $OCOR^{10}$, $SR^{10}$, $NR^{10}_2$ or $PR^{10}_2$, wherein the substituents $R^{10}$ are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing heteroatoms;

p is an integer of from 1 to 3, being equal to the oxidation state of the metal M minus 2;

with the proviso that said metallocene compound is different from:

isopropylidene (3-trimethylsilylcyclopentadienyl)(7-cyclopentaditiophene)zirconium dichloride, dimethylsilanediyl (3-trimethylsilylcyclopentadienyl)(7-cyclopentaditiophene)zirconium dichloride, isopropylidene (3-ethylcyclopentadienyl)(7-cyclopentaditiophene)zirconium dichloride, dimethylsilanediyl (3-ethylcyclopentadienyl)(7-cyclopentaditiophene)zirconium dichloride, isopropylidene (3-n-butylcyclopentadienyl)(7-cyclopentaditiophene)zirconium dichloride, dimethylsilanediyl (3-n-butylcyclopentadienyl)(7-cyclopentaditiophene)zirconium dichloride, isopropylidene (3-methylcyclopentadienyl)(7-cyclopentaditiophene)zirconium dichloride, dimethylsilanediyl (3-methylcyclopentadienyl)(7-cyclopentaditiophene)zirconium dichloride, isopropylidene (3-i-propylcyclopentadienyl)(7-cyclopentaditiophene)zirconium dichloride and dimethylsilanediyl (3-i-propylcyclopentadienyl)(7-cyclopentaditiophene)zirconium dichloride;

said process comprising contacting the ligand of general formula (V)

LG'Z'      (V)

wherein L is a divalent group bridging the moieties G and Z, selected from $CR^1R^2$, $SiR^1R^2$ or $(CR^1R^2)_2$, wherein R¹ and R², which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, and can form a ring having 3 to 8 atoms optionally bearing a substituent;

Z' is a moiety of formula (VI):

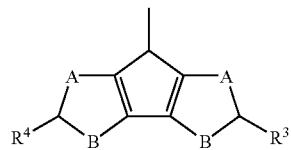

(VI)

or its double bond isomers;
wherein the double bonds are in any of the allowed positions;

R³ and R⁴, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or CR⁵, wherein R⁵ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom with the proviso that if A is S or O, then B is CR⁵ or if B is S or O, then A is CR⁵, and wherein either A or B is different than CR⁵ and the rings containing A and B have a double bond in the allowed position;

G' is a moiety of formula (VII):

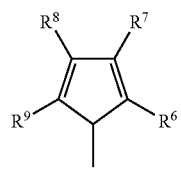

(VII)

or its double bond isomers;
wherein R⁶, R⁷, R⁸ and R⁹, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, and at least one of substituent pairs R⁶ and R⁷, and R⁸ and R⁹ being capable of forming a ring comprising from 3 to 8 atoms, optionally having substituents, with the proviso that R⁷ is different from R⁸ and when R⁷ is a tert-butyl radical, R⁸ is not hydrogen; with a base capable of forming a corresponding dianionic compound and thereafter with a compound of general formula $MX_{p+2}$, wherein M is an atom of a transition metal selected from those belonging to group 3, 4, 5, 6 or to the lanthanide or actinide groups in the Periodic Table of the Elements, X, which may be the same or different, is a hydrogen atom, halogen atom, a group $R^{10}$, $OR^{10}$, $OSO_2CF_3$, $OCOR^{10}$, $SR^{10}$, $NR^{10}_2$ or $PR^{10}_2$, wherein the substituents $R^{10}$ are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms; and p is an integer of from 1 to 3, being equal to the oxidation state of the metal M minus 2.

20. A catalyst obtained by contacting:

(A) a metallocene compound of formula (I)

$$LGZMX_p \quad (I)$$

wherein

L is a divalent group bridging the moieties G and Z, selected from $CR^1R^2$, $SiR^1R^2$ or $(CR^1R^2)_2$, wherein $R^1$ and $R^2$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, and can form a ring having 3 to 8 atoms optionally bearing a substituent;

Z is a moiety of formula (II):

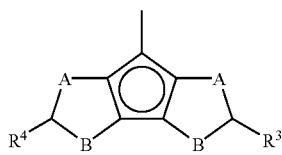

wherein $R^3$ and $R^4$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or $CR^5$, wherein $R^5$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom with the proviso that if A is S or O, then B is $CR^5$ or if B is S or O, then A is $CR^5$, and wherein either A or B is different than $CR^5$ and the rings containing A and B have a double bond in an allowed position;

M is an atom of a transition metal selected from those belonging to group 3, 4, 5, 6 or to the lanthanide or actinide groups in the Periodic Table of the Elements, X, which may be the same or different, is a hydrogen atom, halogen atom, a group $R^{10}$, $OR^{10}$, $OSO_2CF_3$, $OCOR^{10}$, $SR^{10}$, $NR^{10}_2$ or $PR^{10}_2$, wherein the substituents $R^{10}$ are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms;

p is an integer of from 1 to 3, being equal to the oxidation state of the metal M minus 2;

with the proviso that said metallocene compound is different from: isopropylidene (3-trimethylsilylcyclopentadienyl)(7-cyclopentaditiophene)zirconium dichloride, dimethylsilanediyl (3-trimethylsilylcyclopentadienyl)(7-cyclopentaditiophene)zirconium dichloride, isopropylidene (3-ethylcyclopentadienyl)(7-cyclopentaditiophene)zirconium dichloride, dimethylsilanediyl (3-ethylcyclopentadienyl)(7-cyclopentaditiophene)zirconium dichloride, isopropylidene (3-n-butylcyclopentadienyl)(7-cyclopentaditiophene) zirconium dichloride, dimethylsilanediyl (3-n-butylcyclopentadienyl)(7-cyclopentaditiophene) zirconium dichloride, isopropylidene (3-methylcyclopentadienyl)(7-cyclopentaditiophene) zirconium dichloride, dimethylsilanediyl (3-methylcyclopentadienyl)(7-cyclopentaditiophene)zirconium dichloride, isopropylidene (3-i-propylcyclopentadienyl)(7-cyclopentaditiophene)zirconium dichloride and dimethylsilanediyl (3-i-propylcyclopentadienyl)(7-cyclopentaditiophene)zirconium dichloride;

and G is a moiety of formula (III):

wherein $R^6$, $R^7$, $R^8$ and $R^9$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, at least one of substituent pairs $R^6$ and $R^7$, and $R^8$ and $R^9$ can form a ring comprising from 3 to 8 atoms, optionally bearing substituents; with the proviso that $R^7$ is different from $R^8$ and when $R^7$ is a tertbutyl radical $R^8$ is not hydrogen; and (B) at least one of an alumoxane and a compound capable of forming an alkyl metallocene.

21. The catalyst according to claim 20 wherein in the metallocene compound of formula (I) G is a moiety of formula (IIIa)

wherein $R^6$ and $R^9$ equal to or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements $R^7$ is a $C_6$–$C_{20}$-aryl, $C_7$–$C_{20}$-alkylaryl or a $QR^{11}R^{12}R^{13}$ group, wherein Q is C, Si, or Ge;

$R^{11}$, $R^{12}$ and $R^{13}$, which may be the same as or different from each other, are hydrogen, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing a heteroatom, with the proviso that when Q is a carbon atom, at least one of $R^{11}$, $R^{12}$ and $R^{13}$ is a hydrogen atom, or formula (IV)

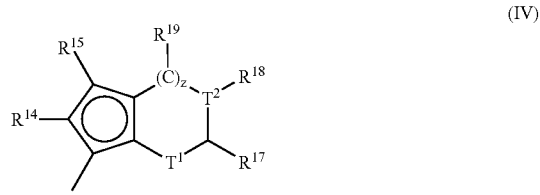

wherein

T$^1$ is a sulfur atom or a CR$^{16}$ group;

T$^2$ is a carbon atom or a nitrogen atom;

z is 1 or 0;

the ring containing T$^1$ and T$^2$ has double bonds in the allowed position;

with the proviso that if z is 1, T$^1$ is a CR$^{16}$ group and T$^2$ is a carbon atom and the ring formed is a benzene ring; and if z is 0, T$^2$ bonds directly the cyclopentadienyl ring, the 5 membered ring formed has double bond in any of the allowed positions having an aromatic character and T$^1$ and T$^2$ are not at the same time, a sulfur atom and a nitrogen atom, R$^{14}$, R$^{15}$, R$^{16}$, R$^{17}$, R$^{18}$ and R$^{19}$, same or different, are hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl, or C$_7$–C$_{20}$-arylalkyl radical, optionally containing heteroatoms belonging to groups 13–17 of the Periodic Table of the Elements, any of two adjacent R$^{14}$, R$^{15}$, R$^{16}$, R$^{17}$, R$^{18}$ and R$^{19}$ can form a ring comprising 4 to 8 atoms optionally bearing substituents.

22. The catalyst according to claim 21 wherein in the metallocene compound of formula (I) G is a moiety selected from the compound of formula (IVa),

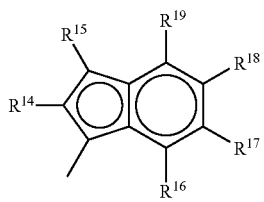

(IVa)

wherein R$^{14}$, R$^{15}$, R$^{16}$, R$^{17}$, R$^{18}$ and R$^{19}$, which maybe the same as or different from each other, are hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl, or C$_7$–C$_{20}$-arylalkyl radical, optionally containing heteroatoms, and any of two adjacent R$^{14}$, R$^{15}$, R$^{16}$, R$^{17}$, R$^{18}$ and R$^{19}$ can form a ring comprising 4 to 8 atoms optionally bearing substituents and the benzene ring optionally being perhydrated, formula (IVb),

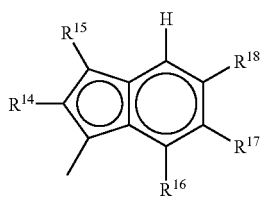

(IVb)

wherein R$^{15}$, R$^{16}$, R$^{17}$, and R$^{18}$ are hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl, or C$_7$–C$_{20}$-arylalkyl radical, optionally containing heteroatoms belonging to groups 13–17 of the Periodic Table of the Elements, and any of two adjacent R$^{14}$, R$^{15}$, R$^{16}$, R$^{17}$, R$^{18}$ can form a ring comprising 4 to 8 atoms optionally bearing substituents; R$^{14}$ being a C$_1$–C$_{20}$-alkyl or C$_6$–C$_{20}$-aryl group, formula (IVc),

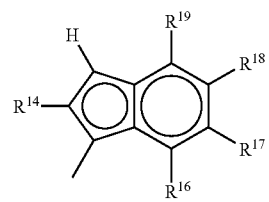

(IVc)

wherein R$^{14}$, R$^{16}$, R$^{17}$, and R$^{18}$ are hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl, or C$_7$–C$_{20}$-arylalkyl radical, optionally containing heteroatoms belonging to groups 13–17 of the Periodic Table of the Elements, and optionally any of two adjacent R$^{14}$, R$^{16}$, R$^{17}$, R$^{18}$ and R$^{19}$ can form a ring comprising 4 to 8 atoms optionally bearing substituents;

R$^{19}$ is a C$_1$–C$_{20}$-alkyl or C$_6$–C$_{20}$-aryl group or forms with R$^{18}$ a benzene ring optionally having substituents, or formula (IVd)

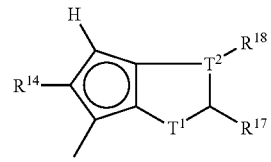

(IVd)

wherein

T$^1$ is a sulfur atom or a CR$^{16}$ group;

T$^2$ is a carbon atom or a nitrogen atom;

the 5 member ring formed by T$^1$ and T$^2$ has double bonds in any of the allowed positions, having an aromatic character;

with the proviso that if T$^1$ is a sulphur atom T$^2$ is not a nitrogen atom;

R$^{14}$, R$^{17}$ and R$^{18}$ which may be the same as or different from each other, are hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl, or C$_7$–C$_{20}$-arylalkyl radical, optionally containing heteroatoms belonging to groups 13–17 of the Periodic Table of the Elements and R$^{17}$ and R$^{18}$ can form a ring comprising 4 to 8 atoms optionally bearing substituents.

23. The catalyst according to claim 20, wherein said alumoxane is selected from methylalumoxane (MAO), isobutylalumoxane (TIBAO) or 2,4,4-trimethyl-pentylalumoxane (TIOAO).

24. The catalyst according to claim 20, wherein the compound capable of forming a metallocene alkyl cation is a compound of formula D$^+$E$^-$, wherein D$^+$ is a Brønsted acid, able to donate a proton and to react irreversibly with a substituent X of the metallocene of formula (I) and E$^-$ is a compatible anion, which is able to stabilize the active catalytic species originating from the reaction of the two compounds, and which is sufficiently labile to be able to be removed by an olefinic monomer.

25. A process for the preparation of a polymer of alpha-olefins comprising contacting one or more alpha-olefins under polymerization conditions with a catalyst obtained by contacting:

(A) a metallocene compound of formula (I)

$$LGZMX_p \qquad (I)$$

wherein

L is a divalent group bridging the moieties G and Z, selected from $CR^1R^2$, $SiR^1R^2$ or $(CR^1R^2)_2$, wherein $R^1$ and $R^2$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom, and can form a ring having 3 to 8 atoms optionally bearing a substituent;

Z is a moiety of formula (II):

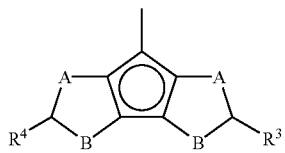

wherein $R^3$ and $R^4$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom;

A and B are sulfur (S), oxygen (O) or $CR^5$, wherein $R^5$ is hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing a heteroatom with the proviso that if A is S or O, then B is $CR^5$ or if B is S or O, then A is $CR^5$, and wherein either A or B is different than $CR^5$ and the rings containing A and B have a double bond in an allowed position;

M is an atom of a transition metal selected from those belonging to group 3, 4, 5, 6 or to the lanthanide or actinide groups in the Periodic Table of the Elements, X, which may be the same or different, is a hydrogen atom, halogen atom, a group $R^{10}$, $OR^{10}$, $OSO_2CF_3$, $OCOR^{10}$, $SR^{10}$, $NR^{10}_2$ or $PR^{10}_2$, wherein the substituents $R^{10}$ are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms;

p is an integer of from 1 to 3, being equal to the oxidation state of the metal M minus 2;

with the proviso that said metallocene compound is different from:

isopropylidene (3-trimethylsilylcyclopentadienyl)(7-cyclopentaditiophene)zirconium dichloride, dimethylsilanediyl (3-trimethylsilylcyclopentadienyl)(7-cyclopentaditiophene)zirconium dichloride, isopropylidene (3-ethylcyclopentadienyl)(7-cyclopentaditiophene)zirconium dichloride, dimethylsilanediyl (3-ethylcyclopentadienyl)(7-cyclopentaditiophene)zirconium dichloride, isopropylidene (3-n-butylcyclopentadienyl)(7-cyclopentaditiophene)zirconium dichloride, dimethylsilanediyl (3-n-butylcyclopentadienyl)(7-cyclopentaditiophene)zirconium dichloride, isopropylidene (3-methylcyclopentadienyl)(7-cyclopentaditiophene)zirconium dichloride, dimethylsilanediyl (3-methylcyclopentadienyl)(7-cyclopentaditiophene)zirconium dichloride, isopropylidene (3-i-propylcyclopentadienyl)(7-cyclopentaditiophene)zirconium dichloride and dimethylsilanediyl (3-i-propylcyclopentadienyl)(7-cyclopentaditiophene)zirconium dichloride;

and G is a moiety of formula (III):

wherein $R^6$, $R^7$, $R^8$ and $R^9$, which may be the same as or different from each other, are hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radical, optionally containing heteroatoms belonging to groups 13–17 of the Periodic Table of the Elements, at least one of substituent pairs $R^6$ and $R^7$, and $R^8$ and $R^9$ can form a ring comprising from 3 to 8 atoms, optionally bearing substituents; with the proviso that $R^7$ is different from $R^8$ and when $R^7$ is a tertbutyl radical $R^8$ is not hydrogen; and (B) at least one of an alumoxane and a compound capable of forming an alkyl metallocene.

26. The process according to claim 25 for the preparation of homo- and copolymers of propylene.

27. The process according to claim 26 wherein the process is carried out in the presence of an alpha-olefins selected from 1-butene, 1-pentene, 1-hexene, 4-methyl-1-pentene, 1-octene, 1-decene or 1-dodecene.

28. The process according to claim 25 for the preparation of homo- and copolymers of ethylene.

29. The process according to claim 28, wherein the process is carried out in the presence of an olefin selected from propylene, 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene, 1-eicosene, allylcyclohexane, cyclopentene, cyclohexene and norbornene, 1,5-hexadiene, 1-6-heptadiene, 2-methyl-1,5-hexadiene, trans 1,4-hexadiene, cis 1,4-hexadiene, 6-methyl-1,5-heptadiene, 3,7-dimethyl-1,6-octadiene, 11-methyl-1,10-dodecadiene, or 5-ethylidene-2-norbornene.

30. The process according to claim 25 wherein the catalyst is supported on an inert carrier.

31. The process according to claim 25 characterized in that it is carried out in gas phase.

32. A propylene homopolymer having the following characteristics:

triads (mm) satisfy the relation 55<mm<85;

melting enthalpy (ΔH) of between 5 J/g and 70 J/g.

Haze (ASTM 2457) from 15% to 30%;

Gloss (60° C.) (ASTM 2457) from 60% to 95%;

Tensile modulus (ASTM D4065) from 1000 MPa to 200 MPa;

Elongation at break (ASTM D4065) from 300% to 900%;

Strength at break (ASTM D638) from 10% to 40% wherein the propylene homopolymer is produced using the catalyst of claim 20.

33. A propylene copolymer containing from 0.1 to 30% by moles of units deriving from an olefin of formula $CH_2$=$CHR'$, R' being hydrogen, a $C_2$–$C_{20}$-alkyl or a $C_6$–$C_{12}$-aryl group, said propylene copolymer having the following characteristics:
  melting enthalpy <70 J/g;
  triads (mm) satisfy the relation: 30<mm<85
  wherein the propylene copolymer is produced using the catalyst of claim 20.

34. The propylene copolymer according to claim 33 wherein the olefin of formula $CH_2{=}CHR'$ is ethylene.

35. The metallocene compound according to claim 1 wherein at least one of $R^3$ and $R^4$ is different than hydrogen.

* * * * *